(12) United States Patent
Reiter et al.

(10) Patent No.: US 6,191,152 B1
(45) Date of Patent: Feb. 20, 2001

(54) 2-(1,2,4-TRIAZOLE-1-YL)-1,3,4-THIADIAZOLE DERIVATIVES HAVING AN EFFECT ON THE C.N.S. AND THE HEART

(75) Inventors: József Reiter; József Barkóczy; Gábor Berecz; Gyula Simig; András Egyed; Katalin Ivanicsné Megyeri; Sándor Drabant; Szabolcs Kertész; Anikó Miklósné Kovács; Ildikó Nagyné Gyönös; Mária Szécseyné Hegedüs; Gábor Szénási; János Wellmann; Katalin Pallagi; Éva Schmidt; Károly Tihanyi; Péter Trinka; Margit Csörgö, all of Budapest (HU)

(73) Assignee: EGIS Gyógyszergyar Rt., Budapest (HU)

( * ) Notice: Under 35 U.S.C. 154(b), the term of this patent shall be extended for 0 days.

(21) Appl. No.: 09/341,362

(22) PCT Filed: Jan. 13, 1998

(86) PCT No.: PCT/HU98/00005

§ 371 Date: Sep. 20, 1999

§ 102(e) Date: Sep. 20, 1999

(87) PCT Pub. No.: WO98/30561

PCT Pub. Date: Jul. 16, 1998

(30) Foreign Application Priority Data

| Jan. 14, 1997 | (HU) | 9700103 |
|---|---|---|
| Jan. 14, 1997 | (HU) | 9700104 |
| Jan. 14, 1997 | (HU) | 9700105 |
| Jan. 14, 1997 | (HU) | 9700106 |

(51) Int. Cl.[7] .................. C07D 417/04; A61K 31/433
(52) U.S. Cl. .................. 514/363; 544/134; 544/367; 546/277; 548/137
(58) Field of Search ............... 548/137, 138, 548/367; 546/227; 514/363

(56) References Cited

FOREIGN PATENT DOCUMENTS

| 9222541A | 12/1992 | (WO) . |
| 9222542A | 12/1992 | (WO) . |

OTHER PUBLICATIONS

Reiter et al; J. Het. Chem., vol. 30, No. 2. 1993 pp. 333–343.

*Primary Examiner*—Robert Gerstl
(74) *Attorney, Agent, or Firm*—Birch, Stewart, Kolasch & Birch, LLP

(57) ABSTRACT

The invention refers to novel 2-(1,2,4-triazole-1-yl)-1,3,4-thiadiazole derivatives of formula (I) having an influence on the heart and the central nervous system, furthermore pharmaceutical compositions containing the above derivatives, and a process for the preparations of the novel compounds. In formula (I) $R^1$ represents a hydrogen atom, a $C_{1-4}$ alkyl group of a phenyl group optionally substituted by 1 to 3 substituents selected from the group defined in the application, Z stands for a hydrogen atom of a $C_{1-4}$ alkoxy group, $R^0$ means a group of the formula Alk—$NR^4R^5$ wherein Alk is a $C_{1-6}$ straight of branched chain alkylene group, $R^4$ and $R^5$ represent, independently, a hydrogen atom, a $C_{2-6}$ alkenyl group, a $C_{1-8}$ alkyl group optionally substituted by a substituent selected from the group defined in the application or $R^4$ and $R^5$ form together with the adjacent nitrogen atom and optionally with one or more further nitrogen and/or oxygen and/or sulfur atom(s) a 5- to 10-membered saturated heterocyclic group, optionally substituted, one of $R^2$ and $R^3$ is an amino group, while the other stands for an amino group of a 5- to 10-membered saturated heterocyclic group containing one or more nitrogen and/or oxygen and/or sulfur atom(s) and being linked through its nitrogen atom, said heterocyclic group being optionally substituted or the latter one of $R^2$ and $R^3$ means a group of formula —SR wherein R represents a $C_{1-8}$ alkyl group, a $C_{2-6}$ alkenyl group or a $C_{2-6}$ alkinyl group, wherein the alkyl group is optionally substituted by a phenyl group of a halophenyl group, and optionally one or both amino group(s) is/are substituted by 1 of 2 substituent(s) selected from the group consisting of a $C_{1-6}$ alkyl group, a $C_{2-6}$ alkenyl group, a phenyl($C_{1-4}$ alkyl) group or a halophenyl-($C_{1-4}$ alkyl) group.

19 Claims, No Drawings

2-(1,2,4-TRIAZOLE-1-YL)-1,3,4-THIADIAZOLE DERIVATIVES HAVING AN EFFECT ON THE C.N.S. AND THE HEART

This application is the national phase under 35 U.S.C. § 371 of PCT International Application No. PCT/HU98/00005 which has an International filing date of Jan. 13, 1998, which designated the United States of America.

The invention refers to novel 2-(1,2,4-triazole-1-yl)-1,3,4-thiadiazole derivatives, a process for the preparation thereof, and pharmaceutical compositions containing the compounds as active ingredient. The novel compounds have an influence on the circulatory system and the heart, as well as the central nervous system.

More specifically, the invention refers to novel 2-(1,2,4-triazole-1-yl)-1,3,4-thiadiazole derivatives of the formula

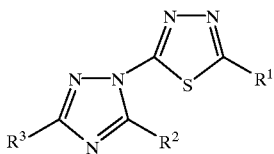

I wherein
$R^1$ represents a hydrogen atom, a $C_{1-4}$ alkyl group or a phenyl group optionally substituted by 1 to 3 substituents selected from the group consisting of a halo atom, a hydroxy group, a nitro group, a $C_{1-4}$ alkoxy group, a $(C_{1-4}$ alkyl)amino group and a di$(C_{1-4}$ alkyl)amino group;
or a group of the formula

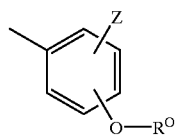

a wherein
Z stands for a hydrogen atom or a $C_{1-4}$ alkoxy group,
$R^0$ means a group of the formula Alk-NR$^4$R$^5$
wherein
Alk is a $C_{1-6}$ straight or branched chain alkylene group,
$R^4$ and $R^5$ represent, independently, a hydrogen atom, a $C_{2-6}$ alkenyl group, a $C_{1-8}$ alkyl group optionally substituted by a substituent selected from the group consisting of a hydroxy group, a $(C_{1-4}$ alkyl)amino group, a di$(C_{1-4}$ alkyl) amino group, a phenyl group—wherein the latter can be substituted by 1 to 3 $C_{1-4}$ alkoxy group(s)—and a 5- or 6-membered saturated heterocyclic group containing one or more nitrogen atom(s) or a nitrogen and an oxygen atom and being linked through its nitrogen atom, said heterocyclic group being optionally substituted by a $C_{1-4}$ alkyl group, or
$R^4$ and $R^5$ form together with the adjacent nitrogen atom and optionally with one or more further nitrogen and/or oxygen and/or sulfur atom(s) a 5- to 10-membered saturated heterocyclic group optionally substituted by a $C_{1-4}$ alkyl group or a phenyl group which latter is optionally substituted by a $C_{1-4}$ alkoxy group, one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R_2$ and $R_3$ means a group of the formula —SR wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group,
and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl-($C_{1-4}$ alkyl) group,
and pharmaceutically acceptable acid addition salts thereof.

1,3,4-Thiadiazole derivatives substituted in position 2 by a substituted morpholino group are described in European Patent Application No. 123 473. The known compounds have antitumor activity. 2-amino-1,3,4-thiadiazoles substituted by an aminoalkyl group in position 5 are known from WO 92/22541. 2-amino-1,3,4-thiadiazoles substituted by an aminoalkylmercapto group in position 5 are described in WO 92/22542. The known thiadiazole derivatives are suitable for the treatment of diseases of the central nervous system as well as hypertension.

The synthesis of 2-(3-methylthio-5-amino-1,2,4-triazol-1-yl)-1,3,4-thiadiazole derivatives bearing a further substituted mercapto group on the thiadiazole ring is described in J. Het. Chem., 30, 333–343 (1993) without any hint at the possible biological effects.

The aim of the invention is to prepare novel 1,3,4-thiadiazole derivatives having cardioprotective effect and/or influencing the central nervous system.

It was found that the above aim was achieved by the novel 2-(1,2,4-triazole-1-yl)-1,3,4-thiadiazole derivatives of the formula I.

In the description and Claims, in the definition of the substituents, under a halo atom primarily a fluoro, chloro, bromo or iodo atom, preferably a fluoro, chloro or bromo atom is meant.

A $C_{1-4}$ alkyl group is a methyl, ethyl, n-propyl, isopropyl, n-butyl, sec.-butyl, tert.-butyl or isobutyl group. Preferably, a $C_{1-4}$ alkyl group is a methyl, ethyl or isopropyl group.

A $C_{1-6}$ alkyl group can be, in addition to alkyl groups listed above, for example, a n-pentyl, 2-methylbutyl, n-hexyl, 2,2-dimethylbutyl or 2,3-dimethylbutyl group etc.

A $C_{1-8}$ alkyl group can be, in addition to the alkyl groups listed above, for example a n-heptyl, 2-methylhexyl, n-octyl or 2,2-dimethylhexyl group etc.

A $C_{2-6}$ alkenyl group can be, for example, a vinyl, allyl, 3-buten-1-yl, 2-buten-1-yl, 3-penten-2-yl, 4-penten-2-yl, 3-hexen-1-yl, 4-hexen-1-yl, 5-hexen-1-yl, 2-hexen-1-yl group etc. Preferably, a $C_{2-6}$ alkenyl group is an allyl group.

A $C_{2-6}$ alkynyl group can be, for example, an ethynyl, propargyl, 2-butyn-1-yl, 3-butyn-1-yl, 2-pentyn-1-yl, 3-pentyn-1-yl, 4-pentyn-1-yl, 3-hexyn-1-yl or 5-hexyn-1-yl group etc. Preferably, a $C_{2-6}$ alkynyl group is a propargyl group.

Primarily, a $C_{1-4}$ alkoxy group is a methoxy, ethoxy, n-propoxy or n-butoxy group, preferably a methoxy group.

Under a 5 to 10 membered saturated heterocyclic group a heterocyclic group containing one or more heteroatom(s) is meant, wherein the heteroatom(s) can be nitrogen and/or oxygen and/or sulfur atom(s), such as a pyrrolidinyl, piperidinyl, morpholinyl, piperazinyl, imidazolidinyl, pyrimidinyl, pyrazolidinyl, hexamethyleneimine-1-yl, heptamethyleneimine-1-yl group etc. Preferably, the above heterocyclic group is a piperidinyl, piperazinyl or morpholine-1-yl group.

Under a 5- or 6-membered saturated hetero-cyclic group containing one or more nitrogen atom(s) or a nitrogen and an oxygen atom preferably a pyrrolidinyl, piperidinyl, piperazinyl or morpholinyl group is meant.

Under a pharmaceutically acceptable acid addition salt an acid addition salt formed with a pharmaceutically suitable inorganic acid such as hydrochloric acid, sulfuric acid, phosphoric acid etc. or with a pharmaceutically suitable organic acid such as acetic acid, fumaric acid, lactic acid, malic acid, tartaric acid etc. is meant.

The invention includes any tautomer forms of the compounds of the formula I and the mixtures thereof.

A subgroup of the novel compounds of the formula I consists of 2-(1,2,4-triazole-1-yl)-1,3,4-thiadiazole derivatives and pharmaceutically acceptable acid addition salts thereof, wherein $R^1$ represents a hydrogen atom, a $C_{1-4}$ alkyl group or a phenyl group optionally substituted by 1 to 3 substituent(s) selected from the group consisting of a halo atom, a hydroxy group, a nitro group, a $C_{1-4}$ allkoxy group, a ($C_{1-4}$ alkyl)amino group and a di($C_{1-4}$ alkyl)amino group, one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl ($C_{1-4}$ alkyl) group.

A further subgroup of the novel compounds of the formula I consists of 5-phenyl-2-(1,2,4-triazole-1-yl)1,3,4-thiadiazole derivatives of the formula

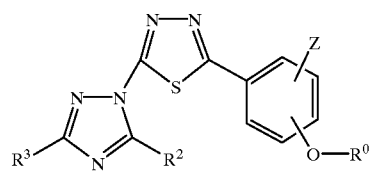

Ia wherein $R^0$ represents a group of the formula Alk-NR$^4$R$^5$, wherein

Alk is a $C_{1-6}$ straight or branched chain alkylene group,
$R^4$ and $R^5$ mean, independently, a $C_{1-6}$ alkyl group or a $C_{2-6}$ alkenyl group, or
$R^4$ and $R^5$ form together with the adjacent nitrogen atom and optionally with one or more further nitrogen and/or oxygen and/or sulfur atom(s) a 5 to 10-membered saturated heterocyclic group optionally substituted by a $C_{1-4}$ alkyl group or a phenyl group which latter is optionally substituted by a $C_{1-4}$ alkoxy group, Z stands for a hydrogen atom or a $C_{1-4}$ alkoxy group, one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl ($C_{1-4}$ alkyl) group, and pharmaceutically acceptable acid addition salts thereof.

A still further subgroup of the novel compounds of the formula I consists of 5-(aminoalkoxyphenyl)-2-(1,2,4-triazole-1-yl)-1,3,4-thiadiazole derivatives of the formula

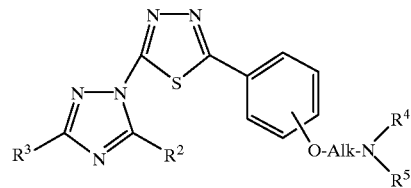

Ib wherein one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group and a halophenyl ($C_{1-4}$ alkyl) group, Alk means a $C_{1-6}$ alkylene group, $R^4$ and $R^5$ represent, independently, a hydrogen atom or a $C_{1-8}$ alkyl group optionally substituted by a substituent selected from the group consisting of a hydroxy group, a ($C_{1-4}$ alkyl)amino group, a di-($C_{1-4}$ alkyl) amino group, a phenyl group—wherein the latter can be substituted by 1 to 3 $C_{1-4}$ alkoxy group(s)—and a 5- or 6-membered saturated heterocyclic group containing one or more nitrogen atom(s) or a nitrogen and an oxygen atom and being linked through its nitrogen atom, said heterocyclic group being optionally substituted by a $C_{1-4}$ alkyl group, and pharmaceutically acceptable acid addition salts thereof.

Preferred novel compounds of the formula I consists of 2-(1,2,4-triazole-1-yl)-1,3,4-thiadiazole derivatives, wherein $R^1$ represents a hydrogen atom, a methyl group, an ethyl group or a phenyl group optionally substituted by 1 to 3 substituent(s) selected from the group consisting of a halo atom, a hydroxy group, a nitro group, a methoxy group and a dimethylamino group, $R^2$ stands for an amino group optionally substituted by a halobenzyl group, $R^3$ means a piperidine-1-yl, piperazine-1-yl, morpholine-1-yl or 4-methylpiperazine-1-yl-group or a group of the formula —SR, wherein R is a methyl group, and pharmaceutically acceptable acid addition salts thereof.

Within the novel compounds of the formula Ia preferred species consist of the 5-phenyl-2-(1,2,4-triazole-1-yl)-1,3,4-thiadiazole derivatives, wherein $R^0$ represents a group of the formula Alk-$NR^4R^5$, wherein Alk stands for an ethylene group or a propylene group, $R^4$ and $R^5$ mean, independently, a $C_{1-3}$ alkyl group, or $R^4$ and $R^5$ form together with the adjacent nitrogen atom a pyrrolidinyl group, $R^2$ is an amino group, $R^3$ stands for an amino group or a piperidinyl or 4-methylpiperazinyl group, said groups being linked through the nitrogen atom, or a group of the formula —SR, Wherein R is a $C_{1-3}$ alkyl group, and optionally the amino group is substituted by two methyl groups or two allyl groups, Z represents a hydrogen atom, and pharmaceutically acceptable acid addition salts thereof.

Within the novel compounds of the formula Ib preferred compounds consist of the 5-(aminoalkoxyphenyl)-2-(1,2,4-triazole-1-yl)-1,3,4-thiadiazole derivatives, wherein $R^4$ represents a hydrogen atom or a $C_{1-2}$ alkyl group, $R^5$ stands for an ethyl group substituted by a substituent selected from the group consisting of hydroxy group, dimethoxy phenyl group and morpholino group, $R^2$ is an amino group, $R^3$ means a piperidyl group or a group of the formula —SR, wherein R stands for a $C_{1-3}$ alkyl group, Alk represents a $C_{2-3}$ alkylene group, and pharmaceutically acceptable acid addition salts thereof.

Especially preferred compounds of the formula I are the following ones:

2-/5-amino-3-(4-methylpiperazino)-1H-1,2,4-triazole-1-yl/-5-(2,6-dichloro-phenyl)-1,3,4-thiadiazole, 2-(5-amino-3-methylthio-1H-1,2,4-triazole-1-yl)-5-/3-(3-dimethylaminopropoxy)phenyl/-1,3,4-thiadiazole, 2-(5-amino-3-dimethylamino-1H-1,2,4-triazole-1-yl)-5-/2-(3-dimethylaminopropoxy)phenyl/-1,3,4-thiadiazole, 2-/5-amino-3-(2-methylethylthio)-1H-1,2,4-triazole-1-yl/-5-/2-(3-dimethylaminopropoxy)phenyl/-1,3,4-thiadiazole, 2-(5-amino-3-piperidino-1H-1,2,4-triazole-1-yl)-5-/2-(3-dimethylaminopropoxy)phenyl/-1,3,4-thiadiazole, 2-(5-amino-3-methylthio-1H-1,2,4-triazole-1-yl)-5-/4-(2-dimethylaminoethoxy)phenyl/-1,3,4-thiadiazole, 2-(5-amino-3-methylthio-1H-1,2,4-triazole-1-yl)-5-/2-(3-pyrrolidinopropoxy)phenyl/-1,3,4-thiadiazole, 2-(5-amino-3-methylthio-1H-1,2,4-triazole-1-yl)-5-[2-/3-di(2-methylethyl)aminopropoxy/-phenyl]-1,3,4-thiadiazole, 2-/5-amino-3-(4-methylpiperazine-1-yl)-1H-1,2,4-triazole-1-yl/-5-/4-(3-dimethylaminopropoxy)phenyl/-1,3,4-thiadiazole, 2-(5-amino-3-diallylamino-1H-1,2,4-triazole-1-yl)-5-/2-(3-dimethylaminopropoxy)phenyl/-1,3,4-thiadiazole, 2-(5-amino-3-pyrrolidino-1H-1,2,4-triazole-1-yl)-5-/2-(3-dimethylaminopropoxy)phenyl/-1,3,4-thiadiazole, 2-(5-amino-3-piperidino-1H-1,2,4-triazole-1-yl)-5-{2-[2-/2-ethyl-2-(2-hydroxyethyl)amino/ethoxy]phenyl}-1,3,4-thiadiazole, 2-(5-amino-3-piperidino-1H-1,2,4-triazole-1-yl)-5-[-2-/2-(2-morpholinoethyl)amino/ethoxy]phenyl-1,3,4-thiadiazole, 2-(5-amino-3-methylthio-1H-1,2,4-triazole-1-yl)-5-{2-[3-methyl-3-/2-(3,4-dimethoxyphenylethyl)amino/propoxy]phenyl}-1,3,4-thiadiazole, 2-(5-amino-3-piperidino-1H-1,2,4-triazole-1-yl)-5-{2-[3-methyl-3-/2-(3,4-dimethoxyphenylethyl)amino/propoxy]phenyl}-1,3,4-thiadiazole, 2-/5-amino-3-(1-methylethylthio)-1H-1,2,4-triazole-1-yl/-5-{2-[3-methyl-3-/2-(3,4-dimethoxyphenylethyl)amino/propoxy]-phenyl}-1,3,4-thiadiazole, 2-(5-amino-3-methylthio-1H-1,2,4-triazole-1-yl)-5-{3-[3-methyl-3-/2-(3,4-dimethoxyphenylethyl)amino/propoxy]phenyl}-1,3,4-thiadiazole, 2-(5-amino-3-methylthio-1H-1,2,4-triazole-1-yl)-5-{4-[3-methyl-3-/2-(3,4-dimethoxyphenylethyl)amino/propoxy]phenyl}-1,3,4-thiadiazole, and pharmaceutically acceptable acid addition salts thereof.

The 2-(1,2,4-triazole-1-yl)-1,3,4-thiadiazole derivatives of the invention are prepared by a) cyclizing a thiocarboxylic acid hydrazone of the formula

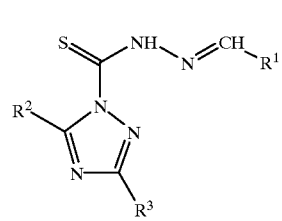

II wherein $R^1$, $R^2$ and $R^3$ are as defined above, with an oxidizing agent; or b) reacting a thiocarboxylic acid hydrazide of the formula

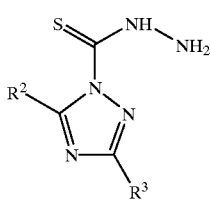

III wherein $R^2$ and $R^3$ are as stated above, with an orthoester of the formula

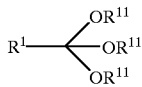

IV wherein $R^1$ is as defined above, $R^{11}$ represents a leaving group; or c) for the preparation of a compound of the formula I, wherein $R^1$ stands for a group of the formula a, $R^2$, $R^3$, $R^0$ and Z are as defined in Claim 1, reacting a phenol of the formula

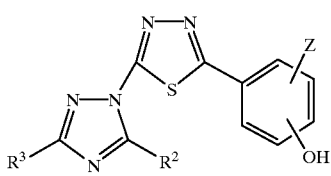

V wherein $R^2$, $R^3$ and Z are as stated above, with an aminoalklylhalide of the formula

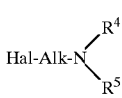

VI wherein Alk, $R^4$ and $R^5$ are as defined in connection with the definition of $R^1$, Hal represents a halo atom; or d) for the preparation of a compound of the formula I, wherein $R^1$ stands for a group of the formula a, $R^2$, $R^3$, $R^0$ and Z are as defined in Claim 1, reacting a halide of the formula

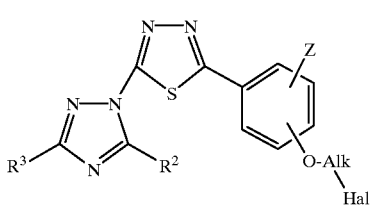

VII wherein $R^2$, $R^3$ and Z are as stated above, Alk is as defined in connection with the definition of $R^1$, Hal represents a halo atom, with an amine of the formula

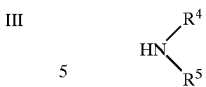

VIII wherein $R^4$ and $R^5$ are as defined in connection with the definition of $R^1$;

and optionally converting a thus-obtained compound of the formula I to a pharmaceutically acceptable acid addition salt thereof, or liberating a compound of the formula I from its salt.

In process a) of the invention, an inorganic or organic oxidizing agent is used.

As an inorganic oxidizing agent a heavy metal halide such as iron(III) chloride, mercury(II) chloride, lead(IV) chloride, antimony pentachloride, thallium(III) chloride, preferably iron(III) chloride is employed. As an organic oxidizing agent a benzoquinone derivative such as 2,3-dichloro-5,6-dicyano-1,4-benzoquinone (DDQ), tetrachloro-1,4-benzoquinone (p-chloranil), 2,3-dichloro-1,4-dihydroxyantraquinone, 6,7-dichloro-1,4-dihydroxyantraquinone or 2,3-dichloro-5,8-dihydroxy-1,4-naphthoquinone, preferably 2,3-dichloro-5,6-dicyano-1,4-benzoquinone (DDQ) is used.

The oxidation of the thiocarboxylic acid hydrazones of the formula II with an inorganic oxidizing agent is carried out in a polar solvent such as water, acetic acid, methanol, acetonitrile or dimethylformamide, preferably in a mixture of water and acetic acid, at a temperature of $-10°$ C. to $120°$ C., preferably $20°$ C. to $100°$ C., for 0.05 to 12 hours, preferably 0.25 to 2 hours.

The ring closure reaction using an organic oxidizing agent is performed in a solvent that is inert from the point of view of the reaction, preferably in tetrahydrofuran, at 0 to $80°$ C., preferably 15 to $20°$ C., for 0.25 to 4 hours, preferably 1 to 1.5 hours.

The reaction product is separated from the reaction mixture by a method known in itself. Thus, if the product crystallizes from the reaction mixture, the crystals are filtered. If the product formed does not precipitates from the reaction mixture mainly due to the solvent used in an excess, the solution is concentrated, and the product precipitated is filtered. In general, the product is purified by recrystallization from a suitable solvent.

In process b) of the invention, the reaction of the thiocarboxylic acid hydrazide of the formula III with an orthoester of the formula IV is carried out in a polar solvent such as alcohols, preferably methanol under reflux, however, the reaction can be also performed in an excess of the orthoester of the formula IV. In this case, the excess of the orthoester has the role of the solvent.

In formula IV, $R^{11}$ represents a leaving group. This is a group that leaves the reagent during the reaction. If $R^{11}$ stands for an alkyl group such as an ethyl group, it forms together with the adjacent oxygen atom and a hydrogen atom leaving the thiocarboxylic acid hydrazide of the formula III an ethanol during the reaction.

In the meaning of $R^{11}$, a preferred leaving group is a $C_{1-4}$ alkyl group.

The reaction product is separated from the reaction mixture by a method known in itself. Thus, if the product crystallizes from the reaction mixture, the crystals are filtered. If the product formed does not precipitates from the reaction mixture mainly due to the solvent used in an excess, the solution is evaporated to dryness, and the residual product is purified by recrystallization from a suitable solvent.

In process c) of the invention, the reaction of the phenol of the formula V with an aminoalkylhalide of the formula VI is carried out in the presence of an organic or inorganic base in a solvent that is inert from the point of view of the reaction.

The inorganic base is, for example, an alkali metal or alkali earth metal hydroxide, preferably potassium or sodium hydroxide, the organic base is generally a tetraalkylammonium hydroxide, preferably tetrabutylammonium hydroxide. Calculated for the phenol of the formula V, the base can be employed in a molar ratio or in a slight i.e. 0.1 to 0.5 molar excess. Calculated for the phenol of the formula V, the aminoalkyl-halide of the formula VI is used in a molar ratio or in a 0.1 to 1 molar excess.

If an organic base is used, it is suitable to prepare the corresponding tetraalkylammonium hydroxide separately, then to react this compound with the aminoalkylhalide of the formula VI.

In the reaction, the solvent can be alcohols, preferably methanol or ethanol, ketones, preferably acetone or methyl ethyl ketone, acetonitrile, dimethylformamide, dimethyl sulfoxide, halogenated solvents, preferably 1,2-dichloroethane or chlorobenzene.

The reaction product is separated from the reaction mixture by a method known in itself. Thus, if a solvent is used from which the product crystallizes, the crystals are filtered and purified by recrystallization. If the product formed does not precipitates from the reaction mixture, in case of using water-immiscible solvents, the reaction mixture is diluted with water, the phases are separated, the organic phase is evaporated, and the residual product is purified by a simple recrystallization. In case of water-miscible solvents, the product is precipitated with water, then filtered, or the solvent is evaporated, and the residue is distributed between water and a water-immiscible solvent, then the organic phase is separated, evaporated, and the residue is recrystallized.

In process d) of the invention, the reaction of the halide of the formula VII with the amine of the formula VIII is carried out suitably in an excess of the amine, however, the reaction can be also performed in a solvent being inert from the point of view of the reaction.

As an inert solvent alcohols, preferably methanol or ethanol, acetonitrile, dimethylformamide, dimethyl sulfoxide, halogenated solvents, preferably 1,2-dichloroethane or chlorobenzene can be used.

The product is separated from the reaction mixture by any of the methods described above.

If the reaction mixture is evaporated, it can be suitable to distribute the evaporation residue between water and a water-immiscible solvent, to make the mixture alkaline, to separate the phases, and, after the evaporation of the organic phase, to purify the residual base by recrystallization.

If the compound of the formula I is converted to an acid addition salt, suitably the base of the formula I is dissolved in a convenient solvent, the corresponding acid is added, and after cooling, the salt crystallized is filtered.

The thiocarboxylic acid hydrazones of the formula II are known from the literature (Hungarian Patent Specification No. 206 094) or can be easily prepared by the method described therein. The preparation of some compounds is shown in the description by means of examples.

The thiocarboxylic acid hydrazides of the formula III are known from the literature (Hungarian Patent Specification No. 206 095).

The compounds of the formula IV are commercially available.

The compounds of the formulae VI and VIII are commercially available.

The phenol of the formula V is prepared from the corresponding thiocarboxylic acid hydrazone, wherein $R^1$ is a hydrogen atom, by ring closure under the conditions described in process a).

The invention includes also the novel intermediates of the formula

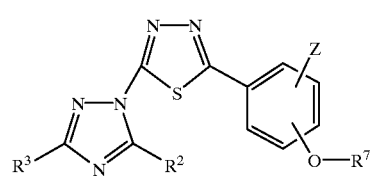

IX wherein
$R^7$ means a group of the formula —Alk-L, wherein
Alk represents a $C_{1-6}$ straight or branched chain alkylene group,
L stands for a halo atom or a hydroxy group,
Z is a hydrogen atom or a $C_{1-4}$ alkoxy group, one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein
R represents a $C_{1-8}$ alkyl group, a $C_{2-6}$ alkenyl group or a $C_{2-6}$ alkynyl group, wherein the alkyl group is optionally substituted by a phenyl group or a halophenyl group,
and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl-($C_{1-4}$ alkyl) group,
and acid addition salts thereof.

The compounds of the formula IX comprise the halides of the formula VII, too.

The intermediates of the formula IX are prepared by cyclizing a thiocarboxylic acid hydrazone of the formula

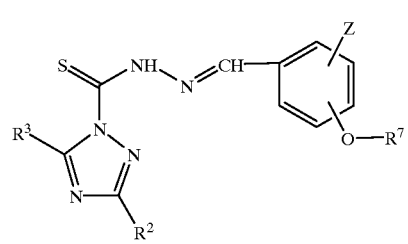

X wherein
$R^2$, $R^3$, $R^7$ and Z are as defined above, with an oxidizing agent. The reaction is performed in a similar way as described under process a).

The compounds of the formula IX, wherein L stands for a halo atom, $R^2$, $R^3$, Z and Alk are as defined above, can be also prepared by reacting a phenol of the formula V with a dihaloalkane of the formula Hal—Alk—Hal    XI wherein Hal represents a halo atom, Alk is as stated above. The reaction is carried out in a polar solvent such as an alcohol, preferably methanol, in the presence of an inorganic or organic base. An excess of the dihaloalkane of the formula XI can be used as a solvent, too.

The base is used in an equimolar amount or in a small (0.1 to 0.5 molar) excess. As an inorganic base preferably an alkali metal or an alkali earth metal hydroxide, suitably sodium hydroxide or potassium hydroxide, while as an organic base for example a tertiary amine or a tetraalkyl ammonium hydroxide e.g. triethyl amine, dimethyl aniline, tetrabutyl ammonium hydroxide or benzyl trimethyl ammonium hydroxide may be used.

The reaction is carried out at a temperature between room temperature and the boiling point of the reaction mixture, preferably at 40 to 80° C.

Intermediates of the formula IX, wherein L stands for a halo atom, can be also prepared by reacting a hydroxy compound of the formula

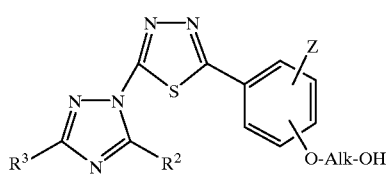

XII wherein $R^2$, $R^3$, Z and Alk are as defined above, with a halogenating agent. The reaction is carried out by using a suitable halogenating agent in an inert solvent. As reaction medium for example an aromatic hydrocarbon, preferably benzene or toluene, or a halogenated hydrocarbon e.g. chlorobenzene, chloroform, dichloromethane or carbon tetrachloride may be used.

As a halogenating agent halides of metals of the $5^{th}$ or $6^{th}$ group of the periodical system may be applied e.g. phosphorous trichloride, phosphorous pentachloride, phosphorous oxychloride, thionyl chloride, preferably phosphorous oxychloride or thionyl chloride.

The halogenation reaction can be performed at a temperature between room temperature and the boiling point of the reaction mixture, preferably at 40 to 70° C.

The hydroxy compound of the formula XII can be prepared by reacting a phenol of the formula V with a hydroxyalkylhalide of the formula

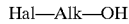 Hal—Alk—OH XIII wherein Hal represents a halo atom, Alk is as stated above. The reaction is carried out in a similar way as described in connection with the reaction of the phenol of the formula V with a dihaloalkane of the formula XI.

If desired, the intermediate of the formula IX is converted to an acid addition salt in a manner known in itself, or deliberated from the acid addition salt in a manner known in itself.

Biological effects of the 2-(1,2,4-triazole-1-yl)-1,3,4-thiadiazole derivatives of the invention were studied in the following experiments.

1. Measurement of Vascular Relaxing Effect in Potassium Chloride Contracted Isolated rat Thoracic Aorta Experiments were performed in thoracic aortas obtained from male SPRD rats weighing 250 to 300 g. Thoracic aortas excised from rats killed by decapitation and ensanguination were cleaned of fat and connective tissue, then were immediately placed in carbogenized TYRODE solution. The composition of the normal TYRODE solution was the following (in mM): NaCl 114.7, KCl 3.7, $CaCl_2$ 3.6, $MgCl_2$ 0.49, $NaHCO_3$ 19.9, $NaH_2PO_4$ 0.32, glucose 5.1.

Two mm wide and 20 to 25 mm long strips were cut from the aortas along a helical line at 45° angle. Aortic strips were mounted vertically between two cotton threads in 10 ml organ chambers, the lower threads were attached to the organ chambers and the upper threads were connected to isometric force transducers. The strips were incubated under 1 g resting tension at 37° C. for 120 minutes, then resting vascular tone was recorded. Then the strips were contracted with a TYRODE solution containing 20 mM KCl. The composition of the high potassium TYRODE solution was the following (in mM): NaCl 94.7, KCl 20, $CaCl_2$ 3.6, $MgCl_2$ 0.49, $NaHCO_3$ 19.9, $NaH_2PO_4$ 0.32, glucose 5.1.

When stable vascular tone developed, increasing doses of the test substance were added to the organ bath. The effects of each test substance were measured at least in 3 tissue preparations obtained from different animals. Decreases in vascular tension caused by the test substances were expressed as percentage changes and $IC_{50}$ for each tissue preparation was determined by sigmoid (in few casses linear) curve fitting. $IC_{50}$ values were averaged for each test substance and are shown in Table I.

For comparison, cromakalim i.e. (±)-trans-3,4-dihydro-3-hydroxy-2,2-dimethyl-4-(2-oxo-1-pyrrolidinyl)-2H-1-benzopyrane-6-carbonitrile was used.

For additional comparison, diltiazem i.e. (2S)-cis-3-acetyloxy-5-(2-dimethylamino-ethyl)- 2,3-dihydro-2-(4-methoxyphenyl)-1,5-benzothiazepine-4(5H)-one was employed.

Diltiazem is a calcium channel blocker, therefore, its effects were tested in vessels contracted with a Tyrode solution containing 40 mM potassium chloride. The test methods were in all respect identical to those described above except that isolated rat thoracic aorta strips were contracted with modified TYRODE solution containing 40 mM potassium chloride. The composition of the high potassium TYRODE solution was the following (in mm): NaCl 74.7, KCl 40, $CaCl_2$ 3.6, $MgCl_2$ 0.49, $NaHCO_3$ 19.9, $NaH_2PO_4$ 0.32, glucose 5.1.

TABLE I

Vascular relaxation in isolated rat thoracic aorta

| Compound (No. of Example) | $IC_{50}$ in M |
|---|---|
| cromakalim | $1.3 \times 10^{-7}$ |
| diltiazem | $1.5 \times 10^{-7}$ |
| 10 | higher than $10^{-5}$ |
| 26 | higher than $10^{-5}$ |
| 29 | $7.1 \times 10^{-8}$ |
| 30 | $6.8 \times 10^{-8}$ |
| 45 | higher than $10^{-6}$ |
| 49 | $1.7 \times 10^{-7}$ |
| 90 | higher than $10^{-5}$ |
| 91 | higher than $10^{-6}$ |
| 99 | $1.3 \times 10^{-7}$ |
| 101 | $7.5 \times 10^{-8}$ |
| 105 | higher than $10^{-6}$ |
| 108 | higher than $10^{-5}$ |

Some of the compounds tested such as derivatives given in Examples 29, 30 and 101 relaxed isolated rat thoracic aorta more effectively than the $K^+$ channel opener and $Ca^{2+}$ channel blocker reference substances. It was very favourable that the other derivatives having cardioprotective and/or antiarrhythmic effects caused no vascular relaxation.

2. Measurement of Effective Refracter Period in Guinea-pig Right Ventricular Papillary Muscle, in Vitro.

Effective refracter period (ERP) is regarded to be the shortest time interval between two identical electrical stimuli when both can evoke a twitch in the papillary muscle. A second stimulus applied earlier than the ERP is not effective. Compounds prolonging ERP can have antiarrhythmic effect. This method is useful primarily for testing antiarrhythmic agents belonging to class III according to the Vaughan Williams classification /Bexton, R. S. and Camm. A., J. Pharmacol. Ther., 17, 315 (1982)/.

Experiments were performed in a Schuler-type organ bath system having 4 channels. Male guinea-pigs weighing 450 to 750 g were killed by a blow on the head and ensanguinated. The heart was rapidly excised and papillary muscles of appropriate size (lower than 1 mm in diameter) were dissected from the right ventricle. The preparations were vertically mounted in 20 ml organ chambers containing Krebs solution bubbled with carbogen (consisting of 95% of $O_2$ and 5% of $CO_2$) and maintained at 35° C. The upper end of the muscles was connected with cotton threads to force-displacement transducers coupled to a recorder for measuring isometric tension via DC-bridge amplifiers. The lower end of the papillary muscles was pinned to the organ chamber with a silver hook that was also used as a stimulating electrode. The other electrode was immersed into the organ bath and had no direct contact with the preparation. The composition of the Krebs solution was the following (in mm): NaCl 118, KCl 4.8, $NaHCO_3$ 27.2, glucose 11.1, $MgSO_4$ 1.2, $KH_2PO_4$ 1, $CaCl_2$ 2.6, pH=7.4.

The preparations were equilibrated for 120 minutes under a resting tension of 1 g. During equilibration they were electrically stimulated at a rate of 2 Hz with 1 msec rectangular pulses that were above the diastolic threshold voltage by 10%. ERP was determined using a standard extrastimulus technique. Extrastimuli ($S_2$) were interjected between the normal stimuli ($S_1$) in such a way that the $S_1$–$S_2$ interval was initially below the refracter period of the tissue. The $S_1$–$S_2$ interval was then widened by increments of 1 msec until the extrastimulus ($S_2$) evoked twitch of the papillary muscle. The force of the twitch caused by $S_2$ is larger than those caused by normal ($S_1$) stimuli (postextrasystolic potentiation). The equipment measured the shortest $S_1$–$S_2$ interval at which the extrastimulus evoked a twitch that was larger than the force of control twitches by 25%. This interval is equivalent with the ERP.

The experimental protocol was as follows:

Two control ERP measurements were performed 20 minutes apart, then appropriate amount of the test substance was added to produce $10^{-4}$ M concentration in the bathing solution. After 30 minutes incubation with the test substance, two ERP measurements were performed 30 minutes apart.

When the test substance increased ERP at $10^{-4}$ M by 40 msec or more, its effect on ERP was tested also at $10^{-5}$ M.

The effect of the test substances was characterized by the difference between the first treated and the second control measurements. Individual data obtained from four different preparations, at least, were averaged. Mean values obtained are presented in Table II. The reference substance used was sotalol i.e. N-[4-/1-hydroxy-2-(1-methylethylamino)ethyl/plenyl]methane sulfonamide.

TABLE II

Effective refractory period (ERP) prolonging effect in isolated guinea-pig papillary muscle

| Compound (No. of Example) | ERP change (in msec) at | |
|---|---|---|
| | $10^{-4}$ M | $10^{-5}$ M |
| sotalol | 47 | 26 |
| 10 | 120 | 32 |
| 26 | 148 | 21 |
| 32 | 155 | 158 |
| 36 | 53 | 15 |
| 43 | 66 | 34 |
| 47 | 123 | 2 |
| 105 | 62 | 14 |
| 108 | 66 | 29 |

As it can be seen from Table II, many of the novel compounds of the invention considerably prolonged ERP at $10^{-4}$ M, with a greater effectiveness than did the reference substance sotalol. Moreover, the effect of compound of Example 32 was remarkable also at $10^{-5}$ M.

3. Measurement of Cardioprotective Effect in Ischemic rat Heart (Langendorff) Preparation If the blood supply to a part of the myocardium is interrupted (e.g. during myocardial infarction), then the intracellular calcium concentration starts to rise and gradually attains pathophysiological levels. Myocardial contraction is regulated by calcium, therefore, high intracellular calcium concentration results in contracture of the myocardium. In isolated rat hearts, contracture develops in about 10 minutes after starting global ischemia, and this period is called time to contracture (TTC). Any substance which can inhibit the rise of intracellular calcium concentration and the development of contracture caused by high calcium concentration during ischemia protects the myocardium from impairment i.e. it has cardioprotective effect. Under experimental conditions, the cardioprotective effect of drugs is shown by their ability to prolong TTC. The cardioprotective effect of the compounds of the invention was examined by measuring TTC in globally ischemic Langendorff rat hearts/ Longman, S. D. and Hamilton, T. C., Medicinal Research Reviews, 12, 73–148 (1992)/.

Male Wistar rats weighing 300 to 350 g were injected with 2500 IU (0.5 ml) of heparin i.p. and 10 minutes later they were anaesthetized with sodium pentobarbital/5-ethyl-5-(1-methylbutyl)-2,4,6(1H,3H,5H)-pyrimidinetrione sodium salt/in a dose of 60 mg/kg i.p. The heart was quickly excised and connected to a Langendorff apparatus via the aorta. The hearts were perfused at a constant perfusion pressure (60 mmHg) and temperature (37° C.) with a modified Krebs-Henseleit solution gassed with 95% of $O_2$ and 5% of $CO_2$. The composition of the modified Krebs-Henseleit solution was the following (in mM): NaCl 118, KCl 4.7, $CaCl_2$ 2.5, $NaHCO_3$ 24.88, $KH_2PO_4$ 1.18, $MgSO_4$ 1.6, EDTA 0.5 and glucose 11. Partial $O_2$ and $CO_2$ pressures and also pH were measured and maintained within normal limits ($pO_2$== 64000–77000 Pa, $pCO_2$=3800–4500 Pa, pH=7.3–7.45). A hole was cut in the wall of the left atrium and a water-filled plastic balloon attached to a metal cannula was then inserted into the left ventricle via the left atrium for measuring left ventricular pressure. End diastolic pressure was set to about 645 Pa, and adjusted for during the equilibration period but not later.

After a 20 minutes equilibration period, the hearts were perfused for 10 minutes with the test substance at $10^{-5}$ or $10^{-6}$ concentration or with the vehicle (0.04% of dimethyl sulfoxide). Global ischemia was initiated by completely shutting off the perfusate flow and carbogenization for 25 minutes. During ischemia, the time period from the beginning of ischemia until 645 Pa increase in left ventricular end diastolic pressure was measured (TTC).

Three experiments were performed with the test substances at each concentration and parameters of 3 additional vehicle treated hearts were measured along with the test substance.

Individual TTC values were averaged and the effect of the test substances was expressed as a percentage change compared to the vehicle treated group. Compounds that prolong TTC are cardioprotective. The results obtained are shown in Table III. As a reference substance, lemakalim i.e. (3S)-trans-3,4-dihydro-3-hydroxy-2,2-dimethyl-4-(2-oxo-1-pyrrolidinyl)-2H-1-benzpyrane-6-carbonitrile was used.

TABLE III

TTC prolonging effect in isolated Langendorff rat hearts

| Compounds (No. of Example) | TTC change (in %) at | |
|---|---|---|
| | $10^{-5}$ M | $10^{-6}$ M |
| lemakalin | 55 | 20 |
| 10 | 74 | 47 |
| 26 | 41 | 33 |
| 45 | 31 | 30 |
| 90 | 36 | 19 |
| 91 | not measured | 58 |

Some of the novel compounds of the invention caused a higher TTC prolongation than the reference substance lemakalim did.

According to the data presented in Tables I and III, the TTC prolonging compounds caused no vascular relaxation, contrary to lemakalim which prolonged not only TTC but considerably relaxed isolated rat thoracic aorta. Thus, these novel 1,3,4-thiadiazole derivatives demonstrated myocardium selectivity. It is favourable if a cardioprotective drug has no vascular relaxing, and in consequence, hypotensive effect since hypotension caused by a cardioprotective compound can be regarded as an unwanted side effect in the majority of the patients.

Some of the novel compounds, e.g. the one of Example 26, prolonged not only TTC but ERP as well. These results demonstrate the presence of double, cardioprotective and antiarrhythmic effectiveness of some novel compounds. This profile raise the possibility of an outstandingly favourable therapeutic use since, by administering a single drug, cardioprotective effect and prevention of arrhythmias frequently occurring in heart failure patients can be achieved. Such a compound is superior to both reference drugs that are suitable only for a single therapeutic use.

In summary, data obtained in the pharmacological studies of the 1,3,4-thiadiazole derivatives of the invention convincingly established that some of these compounds have desirable vascular and myocardial effects. The effectiveness of some 1,3,4-thiadiazole derivatives exceeded that of the therapeutically established reference substances regarding both their potency and tissue selectivity. Some derivatives have considerable vascular relaxing effect, therefore, these derivatives may be useful for the treatment of hypertension and vasodilator therapy in pheripheral vascular diseases. Among the latter therapeutic indications, ischemic heart disease and cerebral vascular spasm (stroke) are to be mentioned. Based on their effects on the heart, other compounds of the invention are suitable for the treatment of ventricular arrhythmia and for prevention of myocardial damage caused by insufficient coronary blood supply occurring in ischemic heart disease or during heart surgery i.e. for cardioprotection against the effects of unavoidable ischemic insults of the myocardium.

4) $5\text{-HT}_{2A}$ and $5\text{-HT}_{2C}$ Receptor Binding Studies $5\text{-HT}_{2A}$ and $5\text{-HT}_{2C}$ receptor binding was measured according to the methods described by Leysen et al. /Mol. Pharmacol., 21, 301 (1981)/and Pazos et al. /Eur. J. Pharmacol., 106, 539 (1985)/, respectively. $5\text{-HT}_{2A}$ receptor binding was measured in rat brain frontal cortex membrane preparation using tritiated ketanserine /3-/2-(4-fluorobenzoyl)-1-piperidinyl/ethyl-2,4-(1H,3H)-quinazolinedione/(60–90 Ci/mmole) as ligand. $5\text{-HT}_{2C}$ receptor binding was measured in pig brain choroid plexus membrane-preparation using tritiated mesulergine /N'-/(8)-1,6-dimethylergoline-8-yl/-N,N-dimethylsulfamide (70–85 Ci/mmole) as the ligand. Non-specific binding to $5\text{-HT}_{2A}$ and $5\text{-HT}_{2C}$ receptors were determined in the presence of 10 micromoles of cyproheptadine /4-(5H-dibenzo/a,d/cycloheptene-5-ylidene)-1-methylpiperidine/and 1 micromole of mianserine /1,2,3,4,10,14b-hexahydro-2-methyldibenzo/c,f/pyrazino/1,2-a/azepine/, respectively. The final incubation volumes were 250 and 1000 microlitres. Samples were incubated for 15 and 30 minutes at 37° C. Incubation was stopped by adding 9 ml of ice-cold 50 mr-tris(hydroxymethyl)aminomethane hydrochloride (pH=7.7) to the reaction mixture. The samples were rapidly filtered through whatman GF/B glass fiber filters using reduced pressure. Before use, the filters were soaked in a 0.05% polyethyleneimine solution for 2 to 3 hours. Radioactivity of the filters was determined by a scintillation spectrometer.

The results obtained are shown in Table IV.

TABLE IV

Effect of the compounds on $5\text{-HT}_{2A}$ and $5\text{-HT}_{2C}$ receptors

| Compound (Example No.) | Inhibition of receptor binding of the radioactive ligand ($K_i$ in nm/l) | |
|---|---|---|
| | $5\text{-HT}_{2C}$ | $5\text{-HT}_{2A}$ |
| 44 | 50 | higher than 100 |
| 98 | 24 | higher than 1000 |

It can be seen in Table IV that the novel compounds of the invention have considerable affinity for $5\text{-HT}_{2C}$ receptors with moderate to high degree of selectivity over $5\text{-HT}_{2A}$ receptors. Thus, the compounds can be applied for the treatment of disorders developed on grounds of pathological changes in the central nervous system.

Some compounds of the invention demonstrated affinity primarily at $5\text{-HT}_{2C}$ serotonergic receptor subtypes. It has been described in the scientific literature that the above receptor plays a basic role in the pathomechanism of anxiety disorders, schizophrenia and migraine. The $5\text{-HT}_{2C}$ recetor agonist m-chlorophenylpiperazine /Conn et al., Proc. Natl. Acad. Sci. USA, 83, 4086 (1986)/induces anxiety both in rats /Kennett et al., Eur. J. Pharmacol., 164, 455 (1989)/and human beings /Kahn and Weltzer, Biol. Psychiat., 30, 1139 (1991)/. Based on studies performed in rats, the anxiogenic effect of m-chlorophenylpiperazine can be attributed to the activation of $5\text{-HT}_{2C}$ receptors /Kennett et al., Eur. J. Pharmacol., 164, 455 (1989)/. Compounds with antagonistic effect at $5\text{-HT}_{2A/2C}$ receptors have been shown to be anxiolytic in animal experiments /Kennett, Psychopharmacol., 107, 379 (1992)/. The $5\text{-HT}_{2A/2C}$ receptor antagonistic compound ritanserin /6-[2-/4-bis(4-fluorophenyl)-methylene/-1-piperidinylethyl]-7-methyl-5H-thiazolo/3,2-a/pyrimidine-5-one/has been proved to be effective for the treatment of different forms of human anxiety /Ceulemans et al., Pharmacopsychiat., 18, 303 (1985)/. It has to be emphasized that compounds with selective binding at 5-HT$_{2C}$ receptors can be advantageous compared to compounds having affinity for both 5-HT$_{2A}$ and 5-HT$_{2C}$ receptor subtypes.

Usefulness of the novel compounds of the invention for prophylactic treatment of migraine is supported by the 5-HT$_{2C}$ receptor antagonistic properties of the compounds /Sleight et al. in Serotonin Receptor Subtypes: Basic and Clinical Aspects, ed. Peroutka, S. J., pp. 211, Wiley-Liss Inc., 1991/.

Thus, some of the novel compounds of the invention can be used especially for the treatment of heart insufficiency and/or arrhythmia, while other compounds of the invention are useful in the treatment of a disease of the central nervous system.

Due to the above test results, the novel 2-(1,2,4-triazole-1-yl)-1,3,4-thiadiazole derivatives of the formula I and pharmaceutically acceptable acid addition salts thereof can be used as active ingredients of pharmaceutical compositions. The pharmaceutical compositions of the invention contain a therapeutically active amount of the compound of the formula I or a pharmaceutically suitable acid addition salt thereof and one or more conventional carrier(s).

The pharmaceutical compositions of the invention are suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinyl- pyrrolidone) etc.; filling agents such as lactose, glucose, starch, calcium phosphate etc.; auxiliary substances for tabletting such as magnesium stearate, talc, poly(ethyleneglycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propyleneglycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18th Edition, Mack Publishing Co., Easton, USA (1990).

The pharmaceutical compositions of the invention contain, in general, 0.1 to 95.0 per cent by mass of a compound of the formula I or a pharmaceutically acceptable acid addition salt thereof. A typical dose for adult patients amounts to 0.1 to 20 mg of the compound of the formula I or a pharmaceutically acceptable acid addition salt thereof, daily. The above dose can be administered in one or more portions. The actual dosage depends on many factors and is determined by the doctor.

The pharmaceutical compositions of the invention are prepared by admixing a compound. of the formula I or a pharmaceutically acceptable acid addition salt thereof to one or more carrier(s), and converting the mixture obtained to a pharmaceutical composition in a manner known per se. Useful methods are known from the literature, e.g. Remington's Pharmaceutical Sciences.

A subgroup of the pharmaceutical compositions of the invention contain a 2-(1,2,4-triazole-1-yl)-1,3,4-thiadiazole derivative of the formula I, wherein $R^1$ represents a hydrogen atom, a $C_{1-4}$ alkyl group or a phenyl group optionally substituted by 1 to 3 substituent(s) selected from the group consisting of a halo atom, a hydromy group, a nitro group, a $C_{1-4}$ alkoxy group, a ($C_{1-4}$ alkyl)amino group and a di($C_{1-4}$ alkyl)amino group, one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl ($C_{1-4}$ alkyl) group, or a pharmaceutically acceptable acid addition salt thereof as the active ingredient.

A further subgroup of the pharmaceutical compositions of the invention contain a 5-phenyl-2-(1,2,4-triazole-1-yl)1,3,4-thiadiazole derivative of the formula Ia, wherein $R^0$ represents a group of the formula Alk-NR$^4$R$^5$, wherein Alk is a $C_{1-6}$ straight or branched chain alkylene group, $R^4$ and $R^5$ mean, independently, a $C_{1-6}$ alkyl group or a $C_{2-6}$ alkenyl group, or $R^4$ and $R^5$ form together with the adjacent nitrogen atom and optionally with one or more further nitrogen and/or oxygen and/or sulfur atom(s) a 5 to 10-membered saturated heterocyclic group optionally substituted by a $C_{1-4}$ alkyl group or a phenyl group which latter is optionally substituted by a $C_{1-4}$ alkoxy group, Z stands for a hydrogen atom or a $C_{1-4}$ alkoxy group, one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl ($C_{1-4}$ alkyl) group, or a pharmaceutically acceptable acid addition salt thereof as the active ingredient.

A still further subgroup of the pharmaceutical compositions of the invention contains a 5-(amino-alkoxyphenyl)-2-(1,2,4-triazole-1-yl)-1,3,4-thiadiazole derivative of the formula Ib
wherein
    one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group and a halophenyl ($C_{1-4}$ alkyl) group, Alk means a $C_{1-6}$ alkylene group, $R^4$ and $R^5$ represent, independently, a hydrogen atom or a $C_{1-8}$ alkyl group optionally substituted by a substituent selected from the group consisting of a hydroxy group, a ($C_{1-4}$ alkyl)amino group, a di-($C_{1-4}$ alkyl)amino group, a phenyl group—wherein the latter can be substituted by 1 to 3 $C_{1-4}$ alkoxy group(s)—and a 5- or 6-membered saturated heterocyclic group containing one or more nitrogen atom(s) or a nitrogen and an oxygen atom and being linked through its nitrogen atom, said heterocyclic group being optionally substituted by a $C_{1-4}$ alkyl group, or a pharmaceutically acceptable acid addition salt thereof as the active ingredient.

A preferred pharmaceutical composition of the invention contains a 2-(1,2,4-triazole-1-yl)-1,3,4-thiadiazole derivative of the formula I, wherein
    $R^1$ represents a hydrogen atom, a methyl group, an ethyl group or a phenyl group optionally substituted by 1 to 3 substituent(s) selected from the group consisting of a halo atom, a hN,ydroxy group, a nitro group, a methoxy group and a dimethylamino group, $R^2$ stands for an amino group optionally substituted by a halobenzyl group, $R^3$ means a piperidine-1-yl, piperazine-1-yl, morpholine-1-yl or 4-methylpiperazine-1-yl group or a group of the formula —SR, wherein R is a methyl group, or a pharmaceutically acceptable acid addition salt thereof as the active ingredient.

Suitably, the pharmaceutical composition of the invention contains a 5-phenyl-2-(1,2,4-triazole-1-yl)-1,3,4-thiadiazole derivative of the formula Ia,
wherein
    $R^0$ represents a group of the formula Alk-$NR^4R^5$,
    wherein
        Alk stands for an ethylene group or a propylene group,
        $R^4$ and $R^5$ mean, independently, a $C_{1-3}$ alkyl group, or
        $R^4$ and $R^5$ form together with the adjacent nitrogen atom a pyrrolidinyl group, $R^2$ is an amino group, $R^3$ stands for an amino group or a piperidinyl or 4-methylpiperazinyl group, said groups being linked through the nitrogen atom, or a group of the formula —SR, wherein R is a $C_{1-3}$ alkyl group, and optionally the amino group is substituted by two methyl groups or two allyl groups, Z represents a hydrogen atom, or a pharmaceutically acceptable acid addition salt thereof as the active ingredient.

Another preferred pharmaceutical composition of the invention contains a 5-(aminoalkoxyphenyl)-2-(1,2,4-triazole-1-yl)-1,3,4-thiadiazole derivative of the formula Ib, wherein
    $R^4$ represents a hydrogen atom or a $C_{1-2}$ alkyl group,
    $R^5$ stands for an ethyl group substituted by a substituent selected from the group consisting of hydroxy group, dimethoxy phenyl group and morpholino group,
    $R^2$ is an amino group,
    $R^3$ means a piperidyl group or a group of the formula —SR, wherein
        R stands for a $C_{1-3}$ alkyl group,
Alk represents a $C_{2-3}$ alkylene group,
or a pharmaceutically acceptable acid addition salt thereof as the active ingredient.

An especially preferred pharmaceutical composition of the invention contains any of the following compounds:

2-/5-amino-3-(4-methylpiperazino)-1H-1,2,4-triazole-1-yl/-5-(2,6-dichloro-phenyl)-1,3,4-thiadiazole, 2-(5-amino-3-methylthio-1H-1,2,4-triazole-1-yl)-5-/3-(3-dimethylaminopropoxy)phenyl/-1,3,4-thiadiazole, 2-(5-amino-3-dimethylamino-1H-1,2,4-triazole-1-yl)-5-/2-(3-dimethylaminopropoxy)phenyl/-1,3,4-thiadiazole, 2-/5-amino-3-(2-methylethylthio)-1H-1,2,4-triazole-1-yl/-5-/2-(3-dimethylaminopropoxy)phenyl/-1,3,4-thiadiazole, 2-(5-amino-3-piperidino-1H-1,2,4-triazole-1-yl)-5-/2-(3-dimethylaminopropoxy)phenyl/-1,3,4-thiadiazole, 2-(5-amino-3-methylthio-1H-1,2,4-triazole-1-yl)-5-/4-(2-dimethylaminoethoxy)phenyl/-1,3,4-thiadiazole, 2-(5-amino-3-methylthio-1H-1,2,4-triazole-1-yl)-5-/2-(3-pyrrolidinopropoxy)phenyl/-1,3,4-thiadiazole, 2-(5-amino-3-methylthio-1H-1,2,4-triazole-1-yl)-5-[2-/3-di(2-methylethyl)aminopropoxy/-phenyl]-1,3,4-thiadiazole, 2-/5-amino-3-(4-methylpiperazine-1-yl)-1H-1,2,4-triazole-1-yl/-5-/4-(3-dimethylaminopropoxy)phenyl/-1,3,4-thiadiazole, 2-(5-amino-3-diallylamino-1H-1,2,4-triazole-1-yl)-5-/2-(3-dimethylaminopropoxy)phenyl/-1,3,4-thiadiazole, 2-(5-amino-3-pyrrolidino-1H-1,2,4-triazole-1-yl)-5-/2-(3-dimethylaminopropoxy)phenyl/-1,3,4-thiadiazole, 2-(5-amino-3-piperidino-1H-1,2,4-triazole-1-yl)-5-{2-[2-/2-ethyl-2-(2-hydroxyethyl)amino/ethoxy]phenyl}-1,3,4-thiadiazole, 2-(5-amino-3-piperidino-1H-1,2,4-triazole-1-yl)-5-[-2-/2-(2-morpholinoethyl)amino/ethoxy]phenyl-1,3,4-thiadiazole, 2-(5-amino-3-methylthio-1H-1,2,4-triazole-1-yl)-5-{2-[3-methyl-3-/2-(3,4-dimethoxyphenylethyl)amino/propoxy]phenyl}-1,3,4-thiadiazole, 2-(5-amino-3-piperidino-1H-1,2,4-triazole-1-yl)-5-{2-[3-methyl-3-/2-(3,4-dimethoxyphenylethyl)amino/propoxy]phenyl}-1,3,4-thiadiazole, 2-/5-amino-3-(1-methylethylthio)-1H-1,2,4-triazole-1-yl/-5-{2-[3-methyl-3-/2-(3,4-dimethoxyphenylethyl)amino/propoxy]-phenyl}-1,3,4-thiadiazole, 2-(5-amino-3-methylthio-1H-1,2,4-triazole-1-yl)-5-{3-[3-methyl-3-/2-(3,4-dimethoxyphenylethyl)amino/propoxy]phenyl}-1,3,4-thiadiazole, 2-(5-amino-3-methylthio-1H-1,2,4-triazole-1-yl)-5-{4-[3-methyl-3-/2-(3,4-dimethoxyphenylethyl)amino/propoxy]phenyl}-1,3,4-thiadiazole, or a pharmaceutically acceptable acid addition salt thereof as the active ingredient.

Furthermore, the invention refers to a method of pharmaceutical treatment which comprises administering a therapeutically effective non-toxic amount of a 2-(1,2,4-triazole-1-yl)-1,3,4-thiadiazole derivative of the formula I or a pharmaceutically acceptable acid addition salt thereof to a patient suffering from a disease of especially the heart and/or the circulatory system or that of the central nervous system.

The invention is further elucidated, in detail, by means of the following Examples.

PREPARATION OF THE STARTING COMPOUNDS OF THE FORMULA II 1) 1-(5-Amino-3-piperidino-1H-1,2,4-triazole-1-yl)-N'-(2-hydroxybenzylidene)carbothiohydrazide 2.72 ml (0.026 moles) of salicylaldehyde are added to a suspension of 4.83 g (0.02 moles) of 1-(5-amino-3-piperidino-1,2,4-triazole-1-yl)thiohydrazide in 20 ml of methanol, and the reaction mixture is stirred for 4 days. The crystals are filtered, washed with some methanol, chloroform, then with tetrahydrofuran.

Thus, 5.94 g (86.1%) of the title compound are obtained, m.p.: 170–175° C.

2) 1-(5-Amino-3-methylthio-1H-1,2,4-triazole-1-yl)-N'-(2-hydroxybenzylidene)-carbothiohydrazide 2.3 ml (0.022 moles) of salicylaldehyde are added to a suspension of 4.08 g (0.02 moles) of 1-(5-amino-3-methylthio-1,2,4-triazole-1-yl)thiohydrazide in 20 ml of methanol, and the reaction mixture is stirred for 16 hours. The crystals are filtered, and washed with some methanol.

Thus, 5.48 g (88.8%) of the title compound are obtained, m.p.: 180–183° C.

3) 1-(5-Amino-3-propylthio-1H-1,2,4-triazole-1-yl)-N'-(2-hydroxybenzylidene)-carbothiohydrazide 2.69 g (0.022 moles) of salicylaldehyde are added to a suspension of 4.65 g (0.02 moles) of 1-(5-amino-3-propylthio-1,2,4-triazole-1-yl)thiohydrazide in 25 ml of methanol, and the reaction mixture is stirred at room temperature for 8 hours. The crystals are filtered, and washed with some methanol.

Thus, 6.65 g (98.8%) of the title compound are obtained, m.p.: 178–181° C.

4) 1-(5-Amino-3-allylthio-1H-1,2,4-triazole-1-yl)-N'-(2-hydroxybenzylidene)-carbothiohydrazide 1.10 g (0.009 moles) of salicylaldehyde are added to a suspension of 1.84 g (0.008 moles) of 1-(5-amino-3-allylthio-1,2,4-triazole-1-yl)thiohydrazide in 15 ml of methanol, and the reaction mixture is stirred at room temperature for 4 hours. The crystals are filtered, and washed with some methanol.

Thus, 2.53 g (94.5%) of the title compound are obtained, m.p.: 171–174° C.

5) 1-(5-Amino-3-benzylthio-1H-1,2,4-triazole-1-yl)-N'-(2-hydroxybenzylidene)-carbothiohydrazide 1.34 g (0.011 moles) of salicylaldehyde are added to a suspension of 2.8 g (0.01 moles) of 1-(5-amino-3-benzylthio-1,2,4-triazole-1-yl)thiohydrazide in 10 ml of methanol, and the reaction mixture is stirred at room temperature for 24 hours. The crystals are filtered, and washed with some methanol.

Thus, 3.34 g (87.0%) of the title compound are obtained, m.p.: 164–167° C.

6) 1-(5-Amino-3-morpholino-1H-1,2,4-triazole-1-yl)-N'-(2-hydroxybenzylidene)-carbothiohydrazide 1.34 g (0.011 moles) of salicylaldehyde are added to a suspension of 2.43 g (0.01 moles) of 1-(5-amino-3-morpholino-1,2,4-triazole-1-yl)thiohydrazide in 20 ml of methanol, and the reaction mixture is stirred at room temperature for 17 hours. The crystals are filtered, and washed with some methanol.

Thus, 3.2 g (92.2%) of the title compound are obtained, m.p.: 183–186° C.

7) 1-/5-Amino-3-(4-methylpiperazino)-1H-1,2,4-triazole-1-yl/-N'-(2-hydroxybenzylidene)carbothiohydrazide 2.68 g (0.022 moles) of salicylaldehyde are added to a suspension of 5.13 g (0.02 moles) of 1-/5-amino-3-(4-methylpiperazino)-1,2,4-triazole-1-yl/thiohydrazide in 40 ml of methanol, and the reaction mixture is stirred at room temperature for 24 hours. The crystals are filtered, and washed with some methanol.

Thus, 6.35 g (88.0%) of the title compound are obtained, m.p.: 176–179° C.

8) 1-(5-Amino-3-propargylthio-1H-1,2,4-triazole-1-yl)-N'-(2-hydroxybenzylidene)-carbothiohydrazide 1.34 g (0.011 moles) of salicylaldehyde are added to a suspension of 2.28 g (0.01 moles) of 1-(5-amino-3-propargylthio- 1,2,4-triazole-1-yl)thiohydrazide in 10 ml of methanol, and the reaction mixture is stirred at room temperature for 24 hours. The crystals are filtered, and washed with some methanol.

Thus, 3.14 g (94.6%) of the title compound are obtained, m.p.: 177–180° C.

9) 1-/5-Amino-3-(n-hexylthio)-1H-1,2,4-triazole-1-yl/-N'-(2-hydroxybenzylidene)-carbothiohydrazide 0.77 g (0.006 moles) of salicylaldehyde are added to a suspension of 1.37 g (0.005 moles) of 1-/(5-amino-3-(n-hexylthio)-1,2,4-triazole-1-yl/thiohydrazide in 10 ml of methanol, and the reaction mixture is stirred at room temperature for 20 hours. The crystals are filtered, and washed with some methanol.

Thus, 1.76 g (93.1%) of the title compound are obtained, m.p.: 158–160° C.

10) 1-(5-Amino-3-piperidino-1H-1,2,4-triazole-1-yl)-N'-/4-(2-bromoethoxy)benzylidene/-carbothiohydrazide 2.41 g (0.0105 moles) of 4-(2-bromoethoxy)benzaldehyde are added to a solution of 2.41 g (0.01 moles) of (5-amino-3-piperidino-1H-1,2,4-triazole-1-yl)carbothiohydrazide in 13.5 ml of chloroform and 1.5 ml of methanol. The reaction mixture is stirred at room temperature for 22 hours, filtered, and the product on the filter is washed with chloroform. The filtrate is evaporated to dryness under reduced pressure, and the residue is subjected to chromatography on Kieselgel 60 H. The fractions containing the desired product are evaporated.

11) 1-(5-Amino-3-piperidino-1H-1,2,4-triazole-1-yl)-N'-/2-(3-bromopropoxy)benzylidene/-carbothiohydrazide 9.72 g (0.04 moles) of 2-(3-bromopropoxy)benzaldehyde are added to a solution of 6.36 g (0.0263 moles) of (5-amino-3-piperidino-1H-1,2,4-triazole-1-yl)carbothiohydrazide in 100 ml of methanol. The reaction mixture is stirred at room temperature for 22 hours. The precipitated crystals are filtered, washed with methanol and ether.

Thus, 11.8 g (96.2%) of the title compound are obtained, m.p.: 167–168° C.

12) 1-(5-Amino-3-piperidino-1H-1,2,4-triazole-1-yl)-N'-/2-(2-bromoethoxy)benzylidene/-carbothiohydrazide 24.05 g (0.105 moles) of 2-(2-bromoethoxy)benzaldehyde are added to a solution of 24.1 g (0.1 moles) of (5-amino-3-piperidino-1H-1,2,4-triazole-1-yl)carbothiohydrazide in 150 ml of methanol. The reaction mixture is stirred at room temperature for 27 hours. The precipitated crystals are filtered, washed with methanol and tetrahydrofuran.

Thus, 30.2 g (66.8%) of the title compound are obtained, m.p.: 150–160° C. (decomposition; after recrystallization from acetonitrile).

13) 1-(5-Amino-3-piperidino-1H-1,2,4-triazole-1-yl)-N'-/3-(2-bromoethoxy)benzylidene/-carbothiohydrazide 24.1 g (0.105 moles) of 3-(2-bromoethoxy)benzaldehyde are added to a solution of 24.13 g (0.1 moles) of (5-amino-3-piperidino-1H-1,2,4-triazole-1-yl)carbothiohydrazide in 150 ml of ethanol. The reaction mixture is stirred at room temperature for 17 hours. The precipitated crystals are filtered, washed with methanol and tetrahydrofuran.

Thus, 34.0 g (75.2%) of the title compound are obtained, m.p.: 173–176° C. (decomposition; after recrystallization from acetonitrile).

14) 1-(5-Amino-3-piperidino)-1H-1,2,4-triazole-1-yl)-N'-/2-(4-bromobutoxy)benzylidene/carbothiohydrazide 14.01 g (0.0545 moles) of 2-(4-bromobutoxy)benzaldehyde are added to a solution of 12.07 g (0.05 moles) of (5-amino-3-piperidino-1H-1,2,4-triazole-1-yl)carbothiohydrazide in 72 ml of chloroform and 8 ml of methanol. The reaction-mixture is stirred at room temperature for 18 hours, then evaporated to dryness. The residue is subjected to chromatography on Kieselgel 60 H. The fractions containing the desired product are evaporated.

Thus, 11.5 g (47.9%) of the title compound are obtained, m.p.: 130–133° C. (decomposition).

15) 1-(5-Amino-3-piperidino-1H-1,2,4-triazole-1-yl)-N'-/2-(3-bromopropoxy-3-methoxy)benzylidene/carbohydrazide 9.83 g (0.036 moles) of 2-(3-bromopropoxy)-3-methoxybenzaldehyde are added to a solution of 7.24 g (0.03 moles) of (5-amino-3-piperidino-1H-1,2,4-triazole-1-yl)carbothiohydrazide in 60 ml of methanol. The reaction mixture is stirred at room temperature for 48 hours. The precipitated crystals are filtered, washed with methanol and ether.

Thus, 13.87 g (93.1%) of the title compound are obtained, m.p.: 149–152° C.

16) 1-(5-Amino-3-methylthio-1H-1,2,4-triazole-1-yl)-N'-/2-(3-bromopropoxy)benzylidene/-carbothiohydrazide 3.65 g (0.015 moles) of 2-(3-bromopropoxy)benzaldehyde are added to a solution of 2.04 g (0.01 moles) of (5-amino-3-methylthio-1H-1,2,4-triazole-1-yl)carbothiohydrazide in 50 ml of methanol. The reaction mixture is stirred at room temperature for 22 hours. The precipitated crystals are filtered, washed with methanol and ether.

Thus, 4.0 g (93.1%) of the title compound are obtained, m.p.: 157–159° C. (decomposition).

17) 1-/5-Amino-3-(2-methylethylthio)-1H-1,2,4-triazole-1-yl/-N'-/2-(3-bromopropoxy)benzylidene/carbothiohydrazide 30.6 g (0.125 moles) of 2-(3-bromopropoxy)benzaldehyde are added to a solution of 23.2 g (0.1 moles) of /5-amino-3-(2-methylethylthio)-1H-1,2,4-triazole-1-yl/-carbothiohydrazide in 30 ml of methanol. The reaction mixture is stirred at room temperature for 2.5 hours. The precipitated crystals are filtered, washed with methanol and ether.

Thus, 38.4 g (84.0%) of the title compound are obtained, m.p.: 136–139° C.

18) 1-(5-Amino-3-methylthio-1H-1,2,4-triazole-1-yl)-N'-/3-(3-bromopropoxy)benzylidene/-carbothiohydrazide 35.8 g (0.147 moles) of 3-(3-bromopropoxy)benzaldehyde are added to a solution of 20.4 g (0.1 moles) of (5-amino-3-methylthio-1H-1,2,4-triazole-1-yl)carbothiohydrazide in 500 ml of methanol. The reaction mixture is stirred at room temperature for 16 hours. The precipitated crystals are filtered, washed with methanol and ether.

Thus, 36.3 g (84.5%) of the title compound are obtained, m.p.: 134–135° C.

19) 1-(5-Amino-3-methylthio-1H-1,2,4-triazole-1-yl)-N'-/4-(3-bromopropoxy)benzylidene/-carbothiohydrazide 35.8 g (0.147 moles) of 4-(3-bromopropoxy)benzaldehyde are added to a solution of 20.4 g (0.1 moles) of (5-amino-3-methylthio-1H-1,2,4-triazole-1-yl)carbothiohydrazide in 500 ml of methanol. The reaction mixture is stirred at room temperature for 16 hours. The precipitated crystals are filtered, washed with methanol and ether.

Thus, 42.0 g (97.8%) of the title compound are obtained, m.p.: 135–137° C.

20) 1-/5-Amino-3-(2-methylethylthio)-1H-1,2,4-triazole-1-yl/-N'-/3-(3-bromopropoxy)benzylidene/carbothiohydrazide 15.3 g (0.067 moles) of 3-(3-bromopropoxy)benzaldehyde are added to a solution of 11.6 g (0.05 moles) of /5-amino-3-(2-methylethylthio)-1H-1,2,4-triazole-1-yl/- carbothiohydrazide in 180 ml of methanol. The reaction mixture is stirred at room temperature for 2.5 hours. The precipitated crystals are filtered, washed with methanol and ether.

Thus, 20.6 g (90.0%) of the title compound are obtained, m.p.: 136–139° C.

21) 1-/5-Amino-3-(2-methylethylthio)-1H-1,2,4-triazole-1-yl/-N'-/4-(3-bromopropoxy)benzylidene/carbothiohydrazide 15.3 g (0.067 moles) of 4-(3-bromopropoxy)benzaldehyde are added to a solution of 11.6 g (0.05 moles) of /5-amino-3-(2-methylethylthio)-1H-1,2,4-triazole-1-yl/-carbothiohydrazide in 180 ml of methanol. The reaction mixture is stirred at room temperature for 2.5 hours. The precipitated crystals are filtered, washed with methanol and ether.

Thus, 20.7 g (90.5%) of the title compound are obtained, m.p.: 132–135° C.

22) 1-/5-Benzylamino-3-(2-methylethylthio)-1H-1,2,4-triazole-1-yl/-N'-/2-(3-bromopropoxy)benzylidene/carbothiohydrazide 2.80 g (0.012 moles) of 2-(3-bromopropoxy)benzaldehyde are added to a solution of 3.22 g (0.01 moles) of /5-benzylamino-3-(2-methylethylthio)-1H-1,2,4-triazole-1-yl/-carbothiohydrazide in 25 ml of methanol. The reaction mixture is stirred at room temperature for 2 hours. The precipitated crystals are filtered, washed with methanol and cyclohexane.

Thus, 4.01 g (73.4%) of the title compound are obtained, m.p.: 110–112° C.

23) 1-/5-(4-Chlorobenzylamino)-3-(2-methylethylthio)-1H-1,2,4-triazole-1-yl/-N'-/2-(3-bromopropoxy)benzylidene/carbothiohydrazide 2.80 g (0.012 moles) of 2-(3-bromopropoxy)benzaldehyde are added to a solution of 3.57 g (0.01 moles) of /5-(4-chlorobenzylamino)-3-(2-methylethylthio)-1H-1,2,4-triazole-1-yl/carbothiohydrazide in 25 ml of methanol. The reaction mixture is stirred at room temperature for 3 hours. The precipitated crystals are filtered, washed with methanol and cyclohexane.

Thus, 4.70 g (81.1%) of the title compound are obtained, m.p.: 109–111° C.

PREPARATION OF THE STARTING COMPOUNDS OF THE FORMULA IX

24) 2-(5-Amino-3-piperidino-1H-1,2,4-triazole-1-yl)-5-/4-(2-bromoethoxy)phenyl/-1,3,4-thiadiazole To a suspension of 2.71 g (0.006 moles) of 1-(5-amino-3-piperidino-1H-1,2,4-triazole-1-yl)-N'-/4-(2-bromoethoxy)benzylidene/carbothiohydrazide in 20 ml of tetrahydrofuran, 1.5 g (0.066 moles) of DDQ are added under stirring and cooling at 25° C., whereupon the suspension is stirred at room temperature for further 2 hours. The tetrahydrofuran is removed from the reaction mixture under reduced pressure. To the residue, 30 ml of 5% aqueous sodium hydroxide solution are added, and the mixture is stirred for an hour. The precipitated product is feltered, washed first with a 5% aqueous sodium hydroxide solution and thereafter with water several times until neutral.

Thus, 2.56 g (94.7%) of the title compound are obtained. After chromatography on Kieselgel 60 H and recrystallization from acetonitrile, the product melts at 229–235° C. (decomposition).

25) 2-(5-Amino-3-piperidino-1H-1,2,4-triazole-1-yl)-5-/2-(3-bromopropoxy)phenyl/-1,3,4-thiadiazole To a suspension of 11.5 g (0.0246 moles) of 1-(5-amino-3-piperidino-1H-1,2,4-triazole-1-yl)-N'-/2-(3-bromopropoxy)benzylidene/carbothiohydrazide in 75 ml of tetrahydrofuran, 6.43 g (0.028 moles) of DDQ are added under stirring and cooling at 25° C., whereupon the suspension is stirred at room temperature for further 12 hours. The tetrahydrofuran is removed from the reaction mixture under reduced pressure. To the residue, 20 ml of 5% aqueous sodium hydroxide solution are added, and the mixture is stirred for an hour. The precipitated product is filtered, washed first with a 5% aqueous sodium hydroxide solution and thereafter with water several times until neutral.

Thus, 9.36 g (81.9%) of the title compound are obtained. After chromatography on Kieselgel 60 H and recrystallization from acetonitrile, the product melts at 192–195° C.

26) 2-(5-Amino-3-piperidino-1H-1,2,4-triazole-1-yl)-5-/2-(2-bromoethoxy)phenyl/-1,3,4-thiadiazole To a suspension of 3.62 g (0.008 moles) of 1-(5-amino-3-piperidino-1H-1,2,4-triazole-1-yl)-N'-/2-(2-bromoethoxy)benzylidene/carbothiohydrazide in 25 ml of tetrahydrofuran, 2.04 g (0.009 moles) of DDQ are added under stirring and cooling at 25° C., whereupon the suspension is stirred at room temperature for further 2 hours. The tetrahydrofuran is removed from the reaction mixture under reduced pressure. To the residue, 30 ml of 5% aqueous sodium hydroxide solution are added, and the mixture is stirred for an hour. The precipitated product is filtered, washed first with a 5% aqueous sodium hydroxide solution and thereafter with water several times until neutral.

Thus, 3.25 g (90.2%) of the title compound are obtained. The product is purified by chromatography on Kieselgel 60 H and recrystallization from acetonitrile. M.p.: 200–203° C. (decomposition).

27) 2-(5-Amino-3-piperidino-1H-1,2,4-triazole-1-yl)-5-/3-(2-bromoethoxy)phenyl/-1,3,4-thiadiazole To a suspension of 40.7 g (0.09 moles) of 1-(5-amino-3-piperidino-1H-1,2,4-triazole-1-yl)-N'-/3-(2-bromoethoxy)benzylidene/carbothiohydrazide in 400 ml of tetrahydrofuran, 22.7 g (0.1 moles) of DDQ are added under stirring and cooling at 25° C., whereupon the suspension is stirred at room temperature for further 2 hours. The tetrahydrofuran is removed from the reaction mixture under reduced pressure. To the residue, 30 ml of 5% aqueous sodium hydroxide solution are added. The precipitated product is filtered, washed first with a 5% aqueous sodium hydroxide solution and thereafter several times with water until neutral.

Thus, 38.6 g (94.8%) of the title compound are obtained. The product is purified by chromatography on Kieselgel 60 H and recrystallization from a 2:1 mixture of chloroform and methanol. M.p.: 175–178° C. (decomposition).

28) 2-(5-Amino-3-piperidino-1H-1,2,4-triazole-1-yl)-5-/2-(4-bromobutoxy) phenyl/-1,3,4-thiadiazole To a suspension of 11.53 g (0.024 moles) of 1-(5-amino-3-piperidino-1H-1,2,4-triazole-1-yl)-N'-/2-(4-bromobutoxy)benzylidene/carbothiohydrazide in 50 ml of tetrahydrofuran, 5.99 g (0.264 moles) of DDQ are added under stirring and cooling at 25° C., whereupon the suspension is stirred at room temperature for further 2 hours. The tetrahydrofuran is removed from the reaction mixture under reduced pressure. To the residue, 30 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 10.3 g (89.7%) of the title compound are obtained. The product is purified by chromatography on Kieselgel 60 H and recrystallization from a 1:1 mixture of acetonitrile and tetrahydrofuran. M.p.: 209–212° C.

29) 2-(5-Amino-3-piperidino-1H-1,2,4-triazole-1-yl)-5-/2-(3-bromopropoxy)-3-methoxyphenyl/-1,3,4-thiadiazole To a suspension of 13.4 g (0.027 moles) of 1-(5-amino-3-piperidino-1H-1,2,4-triazole-1-yl)-N'-/2-(3-bromopropoxy)-3-methoxybenzylidene/carbothiohydrazide in 70 ml of tetrahydrofuran, 6.81 g (0.03 moles) of DDQ are added under stirring and cooling at 25° C., whereupon the suspension is stirred at room temperature for further 20 hours. The tetrahydrofuran is removed from the reaction mixture under reduced pressure. To the residue, 20 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 13.1 g (98%) of the title compound are obtained. The product is purified by chromatography on Kieselgel 60 H, evaporation of the fractions containing the desired product, suspending the residue in acetonitrile, filtration and recrystallization from tetrahydrofuran. M.p.: 199–205° C. (decomposition).

30) 2-(5-Amino-3-methylthio-1H-1,2,4-triazole-1-yl)-5-/2-(3-bromopropoxy)phenyl/-1,3,4-thiadiazole To a suspension of 7.3 g (0.017 moles) of 1-(5-amino-3-methylthio-1H-1,2,4-triazole-1-yl)-N'-/2-(3-bromopropoxy)benzylidene/carbothiohydrazide in 50 ml of tetrahydrofuran, 4.36 g (0.019 moles) of DDQ are added under stirring and cooling at 25° C., whereupon the suspension is stirred at room temperature for further 2 hours. The tetrahydrofuran is removed from the reaction mixture under reduced pressure. To the residue, 20 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 6.37 g (87.6%) of the title compound are obtained. The product is purified by chromatography on Kieselgel 60 H and recrystallization from acetonitrile. M.p.: 209–212° C.

31) 2-/5-Amino-3-(methylethylthio)-1H-1,2,4-triazole-1-yl)-5-/2-(3-bromopropoxy)phenyl/-1,3,4-thiadiazole To a suspension of 37.38 g (0.0817 moles) of 1-(5-amino-3-methylethylthio)-1H-1,2,4-triazole-1-yl)-N'-/2-(3-bromopropoxy)benzylidene/carbothiohydrazide in 210 ml of tetrahydrofuran, 21.6 g (0.095 moles) of DDQ are added under stirring and cooling at 25° C., whereupon the suspension is stirred at room temperature for further 2 hours. The tetrahydrofuran is removed from the reaction mixture under reduced pressure. To the residue, 100 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 29.15 g 78.3%) of the title compound are obtained, m.p.: 183–185° C.

32) 2-(5-Amino-3-methylthio-1H-1,2,4-triazole-1-yl)-5-/3-(3-bromopropoxy)phenyl/-1,3,4-thiadiazole To a suspension of 35.8 g (0.0834 moles) of 1-(5-amino-3-methylthio-1H-1,2,4-triazole-1-yl)-N'-/3-(3-bromopropoxy)benzylidene/carbothiohydrazide in 350 ml of tetrahydrofuran, 21.4 g (0.094 moles) of DDQ are added under stirring and cooling at 25° C., whereupon the suspension is stirred at room temperature for further 2 hours. The tetrahydrofuran is removed from the reaction mixture under reduced pressure. To the residue, 100 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 24.5 g (67.7%) of the title compound are obtained, m.p.: 174–176° C.

33) 2-(5-Amino-3-methylthio-1H-1,2,4-triazole-1-yl)-5-/4-(3-bromopropoxy)phenyl/-1,3,4-thiadiazole To a suspension of 41.5 g (0.0967 moles) of 1-(5-amino-3-methylthio-1H-1,2,4-triazole-1-yl)-N'-/4-(3-bromopropoxy)benzylidene/carbothiohydrazide in 300 ml of tetrahydrofuran, 25.5 g (0.112 moles) of DDQ are added under stirring and cooling at 25° C., whereupon the suspension is stirred at room temperature for further 2 hours. The tetrahydrofuran is removed from the reaction mixture under reduced pressure. To the residue, 150 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 35.2 g (82.47%) of the title compound are obtained. After recrystallization from a mixture of dimethyl formamide and acetonitrile, m.p.: 219–222° C.

34) 2-/5-Amino-3-(2-methylethylthio)-1H-1,2,4-triazole-1-yl/-5-/3-(3-bromopropoxy)phenyl/-1,3,4-thiadiazole To a suspension of 20.0 g (0.0437 moles) of 1-/5-amino-3-(2-methylethylthio)-1H-1,2,4-triazole-1-yl/-N'-/3-(3-bromopropoxy)benzylidene/carbothiohydrazide in 115 ml of tetrahydrofuran, 11.59 g (0.051 moles) of DDQ are added under stirring and cooling at 25° C., whereupon the suspension is stirred at room temperature for further 2 hours. The tetrahydrofuran is removed from the reaction mixture under reduced pressure. To the residue, 100 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 14.4 g (72.4%) of the title compound are obtained, m.p.: 177–179° C.

35) 2-/5-Amino-3-(2-methylethylthio)-1H-1,2,4-triazole-1-yl/-5-/4-(3-bromopropoxy)phenyl/-1,3,4-thiadiazole To a suspension of 20.0 g (0.0437 moles) of 1-/5-amino-3-(2-methylethylthio)-1H-1,2,4-triazole-1-yl/-N'-/4-(3-bromopropoxy)benzylidene/carbothiohydrazide in 115 ml of tetrahydrofuran, 11.59 g (0.051 moles) of DDQ are added under stirring and cooling at 25° C., whereupon the suspension is stirred at room temperature for further 2 hours. The tetrahydrofuran is removed from the reaction mixture under reduced pressure. To the residue, 100 ml of 5% aqueous sodium hydroxide solution are added, and the mixture is stirred for an hour. The precipitated product is filtered, washed first with a 5% aqueous sodium hydroxide solution and thereafter several times with water until neutral.

Thus, 11.9 g (59.8%) of the title compound are obtained, m.p.: 190–191° C.

36) 2-(5-Amino-3-methylthio-1H-1,2,4-triazole-1-yl)-5-/4-(-3-bromopropoxy)phenyl/-1,3,4-thiadiazole To a suspension of 0.31 g (0.011 moles) of 2-(5-amino-3-methylthio-1H-1,2,4-triazole-1-yl)-N'-/5-(2-hydroxyphenyl)-1,3,4-thiadiazole in 10 ml of methanol, first 0.1 g (0.002 moles) of solid sodium methylate and thereafter 0.81 g (0.004 moles) of 1,3-dibromopropane are added. The suspension is heated to boiling for 24 hours, then cooled. The precipitated crystals are filtered, washed with cold methanol and ether.

Thus, 0.39 g (91.3%) of the title compound are obtained. After recrystallization from a mixture of dimethyl formamide and acetonitrile, m.p.: 218–221° C.

37) 2-(5-Amino-3-methylthio-1H-1,2,4-triazole-1-yl)-5-/2-(3-bromopropoxy)phenyl/-1,3,4-thiadiazole To a suspension of 14.0 g (0.045 moles) of 2-(5-amino-3-methylthio-1H-1,2,4-triazole-1-yl)-5-(2-hydroxyphenyl)-1,3,4-thiadiazole in 500 ml of methanol, 4.0 g (0.1 moles) of sodium hydroxide and 13.9 (0.05 moles) of tetrabutylammonium chloride are added. The solution thus obtained is evaporated to dryness, the residual crystalline substance is suspended in water, filtered, washed with water and ether.

Thus, 22.8 g (92.5%) of 2-(5-amino-3-methylthio-1H-1,2,4-triazole-1-yl)-5-(2-hydroxyphenyl)-1,3,4-thiadiazole tetrabutylammonium salt are obtained, m.p.: 194–196° C.

To 0.55 g (0.001 moles) of the above salt, 5 ml of acetonitrile and 0.81 g (0.004 moles) of 1,3-dibromopropane are added. The suspension is stirred at room temperature for 24 hours, the precipitated crystals are filtered, and washed with cold methanol and ether.

Thus, 0.41 g (96%) of the title compound are obtained. After recrystallization from a mixture of dimethyl formamide and acetonitrile m.p.: 219–221° C.

38) 2-/5-Amino-3-(n-hexylthio)-1H-1,2,4-triazole-1-yl/-5-/2-(3-bromopropoxy)phenyl/-1,3,4-thiadiazole 0.4 g (0.01 moles) of sodium hydroxide are dissolved in 5 ml of water, whereupon a solution of 0.68 g (0.002 moles) of tetrabutylammonium sulfate in 5 ml of water are added. To the reaction mixture, 15 ml of chloroform and 0.60 g (0.0016 moles) of 2-/5-amino-3-(n-hexylthio)-1H-1,2,4-triazole-1-yl/-5-(2-hydroxyphenyl)-1,3,4-thiadiazole are added. The reaction mixture is vigorously stirred for 5 minutes. The phases are separated, the aqueous layer is extracted with 10 ml of chloroform. The combined organic solutions are extracted with water, dried over anhydrous sodium sulfate, and evaporated to dryness. The residual crystalline substance is suspended in ether, filtered, and washed with ether.

Thus, 0.76 g (76.9%) of 2-/5-amino-3-(n-hexylthio)-1H-1,2,4-triazole-1-yl/-5-(2-hydroxyphenyl)-1,3,4-thiadiazole tetrabutylammonium salt are obtained, m.p.: 150–160° C.

To 0.62 g (0.001 moles) of 2-/5-amino-3-(n-hexylthio)-1H-1,2,4-triazole-1-yl/-5-(2-hydroxyphenyl)-1,3,4-thiadiazole tetrabutylammonium salt, 5 ml of acetonitrile and 0.81 g (0.004 moles) of 1,3-dibromopropane are added. The suspension is stirred at room temperature for 24 hours. The precipitated crystals are filtered, washed with cold methanol and ether.

Thus, 0.38 g (76.4%) of the title compound are obtained. After recrystallization from a mixture of dimethyl formamide and acetonitrile, m.p.: 180–186° C.

39) 2-/5-Benzylamino-3-(2-methylethylthio)-1H-1,2,4-triazole-1-yl/-5-/2-(3-bromopropoxy)phenyl/-1,3,4-thiadiazole To a freshly prepared suspension of 0.55 g (0.001 moles) of 1-/5-benzylamino-3-(2-methylethylthio)-1H-1,2,4-triazole-1-yl/-N'-/2-(3-bromopropoxy)benzylidene/carbothiohydrazide in 3 ml tetrahydrofurane, 0.27 g (0.001 moles) of DDQ are added under stirring and cooling at 25° C. The suspension is stirred at room temperature for a further period of 30 minutes. The tetrahydrofuran is removed under reduced pressure, to the residue, 5 ml of isopropanol are added, the mixture is thoroughly stirred, filtered, and washed several times with isopropanol and ether.

Thus, 0.46 g (84.3%) of the title compound are obtained, m.p.: 148–150° C.

40) 2-/5-(4-Chlorobenzylamino)-3-(2-methylethylthio)-1H-1,2,4-triazole-1-yl/-5-/2-(3-bromoprorpoxy)phenyl/-1,3,4-thiadiazole To a suspension of 0.58 g (0.001 moles) of 1-/5-(4-chlorobenzylamino)-3-(2-methylethylthio)-1H-1,2,4-triazole-1-yl/-N'-/2-(3-bromopropoxy)benzylidene/carbothiohydrazide in 3 ml of tetrahydrofuran, 0.27 g (0.001 moles) of DDQ are added under stirring and cooling at 25° C. The suspension is stirred at room temperature for a further period of 30 minutes, the tetrahydrofuran is removed under reduced pressure, the residue is subjected to chromatography on a Kieselgel 60 H column and eluted with mixtures of chloroform and cyclohexane using a gradient of increasing polarity. The fractions containing the desired compound are evaporated. The residue is dissolved in 5 ml of hot isopropanol and allowed to crystallize. The precipitated crystals are filtered, and washed with isopropanol and ether.

Thus, 0.40 g (70.2%) of the title compound are obtained, m.p.: 123–124° C.

41) 2-(5-Amino-3-propargylthio-1H-1,2,4-triazole-1-yl)-5-/2-(3-bromopropoxy)phenyl/-1,3,4-thiadiazole To a suspension of 1.98 g (0.006 moles) of 2-(5-Amino-3-propargylthio-1H-1,2,4-triazole-1-yl)-5-(2-hydroxyphenyl)-1,3,4-thiadiazole in 25 ml of chloroform, a solution of 0.84 g (0.021 moles) of sodium hydroxide in 10 ml of water, and thereafter a solution of 2.38 g (0.0072 moles) of tetrabutylammonium chloride in 10 ml of water are added. The reaction mixture is vigorously stirred for 20 minutes. The crystalline product is filtered and washed with water and ether.

Thus, 2.84 g (83%) of 2-(5-Amino-3-propargylthio-1H-1,2,4-triazole-1-yl)-5-(2-hydroxyphenyl)-1,3,4-thiadiazole tetrabutylammonium chloride are obtained, m.p.: 165–170° C.

To 2.29 g (0.004 moles) of the above salt, 2 ml of acetonitrile and 4.04 g (0.02 moles) of 1,3-dibromopropane are added. The suspension is stirred at room temperature for 24 hours. The precipitated crystals are filtered, washed with cold methanol and ether.

Thus, the title compound is obtained which is recrystallized from a mixture of dimethyl formamide and acetonitrile.

42) 2-(5-Amino-3-allylthio-1H-1,2,4-triazole-1-yl)-5-/2-(3-bromopropoxy)phenyl/-1,3,4-thiadiazole To a suspension of 1.66 g (0.005 moles) of 2-(5-Amino-3-allylthio-1H-1,2,4-triazole- 1-yl)-5-(2-hydroxyphenyl)-1,3,4-thiadiazole in 20 ml of chloroform, a solution of 0.84 g (0.021 moles) of sodium hydroxide in 10 ml of water, and thereafter a solution of 2.04 g (0.006 moles) of tetrabutylammonium chloride in 10 ml of water are added. The reaction mixture is vigorously stirred for 20 minutes. The crystalline product is filtered and washed with water and ether.

Thus, 2.04 g (74.8%) of 2-(5-Amino-3-allylthio-1H-1,2,4-triazole-1-yl)-5-(2-hydroxyphenyl)-1,3,4-thiadiazole tetrabutylammonium chloride are obtained, m.p.: 180–183° C.

To 2.01 g (0.0035 moles) of the above salt, 20 ml of acetonitrile and 3.03 g (0.15 moles) of 1,3-dibromopropane are added. The suspension is stirred at room temperature for 24 hours. The precipitated crystals are filtered, washed with cold methanol and ether.

Thus, 1.33 g (84.2%) of the title compound are obtained. After recrystallization from a mixture of dimethyl formamide and acetonitrile, 1.33 g of the desired product are obtained, m.p.: 178–180° C.

43) 2-(5-Amino-3-propylthio-1H-1,2,4-triazole-1-yl)-5-/2-(3-bromopropoxy)phenyl/-1,3,4-thiadiazole To a suspension of 1.34 g (0.004 moles) of 2-(5-Amino-3-propylthio-1H-1,2,4-triazole- 1-yl)-5-(2-hydroxyphenyl)-1,3,4-thiadiazole in 20 ml of chloroform, a solution of 0.60 g (0.015 moles) of sodium hydroxide in 10 ml of water, and thereafter a solution of 1.70 g (0.005 moles) of tetrabutylammonium chloride in 10 ml of water are added. The reaction mixture is vigorously stirred for 20 minutes. The crystalline product is filtered and washed with water and ether.

Thus, 1.30 g (56.5%) of 2-(5-Amino-3-propylthio-1H-1,2,4-triazole-1-yl)-5-(2-hydroxyphenyl)-1,3,4-thiadiazole tetrabutylanimonium chloride are obtained, m.p.: 195–198° C.

To 1.15 g (0.002 moles) of the above salt, 15 ml of acetonitrile and 2.02 g (0.01 moles) of 1,3-dibromopropane are added. The suspension is stirred at room temperature for 24 hours. The precipitated crystals are filtered, washed with cold methanol and ether.

Thus, 0.78 g (85.7%) of the title compound are obtained. After recrystallization from a mixture of dimethyl formamide and acetonitrile, m.p.: 178–180° C.

44) 2-(5-Amino-3-benzylthio-1H-1,2,4-triazole-1-yl)-5-/2-(3-bromopropoxy)phenyl/-1,3,4-thiadiazole To a suspension of 1.61 g (0.0042 moles) of 2-(5-Amino-3-benzylthio-1H-1,2,4-triazole-1-yl)-5-(2-hydroxyphenyl)-1,3,4-thiadiazole in 20 ml of chloroform, a solution of 0.48 g (0.012 moles) of sodium hydroxide in 10 ml of water, and thereafter a solution of 1.70 g (0.005 moles) of tetrabutylammonium chloride in 10 ml of water are added. The reaction mixture is vigorously stirred for 20 minutes. The crystalline product is filtered and washed with water and ether.

Thus, 2.00 g (64.3%) of 2-(5-Amino-3-benzylthio-1H-1,2,4-triazole-1-yl)-5-(2-hydroxyphenyl)-1,3,4-thiadiazole tetrabutylammonium chloride are obtained, m.p.: 170–174° C.

To 1.87 g (0.003 moles) of the above salt, 20 ml of acetonitrile and 2.42 g (0.012 moles) of 1,3-dibromopropane are added. The suspension is stirred at room temperature for 44 hours. The precipitated crystals are filtered, washed with cold methanol and ether.

Thus, 1.37 g (90.7%) of the title compound are obtained, m.p.: 175–180° C.

45) 2-(5-Amino-3-methylthio-1H-1,2,4-triazole-1-yl)-5-/2-(2-bromoethoxy)phenyl/-1,3,4-thiadiazole To 4.60 g (0.015 moles) of 2-(5-amino-3-methylthio-1H-1,2,4-triazole-1-yl)-5-(2-hydroxyphenyl)-1,3,4-thiadiazol, 20 ml of methanol and a solution of 1.08 g (0.002 moles) of sodium methylate in 10 ml of methanol are added. The reaction mixture is stirred for 10 minutes, whereupon it is evaporated to dryness. To the residue, 35 ml of dimethyl formamide and 12.27 g (0.06 moles) of 1,2-dibromoethane are added. The suspension is stirred at 80° C. for 18 hours, then cooled. The precipitated crystals are filtered, washed with cold methanol and ether.

Thus, 2.16 g (34.9%) of the title compound are obtained, m.p.: 227–229° C.

46) 2-(5-Amino-3-methylthio-1H-1,2,4-triazole-1-yl)-5-/2-(2-bromoethoxy)phenyl/-1,3,4-thiadiazole To 4.38 g (0.008 moles) of 2-(5-amino-3-methylthio-1H-1,2,4-triazole-1-yl)-5-(2-hydroxyphenyl)-1,3,4-thiadiazol tetrabutylammonium salt, 40 ml of acetonitrile and 6.01 g (0.032 moles) of 1,2-dibromoethane are added. The suspension is stirred at room temperature for 64 hours. The precipitated crystals are filtered, washed with cold methanol and ether.

Thus, 3.02 g (90.9%) of the title compound are obtained, m.p.: 227–228° C.

47) 2-(5-Amino-3-morpholino-1H-1,2,4-triazole-1-yl)-5-/2-(3-bromopropoxy)phenyl/-1,3,4-thiadiazole To 2.64 g (0.0045 moles) of 2-(5-amino-3-morpholino-1H-1,2,4-triazole-1-yl)-5-(2-hydroxyphenyl)-1,3,4-thiadiazol tetrabutylammonium salt, 20 ml of acetonitrile and 3.63 g (0.018 moles) of 1,3-dibromopropane are added. The suspension is stirred at room temperature for 26 hours. The precipitated crystals are filtered, washed with cold methanol and ether.

Thus, 1.85 g (88.1%) of the title compound are obtained. After recrystallization from a mixture of dimethyl formamide and acetonitrile, m.p.: 210–214° C.

PREPARATION OF THE COMPOUNDS OF THE FORMULA I

EXAMPLE 1

2-(5-Amino-3-methylthio-1H-1,2,4-triazole-1-yl)-5-(3,4,5-trimethoxyphenyl)-1,3,4-thiadiazole To a solution of 17.2 g (0.045 moles) of 1-(5-amino-3-methylthio-1H-1,2,4-triazole-1-yl)-N'-(3,4,5-trimethoxybenzylidene)carbothiohydrazide in 110 ml of acetic acid, a solution of 67.5 g of iron(III) chloride in 75 ml of water is added under stirring and cooling at 20° C. The reaction mixture is stirred at room temperature for 2 hours, then diluted with 800 ml of water, stirred for further 5 hours, and allowed to stand for a night. On the following day, the product precipitated is filtered.

Thus, 15.9 g (92.8%) of the title product are obtained. M.p. (after recrystallization from ethanol): 234–236° C.

EXAMPLE 2

2-(5-Amino-3-methylthio-1H-1,2,4-triazole-1-yl)-5-phenyl-1,3,4-thiadiazole

To a solution of 0.88 g (0.003 moles) of 1-(5-amino-3-methylthio-1H-1,2,4-triazole-1-yl)-N'-benzylidene-carbothiohydrazide in 7.5 ml of acetic acid, a solution of 4.5 g of iron(III) chloride in 5 ml of water is added under stirring and cooling at 20° C. The reaction mixture is stirred at room temperature for 2 hours, then diluted with 60 ml of water, stirred for further 5 hours, and allowed to stand for a night. On the following day, the product precipitated is filtered.

Thus, 0.47 g (54%) of the title product are obtained. M.p. (after recrystallization from isopropanol): 220–222° C.

EXAMPLE 3

2-(5-Amino-3-methylthio-1H-1,2,4-triazole-1-yl)-5-phenyl-1,3,4-thiadiazole

To a solution of 2.04 g (0.01 moles) of 1-(5-amino-3-methylthio-1H-1,2,4-triazole-1-yl)carbothiohydrazide in 50 ml of methanol, 3.4 ml (0.015 moles) of triethyl orthobenzoate are added, and the reaction mixture is boiled for 4 hours. On the next day, the crystals precipitated are filtered, washed with some methanol.

Thus, 0.95 g (32.8%) of the title compound are obtained. M.p. (after recrystallization from acetonitrile): 222–224° C.

EXAMPLE 4

2-(5-Amino-3-morpholino-1H-1,2,4-triazole-1-yl)-1,3,4-thiadiazole

To a solution of 14.58 g (0.06 moles) of 1-(5-amino-3-morpholino-1H-1,2,4-triazole-1-yl)carbothiohydrazide in 300 ml of methanol, 30 ml of triethyl orthoformate are added, and the reaction mixture is boiled for 8 hours. The crystals precipitated are filtered from the hot mixture, and washed with some methanol.

Thus, 10.4 g (68.4%) of the title compound are obtained. M.p. (after recrystallization from methanol): 203–205° C.

EXAMPLE 5

2-(5-Amino-3-methylthio-1H-1,2,4-triazole-1-yl)-1,3,4-thiadiazole

To a suspension of 10.2 g (0.05 moles) of 1-(5-amino-3-methylthio-1H-1,2,4-triazole-1-yl)carbothiohydrazide in 250 ml of methanol, 25 ml of triethyl orthoformate are added, and the reaction mixture is boiled for 4 hours. After cooling, the crystals precipitated are filtered, and washed with some methanol.

Thus, 8.8 g (82.1%) of the pure title compound are obtained. M.p.: 202–203° C.

EXAMPLE 6

2-(5-Amino-3-methylthio-1H-1,2,4-triazole-1-yl)-5-methyl-1,3,4-thiadiazole

To a suspension of 2.04 g (0.01 moles) of 1-(5-amino-3-methylthio-1H-1,2,4-triazole-1-yl)carbothiohydrazide in 50 ml of methanol, 5.7 ml of triethyl orthoacetate are added, and the reaction mixture is boiled for 8 hours. After cooling, the crystals precipitated are filtered, and washed with some methanol.

Thus, 1.05 g (46.0%) of the title compound are obtained. M.p. (after recrystallization from methanol): 191–193° C.

EXAMPLE 7

2-(5-Amino-3-methylthio-1H-1,2,4-triazole-1-yl)-5-ethyl-1,3,4-thiadiazole

To a suspension of 14.28 g (0.07 moles) of 1-(5-amino-3-methylthio-1H-1,2,4-triazole-1-yl)carbothiohydrazide in 200 ml of methanol, 80 ml of triethyl orthopropionate are added, and the reaction mixture is boiled for 8 hours. After cooling, the crystals precipitated are filtered, and washed with some methanol.

Thus, 9.42 g (55.5%) of the pure title compound are obtained. M.p.: 166–168° C.

EXAMPLE 8

2-(5-Amino-3-methylthio-1H-1,2,4-triazole-1-yl)-5-(4-dimethylaminophenyl)-1,3,4-thiadiazole To a suspension of 10.05 g (0.03 moles) of 1-(5-amino-3-methylthio-1H-1,2,4-triazole-1-yl)-N'-(4-dimethylaminobenzylidene)carbothiohydrazide in 32.5 ml of acetic acid, a solution of 19.5 g of iron(III) chloride in 22 ml of water is added under stirring and cooling at 20° C. The reaction mixture is stirred at room temperature for 2 hours, then diluted with 100 ml of water, stirred for a further hour, and allowed to stand for a night. On the following day, the product precipitated is filtered, and washed with some ethanol.

Thus, 8.9 g (89%) of the title product are obtained. M.p.: (after recrystallization from dimethylformamide): 292–294° C.

EXAMPLE 9

2-(5-Amino-3-methylthio-1H-1,2,4-triazole-1-yl)-5-(4-chlorophenyl)-1,3,4-thiadiazole To a suspension of 10.05 g (0.03 moles) of 1-(5-amino-3-methylthio-1H-1,2,4-triazole-1-yl)-N'-(4-chlorobenzylidene)carbothiohydrazide in 25 ml of acetic acid, a solution of 15 g of iron(III) chloride in 17 ml of water is added under stirring. The reaction mixture is boiled for 15 minutes, then diluted with 100 ml of water, stirred for a further hour, the product precipitated is filtered, and washed with some ethanol.

Thus, 2.71 g (83.4%) of the title product are obtained. M.p.: (after recrystallization from dimethylformamide): 269–271° C.

EXAMPLE 10

2-/5-Amino-3-(4-methylpiperazino)-1H-1,2,4-triazole-1-yl/-5-(2,6-dichlorophenyl)-1,3,4-thiadiazole hydrochloride monohydrate To a suspension of 2.07 g (0.005 moles) of 1-/5-amino-3-(4-methylpiperazino)-1H-1,2,4-triazole-1-yl)-N'-(2,6-dichlorobenzylidene)carbothiohydrazide in 12.5 ml of acetic acid, a solution of 7.5 g of iron(III) chloride in 8.5 ml of water is added under stirring. The reaction mixture is boiled for 1 hour, then diluted with 100 ml of water, stirred for a further hour, the product precipitated is filtered, and washed with some water, then with isopropanol.

Thus, 2.12 g (91.0%) of the title product are obtained. M.p.: (after recrystallization from methanol): 281–284° C.

EXAMPLE 11

2-/5-(4-Chlorobenzylamino)-3-methylthio-1H-1,2,4-triazole-1-yl/-1,3,4-thiadiazole To a suspension of 1.0 g (0.003 moles) of 1-/5-(4-chlorobenzylamino)-3-methylthio-1H-1,2,4-triazole-1-yl/ carbothiohydrazide in 20 ml of methanol, 4 ml of triethyl orthoformate are added, and the reaction mixture is boiled for 4 hours. After cooling, the crystals precipitated are filtered, and washed with some methanol.

Thus, 0.5 g (49.2%) of the title compound are obtained. M.p. (after recrystallization from methanol): 140–141° C.

EXAMPLE 12

2-(5-Amino-3-methylthio-1H-1,2,4-triazole-1-yl)-5-(4-nitrophenyl)-1,3,4-thiadiazole To a suspension of 3.37 g (0.01 moles) of 1-(5-amino-3-methylthio-1H-1,2,4-triazole-1-yl)-N'-(4-nitrobenzylidene)carbothiohydrazide in 25 ml of acetic acid, a solution of 15 g of iron(III) chloride in 17 ml of water is added under stirring. The reaction mixture is boiled for 2 hours, then diluted with 200 ml of water, stirred for a further hour, the product precipitated is filtered, and washed with some ethanol.

Thus, 2.44 g (72.8%) of the title product are obtained. M.p.: (after recrystallization from dimethylformamide): 301–303° C.

EXAMPLE 13

2-(5-Amino-3-methylthio-1H-1,2,4-triazole-1-yl)-5-(4-fluorophenyl)-1,3,4-thiadiazole To a suspension of 0.93 g (0.003 moles) of 1-(5-amino-3-methylthio-1H-1,2,4-triazole-1-yl)-N'-(4-fluorobenzylidene)carbothiohydrazide in 7.5 ml of acetic acid, a solution of 4.5 g of iron(III) chloride in 5.2 ml of water is added under stirring and cooling at 20° C. The reaction mixture is stirred for 2 hours, then diluted with 50 ml of water, stirred for a further hour, and allowed to stand for a night. On the following day, the product precipitated is filtered, and washed with some ethanol.

Thus, 0.75 g (81.0%)of the title product are obtained. M.p.: (after recrystallization from dimethylformamide): 246–247° C.

EXAMPLE 14

2-(5-Amino-3-piperidino-1H-1,2,4-triazole-1-yl)-5-(2-hydroxyphenyl)-1,3,4-thiadiazole To a suspension of 5.18 g (0.015 moles) of 1-(5-amino-3-piperidino-1H-1,2,4-triazole-1-yl)-N'-(2-hydroxybenzylidene)carbothiohydrazide in 30 ml of tetrahydrofuran, 3.75 g (0.0165 moles) of DDQ are added under stirring and cooling at 20° C. The suspension is stirred at room temperature for a further hour, the product precipitated is filtered, and washed with tetrahydrofuran.

Thus, 3.04 g (59.7%) of the pure title compound are obtained. M.p.: 268–272° C.

EXAMPLE 15

2-(5-Amino-3-methylthio-1H-1,2,4-triazole-1-yl)-5-(2-hydroxyphenyl)-1,3,4-thiadiazole To a suspension of 6.78 g (0.022 moles) of 1-(5-amino-3-methylthio-1H-1,2,4-triazole-1-yl)-N'-(2-hydroxybenzylidene)carbothiohydrazide in 50 ml of tetrahydrofuran, 5.49 g (0.0242 moles) of DDQ are added under stirring and cooling at 20° C. The suspension is stirred at room temperature for further 1.5 hours, the product precipitated is filtered, and washed with tetrahydrofuran.

Thus, 6.17 g (91.6%) of the pure title compound are obtained. M.p.: 304–306° C.

EXAMPLE 16

2-(5-Amino-3-propylthio-1H-1,2,4-triazole-1-yl)-5-(2-hydroxyphenyl)-1,3,4-thiadiazole To a suspension of 4.04 g (0.012 moles) of 1-(5-amino-3-propylthio-1H-1,2,4-triazole-1-yl)-N'-(2-hydroxybenzylidene)carbothiohydrazide in 20 ml of tetrahydrofuran, 2.95 g (0.013 moles) of DDQ are added under stirring and cooling at 20° C. The suspension is stirred at room temperature for a further hour, the product precipitated is filtered, and washed with tetrahydrofuran.

Thus, 1.82 g (45.3%) of the pure title compound are obtained. M.p.: 224–227° C. The mother liquor is evaporated to dryness, and the residue is suspended in isopropanol to obtain further 1.05 g (26.2%) of product that is identical with the title compound. M.p.: 221–225° C.

EXAMPLE 17

2-(5-Amino-3-allylthio-1H-1,2,4-triazole-1-yl)-5-(2-hydroxyphenyl)-1,3,4-thiadiazole To a suspension of 2.34 g (0.007 moles) of 1-(5-amino-3-allylthio-1H-1,2,4-triazole-1-yl)-N'-(2-hydroxybenzylidene)carbothiohydrazide in 20 ml of tetrahydrofuran, 1.82 g (0.008 moles) of DDQ are added under stirring and cooling at 20° C. The suspension is stirred at room temperature for a further hour, the product precipitated is filtered, washed with tetrahydrofuran and ether.

Thus, 1.8 g (77.3%) of the pure title compound are obtained. M.p.: 222–224° C. The mother liquor is evaporated to dryness, and the residue is suspended in isopropanol to obtain further 0.28 g (12.0%) of product that is identical with the title compound. M.p.: 222–223° C.

EXAMPLE 18

2-(5-Amino-3-benzylthio-1H-1,2,4-triazole-1-yl)-5-(2-hydroxyphenyl)-1,3,4-thiadiazole To a suspension of 3.08 g (0.008 moles) of 1-(5-amino-3-benzylthio-1H-1,2,4-triazole-1-yl)-N'-(2-hydroxybenzylidene)carbothiohydrazide in 15 ml of tetrahydrofuran, 2.04 g (0.009 moles) of DDQ are added under stirring and cooling at 20° C. The suspension is stirred at room temperature for a further hour, the product precipitated is filtered, and washed with tetrahydrofuran.

Thus, 1.12 g (36.6%) of the pure title compound are obtained. M.p.: 200–202° C. The mother liquor is evaporated to dryness, and the residue is suspended in isopropanol to obtain further 1.0 g (32.7%) of product that is identical with the title compound. M.p.: 198–201° C.

EXAMPLE 19

2-(5-Amino-3-morpholino-1H-1,2,4-triazole-1-yl)-5-(2-hydroxyphenyl)-1,3,4-thiadiazole To a suspension of 1.95 g (0.0085 moles) of 1-(5-amino-3-morpholino-1H-1,2,4-triazole-1-yl)-N'-(2- hydroxybenzylidene)carbothiohydrazide in 30 ml of tetrahydrofuran, 2.16 g (0.0095 moles) of DDQ are added under stirring and cooling at 20° C. The suspension is stirred at room temperature for a further hour, the product precipitated is filtered, and washed with tetrahydrofuran.

Thus, 2.4 g (81.9%) of the pure title compound are obtained. M.p.: 265–270° C.

EXAMPLE 20

2-/5-Amino-3-(4-methylpiperazino)-1H-1,2,4-triazol-1-yl/-5-(2-hydroxyphenyl)-1,3,4-thiadiazole To a suspension of 5.95 g (0.0165 moles) of 1-/5-amino-3-(4-methylpiperazino)-1H-1,2,4-triazol-1-yl/-N'-(2-hydroxybenzylidene)carbothiohydrazide in 60 ml of tetrahydrofuran, 4.09 g (0.018 moles) of DDQ are added under stirring and cooling at 20° C. The suspension is stirred at room temperature for a further hour, the product precipitated is filtered, and washed with tetrahydrofuran.

EXAMPLE 21

2-(5-Amino-3-propargylthio-1H-1,2,4-triazol-1-yl)-5-(2-hydroxyphenyl)-1,3,4-thiadiazole To a suspension of 2983 g (0.0085 moles) of 1-(5-amino-3-propargylthio-1H-1,2,4-triazol-1-yl)-N'-(2-hydroxybenzylidene)carbothiohydrazide in 30 ml of tetrahydrofuran, 2.13 g (0.0094 moles) of DDQ are added under stirring and cooling at 20° C. The suspension is stirred at room temperature for further 2 hours, the product precipitated is filtered, and washed with tetrahydrofuran.

Thus, 1.81 g (64.6%) of the pure title compound are obtained. M.p.: 236–240° C.

EXAMPLE 22

2-(5-Amino-3-n-hexylthio-1H-1,2,4-triazol-1-yl)-5-(2-hydroxyphenyl)-1,3,4-thiadiazole To a suspension of 1.59 g (0.0042 moles) of 1-(5-amino-3-n-hexylthio-1H-1,2,4-triazol-1-yl)-N'-(2-hydroxybenzylidene)carbothiohydrazide in 10 ml of tetrahydrofuran, 1.07 g (0.0047 moles) of DDQ are added under stirring and cooling at 20° C. The suspension is stirred at room temperature for further 2 hours, the product precipitated is filtered, and washed with tetrahydrofuran.

Thus, 1.01 g (63.9%) of the pure title compound are obtained. M.p.: 212–214° C.

EXAMPLE 23

2-(5-Amino-3-methylthio-1H-1,2,4-triazol-1-yl)-5-/2-(3-dimethylamino-2-methylpropoxy)phenyl/-1,3,4-thiadiazole dihydrochloride monohydrate 14.7 g (0.036 moles) of 1-(5-amino-3-methylthio-1H-1,2,4-triazol-1-yl)-N'-/2-(3-dimethylamino-2-methylpropoxy)benzylidene/carbothiohydrazide are dissolved in 40 ml of acetic acid at room temperature, to the solution 15 ml of methanol are added, and to the mixture obtained a solution of 43.2 g of iron(III) chloride in 40 ml of water are added at 25° C. under stirring and cooling. The reaction mixture is stirred at room temperature for 2 hours. The following day, the reaction mixture is evaporated to dryness under reduced pressure, to the residue 200 ml of ethanol are added, the product precipitated is filtered, and washed twice thoroughly with methanol.

Thus, 12.65 g (70.7%) of the title product are obtained. M.p.: (after recrystallization from water): 244–246° C.

EXAMPLE 24

2-(5-Amino-3-methylthio-1H-1,2,4-triazol-1-yl)-5-/2-(3-dimethylaminopropoxy)phenyl/-1,3,4-thiadiazole hydrochloride To a solution of 17.95 g (0.0455 moles) of 1-(5-amino-3-methylthio-1H-1,2,4-triazol-1-yl)-N'-/2-(3-dimethylaminopropoxy)benzylidene/carbothiohydrazide in 50 ml of acetic acid, a solution of 35 g (0.216 moles) of iron(III) chloride in 35 ml of water is added at 35° C. under stirring, then the reaction mixture is stirred at room temperature for 2 hours. The thick reaction mixture is diluted with 10 ml of water, stirred for a further hour, then allowed to stand for a night. On the other day, the product precipitated is filtered.

Thus, 15.2 g (78.0%) of the title compound are obtained. M.p.: (after recrystallization from water): 250–252° C.

EXAMPLE 25

2-(5-Amino-3-methylthio-1H-1,2,4-triazol-1-yl)-5-/2-(3-dimethylaminopropoxy)phenyl/-1,3,4-thiadiazole To a suspension of 13.6 g (0.0345 moles) of 1-(5-amino-3-methylthio-1H-1,2,4-triazol-1-yl)-N'-/2-(3-dimethylaminopropoxy)benzylidene/carbothiohydrazide in 100 ml of tetrahydrofuran, 9.53 g (0.042 moles) of DDQ are added at 25° C. under stirring and cooling, then the suspension is stirred at room temperature for further 6 hours. To the reaction mixture, 300 ml of 5% aqueous sodium hydroxide solution are added, and stirred for further half an hour. The product precipitated is filtered, washed with 5% aqueous sodium hydroxide, then with several portions of water until neutrality, finally with acetonitrile.

Thus, 12.65 g (93.5%) of the title compound are obtained. M.p.: (after recrystallization from a mixture of 19 volumes of ethanol and 1 volume of water): 179–180° C.

EXAMPLE 26

2-(5-Amino-3-methylthio-1H-1,2,4-triazol-1-yl)-5-/3-(3-dimethylaminopropoxy)phenyl/-1,3,4-thiadiazole hydrochloride To a suspension of 13.0 g (0.033 moles) of 1-(5-amino-3-methylthio-1H-1,2,4-triazol-1-yl)-N'-/3-(3-dimethylaminopropoxy)benzylidene/carbothiohydrazide in 60 ml of acetic acid, a solution of 24.3 g (0.09 moles) of iron(III) chloride hexahydrate in 45 ml of water is added at 25° C. under stirring, then the reaction mixture is boiled for half an hour. On the other day, the reaction mixture is evaporated to dryness under reduced pressure. To the residue, 200 ml of ethanol are added, the product separated is filtered, and washed thoroughly.

Thus, 10.8 g (74.5%) of the title product are obtained. M.p.: (after recrystallization from water): 242–244° C.

EXAMPLE 27

2-(5-Amino-3-methylthio-1H-1,2,4-triazol-1-yl)-5-/4-(3-dimethylamino-2-methylpropoxy)phenyl/-1,3,4-thiadiazole hydrochloride To a suspension of 20.37 g (0.05 moles) of 1-(5-amino-3-methylthio-1H-1,2,4-triazol-1-yl)-N'-/4-(3- dimethylamino-2-methylpropoxy)benzylidene/carbothiohydrazide in 100 ml of acetic acid, a solution of 54 g (0.09 of iron(III) chloride hexahydrate in 300 ml of water is added at 25° C. under stirring, then the reaction mixture is stirred at room temperature for 4 hours. On the other day, the product precipitated is filtered, and washed with methanol.

Thus, 16.9 g (76.5%) of the title product are obtained. M.p.: (after recrystallization from water): 240–242° C.

EXAMPLE 28

2-(5-Amino-3-methylthio-1H-1,2,4-triazole-1-yl)-5-/4-(3-dimethylaminopropoxy)phenyl/-1,3,4-thiadiazole hydrochloride To a suspension of 15.72 g (0.04 moles) of 1-(5-amino-3-methylthio-1H-1,2,4-triazole-1-yl)-N'-/4-(3-dimethylaminopropoxy)benzylidene/carbothiohydrazide in 45 ml of acetic acid, a solution of 26 g (0.09 of iron(III) chloride in 30 ml of water is added at 25° C. under stirring, then the reaction mixture is boiled for half an hour. On the other day, the product precipitated is filtered, and washed with methanol.

Thus, 11.5 g (67.2%) of the title product are obtained. M.p.: (after recrystallization from water): 267–270° C.).

EXAMPLE 29

2-(5-Amino-3-dimethylamino-1H-1,2,4-triazole-1-yl)-5-/2-(3-dimethylaminopropoxy)phenyl/-1,3,4-thiadiazole To a suspension of 5.86 g (0.015 moles) of 1-(5-amino-3-dimethylamino-1H-1,2,4-triazole-1-yl)-N'-/2-(3-dimethylaminopropoxy)benzylidene/carbothiohydrazide in 50 ml of tetrahydrofuran, 4.09 g (0.018 moles) of DDQ are added at 25° C. under stirring and cooling, and the suspension is stirred at room temperature for further 3 hours. To the reaction mixture, 150 ml of 5% aqueous sodium hydroxide solution are added, and the mixture is stirred for further half an hour. The product precipitated is filtered, washed with 5% aqueous sodium hydroxide solution, then with several portions of water until neutrality, finally with acetonitrile.

Thus, 3.55 g (60.9%) of the title compound are obtained. M.p.: (after recrystallization from acetonitrile): 180–182° C.

EXAMPLE 30

2-/5-Amino-3-(2-methylethylthio)-1H-1,2,4-triazole-1-yl/-5-/2-(3-dimethylaminopropoxy)phenyl/-1,3,4-thiadiazole To a suspension of 2.30 g (0.00545 moles) of 1-/5-amino-3-(2-methylethylthio)-1H- 1,2,4-triazole-1-yl/-N'-/2-(3-dimethylaminopropoxy)benzylidene/carbothiohydrazide in 15 ml of tetrahydrofuran, 1.36 g (0.006 moles) of DDQ are added at 25° C. under stirring and cooling, and the suspension is stirred at room temperature for further 3 hours. The tetrahydrofuran is removed from the reaction mixture under reduced pressure, to the residue 20 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 2.0 g (87.4%) of the title compound are obtained. M.p.: (after recrystallization from acetonitrile): 161–163° C.

EXAMPLE 31

2-/5-Amino-3-(4-methylpiperazine-1-yl)-1H-1,2,4-triazole-1-yl/-5-/2-(3-dimethylaminopropoxy)phenyl/-1,3,4-thiadiazole To a suspension of 5.79 g (0.013 moles) of 1-/5-amino-3-(4-methylpiperazine-1-yl)-1H-1,2,4-triazole-1-yl/-N'-/2-(3-dimethylaminopropoxy)benzylidene/carbothiohydrazide in 40 ml of tetrahydrofuran, 3.41 g (0.015 moles) of DDQ are added at 25° C. under stirring and cooling, and the suspension is stirred at room temperature for further 5 hours. The tetrahydrofuran is removed from the reaction mixture under reduced pressure, to the residue 100 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 4.1 g (71.1%) of the title compound are obtained. M.p.: (after recrystallization from a mixture of 1 volume of acetonitrile and 1 volume of 2-propanol): 169–171° C.

EXAMPLE 32

2-(5-Amino-3-piperidino-1H-1,2,4-triazole-1-yl)-5-/2-(3-dimethylaminopropoxy)phenyl/-1,3,4-thiadiazole To a suspension of 5.60 g (0.013 moles) of 1-(5-amino-3-piperidino-1H-1,2,4-triazole-1-yl)-N'-/2-(3-dimethylaminopropoxy)benzylidene/carbothiohydrazide in 50 ml of tetrahydrofuran, 3.41 g (0.015 moles) of DDQ are added at 25° C. under stirring and cooling, and the suspension is stirred at room temperature for further 5 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 5.1 g (91.7%) of the title compounds are obtained. M.p.: (after recrystallization from methanol): 179–181° C.

EXAMPLE 33

2-(5-Amino-3-morpholino-1H-1,2,4-triazole-1-yl)-5-/2-(3-dimethylaminopropoxy)phenyl/-1,3,4-thiadiazole To a suspension of 5.19 g (0.012 moles) of 1-(5-amino-3-morpholino-1H-1,2,4-triazole-1-yl)-N'-/2-(3-dimethylaminopropoxy)benzylidene/carbothiohydrazide in 40 ml of tetrahydrofuran, 3.18 g (0.014 moles) of DDQ are added at 25° C. under stirring and cooling, and the suspension is stirred at room temperature for further 5 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality.

Thus, 4.3 g (83.3%) of the title compound are obtained. M.p.: (after recrystallization from methanol): 180–182° C.

EXAMPLE 34

2-[5-Amino-3-/4-(3-chlorophenyl)piperazine-1-yl/-1H-1,2,4-triazole-1-yl]-5-/2-(3-dimethylaminopropoxy)phenyl/-1,3,4-thiadiazole To a suspension of 6.78 g (0.0125 moles) of 1-[5-amino-3-/4-(chlorophenyl)piperazine-1-yl/-1H-1,2,4-triazole-1- yl]-N'-/2-(3-dimethylaminopropoxy)benzylidene/ carbothiohydrazide in 60 ml of tetrahydrofuran, 3.13 g (0.0138 moles) of DDQ are added at 25° C. under stirring and cooling, and the suspension is stirred at room temperature for further 14 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of viater until neutrality.

Thus, 5.8 g (85.9%) of the title compound are obtained. M.p.: (after recrystallization from a mixture of 1 volume of acetonitrile and 1 volume of tetrahydrofuran): 205–209° C. (under decomposition).

EXAMPLE 35

2-(5-Amino-3-methylthio-1H-1,2,4-triazole-1-yl)-5-/ 3-(2-dimethylaminoethoxy)phenyl/-1,3,4-thiadiazole To a suspension of 5.90 g (0.015 moles) of 1-(5-amino-3-methylthio-1H-1,2,4-triazole-1-yl)-N'-/3-(2-dimethylaminoethoxy)benzylidene/carbothiohydrazide in 50 ml of tetrahydrofuran, 3.75 g (0.0165 moles) of DDQ are added at 25° C. under stirring and cooling, and the suspension is stirred at room temperature for further 8 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality.

Thus, 4.3 g (76.0%) of the title compound are obtained. M.p.: (after recrystallization from acetonitrile): 162–163° C.

EXAMPLE 36

2-(5-Amino-3-methylthio-1H-1,2,4-triazole-1-yl)-5-/ 4-(2-diethylaminoethoxy)phenyl/-1,3,4-thiadiazole To a suspension of 10.54 g (0.025 moles) of 1-(5-amino-3-methylthio-1H- 1,2,4-triazole-1-yl)-N'-/4-(2-diethylaminoethoxy)benzylidene/carbothiohydrazide in 100 ml of tetrahydrofuran, 6.81 g (0.03 moles) of DDQ are added at 25° C. under stirring and cooling, and the suspension is stirred at room temperature for further 8 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality.

Thus, 8.05 g (79.5%) of the title compound are obtained. M.p.: (after recrystallization from a mixture of 1 volume of acetonitrile and 1 volume of 2-propanol): 163–164° C.

EXAMPLE 37

2-(5-Amino-3-methylthio-1H-1,2,4-triazole-1-yl)-5-/ 4-(2-dimethylaminoethoxy)phenyl/-1,3,4-thiadiazole To a suspension of 9.11 g (0.024 moles) of 1-(5-amino-3-methylthio-1H-1,2,4-triazole-1-yl)-N'-/4-(2-dimethylaminoethoxy)benzylidene/carbothiohydrazide in 100 ml of tetrahydrofuran, 6.02 g (0.0265 moles) of DDQ are added at 25° C. under stirring and cooling, and the suspension is stirred at room temperature for further 4 hours. The tetrahydrofuran is removed from the reaction mixture under reduced pressure, to the residue 75 ml of 5% aqueous sodium hydroxide solution are added, and the mixture is stirred for an hour. The product precipitated is filtered, washed with 5% aqueous sodium hydroxide solution, then with several portions of water until neutrality.

Thus, 6.0 g (66.3%) of the title compound are obtained. M.p.: (after recrystallization from a mixture of 1 volume of water and 1 volume of 2-propanol): 183.5184° C.

EXAMPLE 38

2-(5-Amino-3-methylthio-1H-1,2,4-triazole-1-yl)-5- [2-/3-(4-(methylpiperazine-1-yl)-pronoxy/phenyl]-1, 3,4-thiadiazole To a suspension of 4.93 g (0.011 moles) of 1-(5-amino-3-methylthio-1H-1,2,4-triazole-1-yl)-N'-[2-/3-(4-methylpiperazine-1-yl)propoxy)benzylidene] carbothiohydrazide in 30 ml of tetrahydrofuran, 2.95 g (0.013 moles) of DDQ are added at 25° C. under stirring and cooling, and the suspension is stirred at room temperature for further 6 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 3.98 g (81.1%) of the title compound are obtained. M.p.: (after recrystallization from ethanol): 177–178° C.

EXAMPLE 39

2-(5-Amino-3-methylthio-1H-1,2,4-triazole-1-yl)-5-/ 2-(3-piperidinopropoxy)phenyl/-1,3,4-thiadiazole To a suspension of 6.59 g (0.0152 moles) of 1-(5-amino-3-methylthio-1H-1,2,4-triazole-1-yl)-N'-/2-(3-piperidinopropoxy)benzylidene/carbothiohydrazide in 50 ml of tetrahydrofuran, 4.09 g (0.018 moles) of DDQ are added at 25° C. under stirring and cooling, and the suspension is stirred at room temperature for further 5 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 6.04 g (93.3%) of the title compound are obtained. M.p.: (after recrystallization from a mixture of 1 volume of ethanol and 1 volume of acetonitrile): 185–186° C.

EXAMPLE 40

2-(5-Amino-3-methylthio-1H-1,2,4-triazole-1-yl)-5-/ 2-(2-dimethylaminoethoxy)phenyl/-1,3,4-thiadiazole To a suspension of 8.01 g (0.021 moles) of 1-(5-amino-3-methylthio-1H-1,2,4-triazole-1-yl)-N'-/2-(2-dimethylaminoethoxy)benzylidene/carbothiohydrazide in 40 ml of tetrahydrofuran, 5.45 g (0.024 moles) of DDQ are added at 25° C. under stirring and cooling, and the suspension is stirred at room temperature for further 5 hours. The tetrahydrofuran is removed from the reaction mixture under reduced pressure, to the residue 80 ml of 5% aqueous sodium hydroxide solution are added, and the mixture is stirred for an hour. The product precipitated is filtered, Crashed with 5% aqueous sodium hydroxide solution, then with several portions of water until neutrality, finally with acetonitrile.

Thus, 7.24 g (91.3%) of the title compound are obtained. M.p.: (after recrystallization from acetonitrile): 193–195° C.

EXAMPLE 41

2-(5-Amino-3-methylthio-1H-1,2,4-triazole-1-yl)-5-/2-(3-morpholinopropoxy)phenyl/-1,3,4-thiadiazole To a suspension of 6.53 g (0.015 moles) of 1-(5-amino-3-methylthio-1H-1,2,4-triazole-1-yl)-N'-/2-(3-morpholinopropoxy)benzylidene/carbothiohydrazide in 50 ml of tetrahydrofuran, 4.09 g (0.018 moles) of DDQ are added at 25° C. under stirring and cooling, and the suspension is stirred at room temperature for further 13 hours. The tetrahydrofuran is removed from the reaction mixture under reduced pressure, to the residue 80 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 5.68 g (87.4%) of the title compound are obtained. M.p.: (after recrystallization from acetonitrile): 205–206° C.

EXAMPLE 42

2-/5-Amino-3-(4-chlorobenzylthio)-1H-1,2,4-triazole-1-yl/-5-/2-(3-dimethylaminopropoxy)phenyl/-1,3,4-thiadiazole To a suspension of 4.53 g (0.009 moles) of 1-/5-amino-3-(4-chlorobenzylthio)-1H-1,2,4-triazole-1-yl/-N'-/2-(3-dimethylaminopropoxy)benzylidene/carbothiohydrazide in 25 ml of tetrahydrofuran, 2.45 g (0.0108 moles) of DDQ are added at 25° C. under stirring and cooling, and the suspension is stirred at room temperature for further 13 hours. The tetrahydrofuran is removed from the reaction mixture under reduced pressure, to the residue 20 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 4.19 g (92.9%) of the title compound are obtained. M.p. (after recrystallization from a mixture of 1 volume of n-butanol and 1 volume of acetonitrile): 183–184° C.

EXAMPLE 43

2-(5-Amino-3-methylthio-1H-1,2,4-triazole-1-yl)-5-/2-(3-pyrrolidinopropoxy)phenyl/-1,3,4-thiadiazole To a suspension of 9.02 g (0.0215 )moles) of 1-(5-amino-3-methylthio-1H-1,2,4-triazole-1-yl)-N'-/2-(3-pyrrolidinopropoxy)benzylidene/carbothiohydrazide in 70 ml of tetrahydrofuran, 5.61 g (0.025 moles) of DDQ are added at 25° C. under stirring and cooling, and the suspension is stirred at room temperature for further 21 hours. The tetrahydrofuran is removed from the reaction mixture under reduced pressure, to the residue 20 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 8.34 g (93%) of the title compound are obtained. M.p.: (after recrystallization from a mixture of 1 volume of ethanol and 1 volume of acetonitrile): 169.5–171° C.

EXAMPLE 44

2-(5-Amino-3-pyrrolidino-1H-1,2,4-triazole-1-yl)-5-/2-(3-dimethylaminopropoxy)phenyl/-1,3,4-thiadiazole To a suspension of 10.0 g (0.024 moles) of 1-(5-amino-3-pyrrolidino-1H-1,2,4-triazole-1-yl)-N'-/2-(3-dimethylaminopropoxy)benzylidene/carbothiohydrazide in 80 ml of tetrahydrofuran, 6.13 g (0.027 moles) of DDQ are added at 25° C. under stirring and cooling, and the suspension is stirred at room temperature for further 21 hours. The tetrahydrofuran is removed from the reaction mixture under reduced pressure, to the residue 80 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 8.92 g (89.7%) of the title compound are obtained. M.p. (after recrystallization from a mixture of 1 volume of n-butanol and 1 volume of acetonitrile): 209–211° C.

EXAMPLE 45

2-(5-Amino-3-methylthio-1H-1,2,4-triazole-1-yl)-5-[2-/3-di(2-methylethyl)aminopropoxy/phenyl]-1,3,4-thiadiazole To a suspension of 7.19 g (0.016 moles) of 1-(5-amino-3-methylthio-1H-1,2,4-triazole-1-yl)-N'-[2-/3-di(2-methylethyl)aminopropoxy)benzylidene]carbothiohydrazide in 40 ml of tetrahydrofuran, 4.09 g (0.018 moles) of DDQ are added at 25° C. under stirring and cooling, and the suspension is stirred at room temperature for further 6 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 5.60 g (78.2%) of the title compound are obtained. M.p. (after recrystallization from a mixture of 1 volume of ethanol and 1 volume of acetonitrile): 177–178° C.

EXAMPLE 46

2-(5-Amino-3-methylthio-1H-1,2,4-triazole-1-yl)-5-/2-(3-diethylaminopropoxy)phenyl/-1,3,4-thiadiazole To a suspension of 7.59 g (0.018 moles) of 1-(5-amino-3-methylthio-1H-1,2,4-triazole-1-yl)-N'-/2-(3-diethylaminopropoxy)benzylidene/carbothiohydrazide in 70 ml of tetrahydrofuran, 4.54 g (0.020 moles) of DDQ are added at 25° C. under stirring and cooling, and the suspension is stirred at room temperature for further 22 hours. The tetrahydrofuran is removed from the reaction mixture under reduced pressure, to the residue 60 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 5.83 g (77.2%) of the title compound are obtained. M.p. (after recrystallization from 2-propanol): 142–144° C.

EXAMPLE 47

2-/5-Amino-3-(4-methylpiperazine-1-yl)-1H-1,2,4-triazole-1-yl/-5-/4-(3-dimethylaminopropoxy)phenyl/-1,3,4-thiadiazole To a suspension of 8.51 g (0.0185 moles) of 1-/5-amino-3-(4-methylpiperazine-1-yl)-1H-1,2,4-triazole-1-yl/-N'-/4-(3-dimethylaminopropoxy)benzylidene/carbothiohydrazide in 50 ml of tetrahydrofuran, 4.65 g (0.0205 moles) of DDQ are added at 25° C. under stirring and cooling, and the suspension is stirred at room temperature for further 6 hours. The tetrahydrofuran is removed from the reaction mixture under reduced pressure, to the residue 60 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 6.12 g (72.3%) of the title compound are obtained. M.p. (after recrystallization from a mixture of 1 volume of 2-propanol and 1 volume of acetonitrile): 172–174° C.

EXAMPLE 48

2-(3,5-Diamino-1H-1,2,4-triazole-1-yl)-5-/2-(3-dimethylaminopropoxy)phenyl/-1,3,4-thiadiazole To a suspension of 5.64 g (0.0155 moles) of 1-(3,5-diamino-1-yl)-1H-1,2,4-triazole-1-yl)-N'-/2-(3-dimethylaminopropoxy)benzylidene/carbothiohydrazide in 40 ml of tetrahydrofuran, 3.86 g (0.017 moles) of DDQ are added at 25° C. under stirring and cooling, and the suspension is stirred at room temperature for further 5 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 4.22 g (75.6%) of the title compound are obtained that is suspended in 15 ml of acetonitrile, and stirred for 2 hours intensively. The crystals are filtered, and washed thoroughly with acetonitrile. Thus, 3.57 g of pure product are obtained. M.p.: 217–222° C.

EXAMPLE 49

2-(5-Amino-3-diallylamino-1H-1,2,4-triazole-1-yl)-5-/2-(3-dimethylaminopropoxy)phenyl/-1,3,4-thiadiazole To a suspension of 5.98 g (0.0135 moles) of 1-(5-amino-3-diallylamino-1H-1,2,4-triazole-1-yl)-N'-/2-(3-dimethylaminopropoxy)benzylidene/carbothiohydrazide in 30 ml of tetrahydrofuran, 3.41 g (0.015 moles) of DDQ are added at 25° C. under stirring and cooling, and the suspension is stirred at room temperature for further 4 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 4.24 g (71.3%) of the title compound are obtained. M.p. (after chromatography on a Kieselgel 60 H layer): 136–140° C.

EXAMPLE 50

2-(5-Amino-3-propylthio-1H-1,2,4-triazole-1-yl)-5-/2-(3-dimethylaminopropoxy)phenyl/-1,3,4-thiadiazole To a suspension of 2.95 g (0.007 moles) of 1-(5-amino-3-propylthio-1H-1,2,4-triazole-1-yl))-N'-/2-(3-dimethylaminopropoxy)benzylidene/carbothiohydrazide in 20 ml of tetrahydrofuran, 1.75 g (0.0077 moles) of DDQ are added at 25° C. under stirring and cooling, and the suspension is stirred at room temperature for a further hour. The product precipitated is filtered, added to 30 ml of 5% aqueous sodium hydroxide solution, and stirred at room temperature for 2 hours. The insoluble part is filtered, washed with water, then with tetrahydrofuran.

Thus, 2.32 g (79.2%) of the title compound are obtained. M.p.: 147–150° C.

EXAMPLE 51

2-(5-Amino-3-diallylamino-1H-1,2,4-triazole-1-yl)-5-/3-(3-dimethylamino-2-methylpropoxy)phenyl/-1,3,4-thiadiazole To a suspension of 4.57 g (0.01 moles) of 1-(5-amino-3-diallylamino-1H-1,2,4-triazole-1-yl)-N'-/3-(3-dimethylamino-2-methylpropoxy)benzylidene/carbothiohydrazide in 25 ml of tetrahydrofuran, 2.50 g (0.011 moles) of DDQ are added at 25° C. under stirring and cooling, and the suspension is stirred at room temperature for further 3 hours. The tetrahydrofuran is removed from the reaction mixture under reduced pressure, to the residue 40 ml of 5% aqueous sodium hydroxide solution are added, and the mixture is stirred for an hour. The product precipitated is filtered, washed with 5% aqueous sodium hydroxide solution, then with several portions of water until neutrality.

Thus, 3.92 g (86.3%) of the title compound are obtained. M.p. (after chromatography on a Kieselgel 60 H layer): 135–137° C.

EXAMPLE 52

2-(5-Amino-3-diallylamino-1H-1,2,4-triazole-1-yl)-5-/4-(3-dimethylamino-2-methylpropoxy)phenyl/-1,3,4-thiadiazole To a suspension of 4.57 g (0.01 moles) of 1-(5-amino-3-diallylamino-1H-1,2,4-triazole-1-yl)-N'-/4-(3-dimethylamino-2-methylpropoxy)benzylidene/carbothiohydrazide in 25 ml of tetrahydrofuran, 2.50 g (0.011 moles) of DDQ are added at 25° C. under stirring and cooling, and the suspension is stirred at room temperature for further 3 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality. The product is dissolved in chloroform, the solution obtained is washed with a saturated aqueous sodium chloride solution, dried, and evaporated to dryness.

Thus, 3.63 g (79.8%) of the title compound are obtained. M.p. (after chromatography on a Kieselgel 60 H layer, then recrystallization from acetonitrile): 105–107° C.

EXAMPLE 53

2-(5-Amino-3-diallylamino-1H-1,2,4-triazole-1-yl)-5-/3-(3-dimethylamino-2-methylpropoxy)phenyl/-1,3,4-thiadiazole To a suspension of 4.57 g (0.01 moles) of 1-(5-amino-3-diallylamino-1H-1,2,4-triazole-1-yl)-N'-/3-(3-dimethylamino- 2-methylpropoxy)benzylidene/carbothiohydrazide in 25 ml of tetrahydrofuran, 2.50 g (0.011 moles) of DDQ are added at 25° C. under stirring and cooling, and the suspension is stirred at room temperature for further 3 hours. The tetrahydrofuran is removed from the reaction mixture under reduced pressure, to the residue 40 ml of 5% aqueous sodium hydroxide solution are added, and the mixture is stirred for an hour. The product precipitated is filtered, washed with 5% aqueous sodium hydroxide solution, then with several portions of water until neutrality.

Thus, 4.0 g (79.8%) of the title compound are obtained. M.p. (after chromatography on a Kieselgel 60 H layer, then recrystallization from acetonitrile): 130–132° C.

EXAMPLE 54

2-(5-Amino-3-diallylamino-1H-1,2,4-triazole-1-yl)-5-/2-(2-diethylaminoethoxy)phenyl/-1,3,4-thiadiazole To a suspension of 4.57 g (0.01 moles) of 1-(5-amino-3-diallylamino-1H-1,2,4-triazole-1-yl)-N'-/2-(2-diethylaminoethoxy)benzylidene/carbothiohydrazide in 25 ml of tetrahydrofuran, 2.50 g (0.011 moles) of DDQ are added at 25° C. under stirring and cooling, and the suspension is stirred at room temperature for further 2 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality.

Thus, 3.84 g (84.4%) of the title compound are obtained. M.p. (after chromatography on a Kieselgel 60 H layer): 124–126° C.

EXAMPLE 55

2-(5-Amino-3-piperidino-1H-1,2,4-triazole-1-yl)-5-/2-(2-dimethylaminoethoxy)phenyl/-1,3,4-thiadiazole To a suspension of 7.50 g (0.018 moles) of 1-(5-amino-3-piperidino-1H-1,2,4-triazole-1-yl)-N'-/2-(2-dimethylaminoethoxy)benzylidene/carbothiohydrazide in 50 ml of tetrahydrofuran, 4.54 g (0.02 moles) of DDQ are added at 25° C. under stirring and cooling, and the suspension is stirred at room temperature for further 5 hours. The tetrahydrofuran is removed from the reaction mixture under reduced pressure, to the residue 100 ml of 5% aqueous sodium hydroxide solution are added, and the mixture is stirred for an hour. The product precipitated is filtered, washed with 5% aqueous sodium hydroxide solution, then with several portions of water until neutrality.

Thus, 6.75 g (81.4%) of the title compound are obtained. M.p. (after chromatography on a Kieselgel 60 H layer and recrystallization from acetonitrile: 189–191° C.

EXAMPLE 56

2-(5-Amino-3-diallylamino-1H-1,2,4-triazole-1-yl)-5-/2-(2-dimethylaminoethoxy)phenyl/-1,3,4-thiadiazole To a suspension of 4.28 g (0.01 moles) of 1-(5-amino-3-diallylamino-1H-1,2,4-triazole-1-yl)-N'-/2-(2-dimethylaminoethoxy)benzylidene/carbothiohydrazide in 45 ml of tetrahydrofuran, 2.50 g (0.011 moles) of DDQ are added at 25° C. under stirring and cooling, and the suspension is stirred at room temperature for further 3 hours. The tetrahydrofuran is removed from the reaction mixture under reduced pressure, to the residue 50 ml of 5% aqueous sodium hydroxide solution are added, and the mixture is stirred for an hour. The product precipitated is filtered, washed with 5% aqueous sodium hydroxide solution, then with several portions of water until neutrality.

Thus, 3.8 g (89.0%) of the title compound are obtained. M.p. (after chromatography on a Kieselgel 60 H layer): 138–140° C.

EXAMPLE 57

2-(5-Amino-3-allylthio-1H-1,2,4-triazole-1-yl)-5-/2-(3-dimethylaminopropoxy)phenyl/-1,3,4-thiadiazole To a suspension of 3.78 g (0.009 moles) of 1-(5-amino-3-allylthio-1H-1,2,4-triazole-1-yl)-N'-/2-(3-dimethylaminopropoxy)benzylidene/carbothiohydrazide in 20 ml of tetrahydrofuran, 2.27 g (0.01 moles) of DDQ are added at 25° C. under stirring and cooling, and the suspension is stirred at room temperature for a further hour. The product precipitated is filtered and added to 30 ml of 5% aqueous sodium hydroxide solution, and the mixture is stirred at room temperature for 2 hours. The insoluble part is filtered, washed With water, then with tetrahydrofuran.

Thus, 2.98 g (79.5%) of the title compound are obtained. M.p.: 169–172° C.

EXAMPLE 58

2-(5-Amino-3-benzylthio-1H-1,2,4-triazole-1-yl)-5-/2-(3-dimethylaminopropoxy)phenyl/-1,3,4-thiadiazole To a suspension of 3.76 g (0.008 moles) of 1-(5-amino-3-benzylthio-1H-1,2,4-triazole-1-yl)-N'-/2-(3-dimethylaminopropoxy)benzylidene/carbothiohydrazide in 20 ml of tetrahydrofuran, 2.04 g (0.009 moles) of DDQ are added at 25° C. under stirring and cooling, and the suspension is stirred at room temperature for a further hour. The product precipitated is filtered and added to 30 ml of 5% aqueous sodium hydroxide solution, and the mixture is stirred at room temperature for 2 hours. The insoluble part is filtered, washed with water, then with tetrahydrofuran.

Thus, 2.76 g (73.8%) of the title compound are obtained. M.p.: 189–191° C.

EXAMPLE 59

2-(5-Amino-3-piperidino-1H-1,2,4-triazole-1-yl)-5-/2-(2-diallylaminoethoxy)phenyl/-1,3,4-thiadiazole A mixture of 4.50 g (0.01 moles) of 2-(5-amino-3-piperidino-1H-1,2,4-triazole-1-yl)-5-/2-(2-bromoethoxy)phenyl/-1,3,4-thiadiazole and 15 ml of diallylamine is stirred at 120° C. for 3 hours. From the melt obtained the excess of amine is evaporated under reduced pressure, to the residue 70 ml seater are added, and allowed to crystallize. The crystals formed are filtered, washed with water, then with acetonitrile.

Thus, 4.16 g (89.2%) of the title compound are obtained. M.p. (after chromatography on a Kieselgel 60 H layer and recrystallization from acetonitrile): 148–150° C.

EXAMPLE 60

2-(5-Amino-3-n-hexylthio-1H-1,2,4-triazole-1-yl)-5-/2-(3-dimethylaminopropoxy)phenyl/-1,3,4-thiadiazole To a suspension of 0.99 g (0.0036 moles) of 1-(5-amino-3-n-hexylthio-1H-1,2,4-triazole-1-yl)-N'-/2-(3-dimethylaminopropoxy)benzylidene/carbothiohydrazide in 10 ml of tetrahydrofuran, 0.83 g (0.004 moles) of DDQ are added at 25° C. under stirring and cooling, and the suspension is stirred at room temperature for further 2 hours. The reaction mixture is evaporated to dryness under reduced pressure, the residue is suspended in some ethyl acetate, filtered, and washed with ethyl acetate.

Thus, 0.94 g (56.6%) of the title compound are obtained. M.p.: 114–117° C.

EXAMPLE 61

2-(5-Benzylamino-3-methylethylthio-1H-1,2,4-triazole-1-yl)-5-/2-(3-dimethylaminopropoxy)phenyl/-1,3,4-thiadiazole To a suspension of 5.11 g (0.01 moles) of 1-(5-benzyl-amino-3-methylethylthio-1H-1,2,4-triazole-1-yl)-N'-/2-(3-dimethylaminopropoxy)benzylidene/carbothiohydrazide in 50 ml of tetrahydrofuran, 2.73 g (0.012 moles) of DDQ are added at 25° C. under stirring and cooling, and the suspension is stirred at room temperature for a further hour. The tetrahydrofuran is removed from the reaction mixture under reduced pressure, to the residue 30 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 4.88 g (95.8%) of the title compound are obtained. M.p.: 101–102° C.

EXAMPLE 62

2-(5-Benzylamino-3-amino-1H-1,2,4-triazole-1-yl)-5-/2-(3-dimethylaminopropoxy)phenyl/-1,3,4-thiadiazole To a suspension of 1.81 g (0.004 moles) of 1-(5-benzyl-amino-3-amino-1H-1,2,4-triazole-1-yl)-N'-/2-(3-dimethylaminopropoxy)benzylidene/carbothiohydrazide in 15 ml of tetrahydrofuran, 1.02 g (0.0045 moles) of DDQ are added at 25° C. under stirring and cooling, and the suspension is stirred at room temperature for further 4 hours. The tetrahydrofuran is removed from the reaction mixture under reduced pressure, to the residue 30 ml of 5% aqueous sodium hydroxide solution are added, and the mixture is extracted with dichloromethane. The organic solution is extracted with 5% aqueous sodium hydroxide solution, finally washed with several portions of water until neutrality, then the solvent is evaporated.

Thus, 1.10 g (61.0%) of the title compound are obtained. M.p. (after recrystallization from acetonitrile): 180–183° C.

EXAMPLE 63

2-(5-Amino-3-benzylamino-1H-1,2,4-triazole-1-yl)-5-/2-(3-dimethylaminopropoxy)phenyl/-1,3,4-thiadiazole To a suspension of 3.30 g (0.0073 moles) of 1-(5-amino-3-benzyl-amino-3-1H-1,2,4-triazole-1-yl)-N'-/2-(3-dimethylaminopropoxy)benzylidene/carbothiohydrazide in 35 ml of tetrahydrofuran, 1.84 g (0.0081 moles) of DDQ are added at 25° C. under stirring and cooling, and the suspension is stirred at room temperature for further 5 hours. The tetrahydrofuran is removed from the reaction mixture under reduced pressure, to the residue 30 ml of 5% aqueous sodium hydroxide solution are added, the product precipitated is filtered, washed with 5% aqueous sodium hydroxide solution, then with water until.

Thus, 3.12 g (94.8%) of the title compound are obtained. M.p. (after recrystallization from a mixture of 1 volume of acetonitrile and 1 volume of ethanol): 172–173° C.

EXAMPLE 64

2-/5-(4-Chlorobenzylamino)-3-methylthio-1H-1,2,4-triazole-1-yl/-5-/2-(3-dimethylaminopropoxy)phenyl/-1,3,4-thiadiazole To a suspension of 5.18 g (0.01 moles) of 1-/5-(4-chlorobenzylamino)-3-methylthio-1H-1,2,4-triazole-1-yl)-N'-/2-(3-dimethylaminopropoxy)benzylidene/carbothiohydrazide in 50 ml of tetrahydrofuran, 2.73 g (0.012 moles) of DDQ are added at 25° C. under stirring and cooling, and the suspension is stirred at room temperature for a further hour. The tetrahydrofuran is removed from the reaction mixture under reduced pressure, to the residue 30 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 4.65 g (90.1%) of the title compound are obtained. M.p.: 133–134° C.

EXAMPLE 65

2-/5-(4-Chlorobenzylamino)-3-methylethylthio-1H-1,2,4-triazole-1-yl/-5-/2-(3-dimethylaminopropoxy)phenyl/-1,3,4-thiadiazole To a suspension of 2.73 g (0.005 moles) of 1-/5-(4-chlorobenzylamino)-3-methylethylthio-1H-1,2,4-triazole-1-yl)-1-N'-/2-( 3-dimethylaminopropoxy)benzylidene/carbothiohydrazide in 30 ml of tetrahydrofuran, 1.50 g (0.006 moles) of DDQ are added at 25° C. under stirring and cooling, and the suspension is stirred at room temperature for a further hour. The tetrahydrofuran is removed from the reaction mixture under reduced pressure, to the residue 30 ml of 5% aqueous sodium hydroxide solution are added, and the mixture is stirred for an hour. The product precipitated is filtered, washed with 5% aqueous sodium hydroxide solution, then with several portions of water until neutrality, finally with acetonitrile.

Thus, 2.20 g (88.1%) of the title compound are obtained. M.p.: 104–105° C.

EXAMPLE 66

2-(5-Amino-3-piperidino-1H-1,2,4-triazole-1-yl)-5-/4-(2-diallylaminoethoxy)phenyl/-1,3,4-thiadiazole A mixture of 3.60 g (0.008 moles) of 2-(5-Amino-3-piperidino-1H-1,2,4-triazole-1-yl)-5-/4-(2-bromoethoxy)phenyl/-1,3,4-thiadiazole and 7.77 g (9.9 ml, 0.08 moles) of diallylamine is stirred at 120° C. for 3 hours. The solution obtained crystallizes on cooling. 30 ml of ether are added to the reaction mixture that is stirred for 30 minutes. The crystals precipitated are filtered, washed with ether, then with acetonitrile.

Thus, 3.11 g (83.3%) of the title compound are obtained. M.p. (after chromatography on a Kieselgel 60 H layer and recrystallization from acetonitrile): 163–166° C.

EXAMPLE 67

2-(5-Amino-3-piperidino-1H-1,2,4-triazole-1-yl)-5-/2-(4-di-n-butylaminobutoxy)phenyl/-1,3,4-thiadiazole A mixture of 0.465 g (0.001 moles) of 2-(5-Amino-3-piperidino-1H-1,2,4-triazole-1-yl)-5-/2-(4-bromobutoxy)

phenyl/-1,3,4-thiadiazole and 1.29 g (0.01 moles) of di-n-butylamine is stirred at 120° C. for 2 hours. 5 ml of water are added to the reaction mixture that is stirred for 30 minutes. The crystals precipitated are filtered, washed with ether, water, then with acetonitrile.

Thus, 0.40 g of the title compound are obtained that is subjected to chromatography on a Kieselgel 60 H layer, then recrystallized from acetonitrile. Yield: 0.33 g (64.3%). M.p.: 148–150° C.

EXAMPLE 68

2-(5-Amino-3-propargylthio-1H-1,2,4-triazole-1-yl)-5-/2-(3-dimethylaminopropoxy)phenyl/-1,3,4-thiadiazole To a suspension of 3.34 g (0.008 moles) of 1-(5-amino-3-propargylthio-1H-1,2,4-triazole-1-yl)-N'-/2-(3-dimethylaminopropoxy)benzylidene/carbothiohydrazide in 20 ml of tetrahydrofuran, 2.0 g (0.088 moles) of DDQ are added at 25° C. under stirring and cooling, and the suspension is stirred at room temperature for a further hour. The product precipitated is filtered and added to 30 ml of 5% (g/ml) aqueous sodium hydroxide solution, and the mixture is stirred at room temperature for 2 hours. The insoluble part is filtered, washed with 5% aqueous sodium hydroxide solution, water and tetrahydrofuran.

Thus, 1.86 g (56.0%) of the title compound are obtained. M.p. (after chromatography on a Kieselgel 60 H layer, then recrystallization from acetonitrile): 181–183° C.

EXAMPLE 69

2-/5-Amino-3-(2-methylethylthio)-1H-1,2,4-triazole-1-yl/-5-[3-/3-(4-phenylpiperazine-1-yl)propoxy/phenyl]-1,3,4-thiadiazole A mixture of 4.35 g (0.01 moles) of 2-/5-amino-3-(2-methylethylthio)-1H-1,2,4-triazole-1-yl/-5-/3-(3-bromopropoxy)/phenyl-1,3,4-thiadiazole and 4.98 g (0.03 moles) of 4-phenylpiperazine is stirred at 150° C. for 0.5 hours. After cooling, 40 ml of water are added, drop by drop, to the reaction mixture, and the crystals precipitated are filtered.

Thus, 3.35 g (74.0%) of the title compound are obtained. M.p. (after chromatography on a Kieselegel 60 H layer, then recrystallization from acetonitrile): 141–143° C.

EXAMPLE 70

2-/5-Amino-3-(2-methylthio)-1H-1,2,4-triazole-1-yl/-5-{2-[3-/4-(2-methoxyphenyl)piperazine-1-yl/propoxy]phenyl}-1,3,4-thiadiazole A mixture of 4.07 g (0.01 moles) of 2-/5-amino-3-(2-methylthio)-1H-1,2,4-triazole-1-yl/-5-/2-(3-bromopropoxy)/phenyl-1,3,4-thiadiazole and 5.88 g (0.03 moles) of 4-(2-methoxyphenyl)piperazine is stirred at 180° C. for 0.5 hours. After cooling, 40 ml of water are added, drop by drop, to the reaction mixture, and the crystals precipitated are filtered.

Thus, 3.80 g (79.0%) of the title compound are obtained. M.p. (after chromatography on a Kieselgel 60 H layer, then recrystallization from acetonitrile): 159–161° C.

EXAMPLE 71

2-/5-Amino-3-(2-methylethylthio)-1H-1,2,4-triazole-1-yl/-5-[2-/3-(4-phenylpiperazine-1-yl)propoxy/phenyl]-1,3,4-thiadiazole A mixture of 4.35 g (0.01 moles) of 2-/5-amino-3-(2-methylethylthio)-1H-1,2,4-triazole-1-yl/-5-/2-(3-bromopropoxy)/phenyl-1,3,4-thiadiazole and 4.98 g (0.03 moles) of 4-phenylpiperazine is stirred at 160° C. for 0.5 hours. After cooling, 40 ml of water are added, drop by drop, to the reaction mixture, and the crystals precipitated are filtered.

Thus, 3.55 g (74.0%) of the title compound are obtained. M.p. (after chromatography on a Kieselgel 60 H layer, then recrystallization from acetonitrile): 212–214° C.

EXAMPLE 72

2-/5-Amino-3-(2-methylethylthio)-1H-1,2,4-triazole-1-yl/-5-{2-[3-/4-(2-methoxyphenyl)piperazine-1-yl/propoxy]phenyl}-1,3,4-thiadiazole A mixture of 4.35 g (0.01 moles) of 2-/5-amino-3-(2-methylethylthio)-1H-1,2,4-triazole-1-yl/-5-/2-(3-bromopropoxy)/phenyl-1,3,4-thiadiazole and 5.88 g (0.03 moles) of 4-(2-methoxyphenyl)piperazine is stirred at 160° C. for 0.5 hours. After cooling, 40 ml of water are added, drop by drop, to the reaction mixture, and the crystals pprecipitated are filtered.

Thus, 4.28 g (84.0%) of the title compound are obtained. M.p. (after chromatography on a Kieselgel 60 H layer, then recrystallization from acetonitrile), 159–160° C.

EXAMPLE 73

2-(5-Amino-3-piperidino-1H-1,2,4-triazole-1-yl)-5-/3-methoxy-2-(3-morpholinopropoxy)phenyl/-1,3,4-thiadiazole A mixture of 3.96 g (0.008 moles) of 2-(5-amino-3-piperidino-1H-1,2,4-triazole-1-yl)-5-/3-methoxy-2-(3-bromopropoxy)/phenyl-1,3,4-thiadiazole and 15 g (0.172 moles) of morpholine is stirred at 140° C. for 10 hours. After cooling, the excess of morpholine is distilled off under reduced pressure, to the residue 40 ml of water are added, drop by drop, and the crystals precipitated are filtered.

Thus, 3.4 g (85%) of the title compound are obtained. M.p. (after chromatography on a Kieselgel 60 H layer, then recrystallization from acetonitrile): 160–163° C.

EXAMPLE 74

2-(5-Benzylamino-3-piperidino-1H-1,2,4-triazole-1-yl)-5-/2-(3-dimethylamnino)propoxyphenyl/-1,3,4-thiadiazole To a suspension of 5.20 g (0.010 moles) of 2-(5-benzylamino-3-piperidino-1H-1,2,4-triazole-1-yl)-N'-/2-(3-dimethylaminopropoxy)benzylidene/carbothiohydrazide in 40 ml of tetrahydrofuran, 2.5 g (0.011 moles) of DDQ are added at 25° C. under stirring and cooling, and the suspension is stirred at room temperature for further 4 hours. From the reaction mixture, the tetrahydrofuran is removed by evaporation under reduced pressure, the residue is purified by chromatography over a column filled with Kieselgel H.

Thus, 4.09 g (78.5%) of the title compound are obtained. M.p. (after recrystallization from acetonitrile): 100–101° C.

EXAMPLE 75

2-(5-Amino-3-piperidino-1H-1,2,4-triazole-1-yl)-5-/3-2-(3-diallylaminoethoxy)phenyl/-1,3,4-thiadiazole A mixture of 4.50 g (0.01 moles) of 2-(5-amino-3-piperidino-1H-1,2,4-triazole-1-yl)-5-/3-(2-bromoethoxy)phenyl/-1,3,4-thiadiazole and 9.72 g (0.1 moles) of diallylamine is stirred at 120° C. for 1.5 hours. On cooling, the solution obtained crystallizes. 30 ml of ether are added to the reaction mixture that is stirred for 30 minutes. The crystals precipitated are filtered, washed with ether, then with acetonitrile.

Thus, 3.65 g (78.3%) of the title compound are obtained. M.p. (after chromatography on a Kieselgel 60 H layer, then recrystallization from acetonitrile): 128–131° C.

EXAMPLE 76

2-(5-Amino-3-diethylamino-1H-1,2,4-triazole-1-yl)-5-/2-(3-dimethylamino)propoxyphenyl/-1,3,4-thiadiazole To a suspension of 3.36 g (0.08 moles) of 2-(5-amino-3-diethylamino-1H-1,2,4-triazole-1-yl)-N'-/2-(3-dimethylaminopropoxy)benzylidene/carbothiohydrazide in 25 ml of tetrahydrofuran, 2.0 g (0.0088 moles) of DDQ are added at 25° C. under stirring and cooling, and the suspension is stirred at room temperature for further 3 hours. 40 ml of 5% aqueous sodium hydroxide solution are added to the reaction mixture that is stirred for further half an hour. The product precipitated is filtered, washed with 5% aqueous sodium hydroxide solution, then with several portions of water until neutrality, finally with acetonitrile.

Thus, 2.8 g (84.1%) of the title compound are obtained. M.p. (after recrystallization from acetonitrile): 159–160° C.

EXAMPLE 77

2-(5-Amino-3-heptamemethyleneimino-1H-1,2,4-triazole-1-yl)-5-/2-(3-dimethylamino)propoxyphenyl/-1,3,4-thiadiazole To a suspension of 6.19 g (0.0135 moles) of 2-(5-amino-3-heptamethyleneimino-1H-1,2,4-triazole-1-yl)-N'-/2-(3-dimethylaminopropoxy)benzylidene/carbothiohydrazide in 30 ml of tetrahydrofuran, 3.41 g (0.015 moles) of DDQ are added at 25° C. under stirring and cooling, and the suspension is stirred at room temperature for further 5 hours. From the reaction mixture, the tetrahydrofuran is removed by evaporation under reduced pressure, to the residue 50 ml of 5% aqueous sodium hydroxide solution are added, and the mixture is stirred for a further hour. The product precipitated is filtered, washed with 5% aqueous sodium hydroxide solution, then with several portions of water until neutrality, finally with acetonitrile.

Thus, 5.05 g (81.9%) of the title compound are obtained. M.p. (after recrystallization from methanol): 164–167° C.

EXAMPLE 78

2-/5-Amino-3-(4-methylpiperazine-1-yl)-1H-1,2,4-triazole-1-yl/-5-/2-(3-dimethylamino)-2-methylpropoxyphenyl/-1,3,4-thiadiazole To a solution of 15.72 g (0.0339 moles) of 2-/5-amino-3-(4-methylpiperazine-1-yl)-1H-1,2,4-triazole-1-yl/-N'-/2-(3-dimethylamino-2-methylpropoxy)benzylidene/carbothiohydrazide in 100 ml of acetic acid, a solution of 26 g of iron(III) chloride in 30 ml of water are added at 25° C. under cooling, and the reaction mixture is stirred at room temperature for 3 hours. 100 ml of isopropanol are added to the reaction mixture, the product precipitated is filtered and washed with isopropanol thoroughly.

Thus, 21.1 g of the hydrochloride of the title product are obtained, to which 200 ml of chloroform and 30 ml of triethylamine are added, the solution is extracted twice using 100 ml of water each time, dried over anhydrous sodium sulfate, and the solvent is distilled off. aThus, 8.5 g (49.9%) of the title compound are obtained. M.p. (after recrystallization from acetonitrile): 170–172° C.

EXAMPLE 79

2-(5-Amino-3-diallylamino-1H-1,2,4-triazole-1-yl)-5-/4-(3-dimethylamino)propoxyphenyl/-1,3,4-thiadiazole To a suspension of 5.53 g (0.0125 moles) of 2-(5-amino-3-diallylamino-1H-1,2,4-triazole-1-yl)-N'-/4-(3-dimethylaminopropoxy)benzylidene/carbothiohydrazide in 30 ml of tetrahydrofuran, 3.18 g (0.014 moles) of DDQ are added at 25° C. under stirring and cooling, and the suspension is stirred at room temperature for further 4 hours. From the reaction mixture, the tetrahydrofuran is removed by evaporation under reduced pressure, to the residue 50 ml of 5% aqueous sodium hydroxide solution are added, and the mixture is stirred for a further hour. The product precipitated is filtered, washed with 5% aqueous sodium hydroxide solution, then with several portions of water until neutrality, finally with acetonitrile.

Thus, 3.72 g (67.5%) of the title compound are obtained. M.p. (after chromatography on a Kieselgel 60 H layer): 138–141° C.

EXAMPLE 80

2-(5-Amino-3-piperidino-1H-1,2,4-triazole-1-yl)-5-/4-(3-dimethylamino)propoxyphenyl/-1,3,4-thiadiazole To a suspension of 4.30 g (0.01 moles) of 2-(5-amino-3-piperidino-1H-1,2,4-triazole-1-yl)-N'-/4-(3-dimethylaminopropoxy)benzylidene/carbothiohydrazide in 25 ml of tetrahydrofuran, 2.50 g (0.011 moles) of DDQ are added at 25° C. under stirring and cooling, and the suspension is stirred at room temperature for further 5 hours. From the reaction mixture, the tetrahydrofuran is removed by evaporation under reduced pressure, to the residue 30 ml of 5% aqueous sodium hydroxide solution are added, and the mixture is stirred for a further hour. The product precipitated is filtered, washed with 5% aqueous sodium hydroxide solution, then with several portions of water until neutrality, finally with acetonitrile.

Thus, 3.28 g (76.6%) of the title compound are obtained. M.p. (after recrystallization from acetonitrile): 185–189° C.

EXAMPLE 81

2-(5-Amino-3-piperidino-1H-1,2,4-triazole-1-yl)-5-[2-/3-(4-methylpiperidine-1-yl)-propoxy/phenyl]-1,3,4-thiadiazole A mixture of 3.25 g (0.007 moles) of 2-(5-amino-3-piperidino-1H-1,2,4-triazole-1-yl)-5-/2-(3-bromopropoxy)phenyl/-1,3,4-thiadiazole and 11.4 g (0.115 moles) of 4-methylpiperidine is stirred at 130° C. for 2 hours. After cooling, the excess of 4-methylpiperidine is distilled off under reduced pressure, to the residue 40 ml of water are added, drop by drop, and the crystals precipitated are filtered.

Thus, 3.22 g (95.3%) of the title compound are obtained. M.p. (after recrystallization from acetonitrile): 155–159° C.

EXAMPLE 82

2-(5-Amino-3-methylthio-1H-1,2,4-triazole-1-yl)-5-/2-(3-heptamethylenemine-1-ylpropoxy)phenyl/-1,3,4-thiadiazole A mixture of 2.56 g (0.006 moles) of 2-(5-amino-3-methylthio-1H-1,2,4-triazole-1-yl)-5-/2-(3-bromopropoxy)

phenyl/-1,3,4-thiadiazole and 9.92 g (0.0883 moles) of heptamethyleneimine is stirred at 120° C. for 3 hours. After cooling, the excess of heptamethyleneimine is distilled off under reduced pressure, to the residue 40 ml of water are added, drop by drop, and the crystals precipitated are filtered.

Thus, 1.7 g (61.6%) of the title compound are obtained. M.p. (after recrystallization from acetonitrile): 152–157° C.

EXAMPLE 83

2-(5-Amino-3-methylthio-1H-1,2,4-triazole-1-yl)-5-/2-(3-heptamethyleneimine-1-ylpropoxy)phenyl/-1,3, 4-thiadiazole hydrochloride 0.46 g (0.001 moles) of 2-(5-Amino-3-methylthio-1H-1, 2,4-triazole-1-yl)-5-/2-(3-heptamethyleneimine-1-ylpropoxy)phenyl/-1,3,4-thiadiazole base obtained as described in Example 60 are dissolved in 20 ml of methanol, and to the solution 5 ml of ethanol containing 20% by w/v of hydrogen chloride are added. After cooling, the crystals precipitated are filtered, washed with cold ethanol.

Thus, 0.44 g (88.6%) of the title compound are obtained. M.p.: 282–286° C.

EXAMPLE 84

2-(5-Amino-3-methylthio-1H-1,2,4-triazole-1-yl)-5-/2-(3-thiomorpholinopropoxy)phenyl/-1,3,4-thiadiazole A mixture of 3.43 g (0.008 moles) of 2-(5-amino-3-methylthio-1H-1,2,4-triazole-1-yl)-5-/2-(3-bromopropoxy)phenyl/-1,3,4-thiadiazole and 6.38 g (0.062 moles) of thiomorpholine is stirred at 120° C. for 8 hours. After cooling, the excess of thiomorpholine is distilled off under reduced pressure, to the residue 40 ml of water are added, drop by drop, and the crystals precipitated are filtered.

Thus, 3.32 g (92.3%) of the title compound are obtained. M.p. (after chromatography on a Kieselgel 60 H layer, then recrystallization from tetrahydrofuran): 196–199° C.

EXAMPLE 85

2-(5-Amino-3-methylthio-1H-1,2,4-triazole-1-yl)-5-/4-(3-dimethylaminopropoxy)phenyl/-1,3,4-thiadiazole 1.71 g (0.004 moles) of 2-(5-amino-3-methylthio-1H-1, 2,4-triazole-1-yl)-5-/4-(3-dimethylaminopropoxy)phenyl/-1,3,4-thiadiazole obtained as described in Example 28 are suspended in 100 ml of chloroform. 2 ml of triethylamine are added to the suspension that is stirred for 5 minutes. Then, 50 ml of water are added to the suspension, the phases are separated, the organic phase is extracted with a further portion of water, dried, and evaporated to dryness. The residue is subjected to chromatography on a Kieselgel 60 H layer, then recrystallized from acetonitrile.

Thus, 1.46 g (93.2%) of the title base are obtained. M.p.: 192–193° C.

EXAMPLE 86

2-(5-Amino-3-methylthio-1H-1,2,4-triazole-1-yl)-5-/2-(3-dimethylaminopropoxy)phenyl/-1,3,4-thiadiazole 2.19 g (0.004 moles) of 2-(5-amino-3-methylthio-1H-1, 2,4-triazole-1-yl)-5-(2-hydroxyphenyl)-1,3,4-thiadiazole tetrabutylammonium salt are dissolved in 15 ml of acetonitrile at 80° C., and to the solution obtained a solution of 3.94 ml (0.01 moles) of 40% by w/v 3-dimethylaminopropyl chloride solution in xylene are added under stirring. The reaction mixture is stirred at 100° C. for 1 hour. After cooling, the reaction mixture is evaporated to dryness under reduced pressure, the residue is dissolved in chloroform, extracted with 1N sodium hydroxide solution, then with water, dried over anhydrous sodium sulfate, and evaporated to dryness.

Thus, 1.05 g (67%) of the title compound are obtained. M.p. (after chromatography on a Kieselgel 60 H layer): 177–179° C.

EXAMPLE 87

2-(5-Amino-3-piperidino-1H-1,2,4-triazole-1-yl)-5-/2-(4-morpholinobutoxy)phenyl/-1,3,4-thiadiazole A mixture of 0.48 g (0.001 moles) of 2-(5-amino-3-piperidino-1H-1,2,4-triazole-1-yl)-5-/2-(4-bromobutoxy)phenyl/-1,3,4-thiadiazole and 0.87 g (0.01 moles) of morpholine is stirred at 100° C. for 0.5 hours. To the reaction mixture, 5 ml of water are added, and the mixture is stirred for 30 minutes. The crystals precipitated are filtered, washed with ether, then with acetonitrile.

Thus, 0.42 g (86.6%) of the title compound are obtained. M.p. (after chromatography on a Kieselgel 60 H layer, then recrystallization from acetonitrile): 148–150° C.

EXAMPLE 88

2-(5-Benzylamino-3-methylthio-1H-1,2,4-triazole-1-yl)-5-/2-(3-dimethylamino)propoxyphenyl/-1,3,4-thiadiazole To a suspension of 4.56 g (0.01 moles) of 2-(5-benzylamino-3-methylthio-1H-1,2,4-triazole-1-yl)-N'-/2-(3-dimethylaminopropoxy)benzylidene/carbothiohydrazide in 50 ml of tetrahydrofuran, 2.73 g (0.012 moles) of DDQ are added at 25° C. under stirring and cooling, and the suspension is stirred at room temperature for a further hour. From the reaction mixture, the tetrahydrofuran is removed by evaporation under reduced pressure, to the residue 30 ml of 5% sodium hydroxide solution are added, and the mixture is stirred for an hour. The product precipitated is filtered, washed with 5% sodium hydroxide solution, then with several portions of water until neutrality, finally with acetonitrile.

Thus, 4.20 g (87.2%) of the title compound are obtained. M.p.: 127–128° C.

EXAMPLE 89

2-(5-Amino-3-piperidino-1H-1,2,4-triazole-1-yl)-5-/3-methoxy-4-(3-morpholinopropoxy)phenyl/-1,3,4-thiadiazole A mixture of 0.49 g (0.001 moles) of 2-(5-amino-3-piperidino-1H-1,2,4-triazole-1-yl)-5-/3-methoxy-4-(3-bromopropoxy)phenyl/-1,3,4-thiadiazole and 1 g (0.0115 moles) of morpholine is stirred at 100° C. for 2 hours. After cooling, the excess of morpholine is removed by evaporation under reduced pressure, to the residue 40 ml of water are added, drop by drop. The crystals precipitated are filtered, washed with 5% by w/v sodium hydroxide solution, water, and acetonitrile.

Thus, 0.21 g (42%) of the title-compound are obtained that is purified by chromatography on a Kieselgel 60 H layer, then recrystallization from acetonitrile.

EXAMPLE 90

2-(5-Amino-3-piperidino-1H-1,2,4-triazole-1-yl)-5-
{2-[2-/2-ethyl-2-(2-hydroxyethyl)amino/ethoxy]
phenyl}-1,3,4-thiadiazole A mixture of 4.50 g (0.01 moles) of 2-(5-amino-3-piperidino-1H-1,2,4-triazole-1-yl)-5-/2-(2-bromoethoxy)phenyl/-1,3,4-thiadiazole and 10 ml of ethylaminoethanol is stirred at 120° C. for 3 hours. To the melt obtained, 30 ml of water are added, and the product is allowed to crystallize. After cooling, the separated crystals are filtered, washed with water, then with acetonitrile.

Thus, 4.19 g (91.4%) of the title compound are obtained. M.p. (after chromatography on a Kieselgel 60 H layer, then recrystallization from acetonitrile): 169–172° C.

EXAMPLE 91

2-(5-Amino-3-piperidino-1H-1,2,4-triazole-1-yl)-5-
[2-/2-(2-morpholinoethyl)amino/ethoxy]phenyl-1,3,
4-thiadiazole A mixture of 4.50 g (0.01 moles) of 2-(5-amino-3-piperidino-1H-1,2,4-triazole-1-yl)-5-/2-(2-bromoethoxy)phenyl/-1,3,4-thiadiazole and 13 g (0.1 moles) of 2-aminoethylmorpholine is stirred at 120° C. for 3 hours. To the melt obtained, 30 ml of water are added, and the product is allowed to crystallize. After cooling, the separated crystals are filtered, washed with water, then with acetonitrile.

Thus, 4.52 g (90.5%) of the title compound are obtained. M.p. (after chromatography on a Kieselgel 60 H layer, then recrystallization from acetonitrile): 162–164° C.

EXAMPLE 92

2-(5-Amino-3-piperidino-1H-1,2,4-triazole-1-yl)-5-
{2-[2-/2-bis(2-hydroxyethyl)amino/ethoxy]phenyl}-
1,3,4-thiadiazole A mixture of 4.50 g (0.01 moles) of 2-(5-amino-3-piperidino-1H-1,2,4-triazole-1-yl)-5-/2-(2-bromoethoxy)phenyl/-1,3,4-thiadiazole and 10 ml of diethanolamine is stirred at 120° C. for 3 hours. To the reaction mixture, 50 ml of water are added, and the product is allowed to crystallize. After cooling, the separated crystals are filtered, washed with water, then with acetonitrile.

Thus, 4.42 g (93.2%) of the title compound are obtained. M.p. (after chromatography on a Kieselgel 60 H layer, then recrystallization from acetonitrile): 181–184° C.

EXAMPLE 93

2-(5-Amino-3-piperidino-1H-1,2,4-triazole-1-yl)-5-
{2-[2-/2-(3,4-dimethoxyphenyl)ethylamino/ethoxy]
phenyl}-1,3,4-thiadiazole A mixture of 4.50 g (0.01 moles) of 2-(5-amino-3-piperidino-1H-1,2,4-triazole-1-yl)-5-/2-(2-bromoethoxy)phenyl/-1,3,4-thiadiazole and 9.4 g of N-methyl-N-/2-(3,4-dimethoxyphenyl)ethyl/-amine is stirred at 120° C. for 1 hour. From the reaction mixture, the excess of amine is evaporated under reduced pressure, to the residue 40 ml of water are added, and the mixture is allowed to crystallize. The crystals precipitated are filtered, washed with water, then with diethyl ether.

Thus, 4.01 g (71.0%) of the title compound are obtained. M.p. (after chromatography on a Kieselgel 60 H layer, then recrystallization from acetonitrile): 104–106° C.

EXAMPLE 94

2-(5-Amino-3-piperidino-1H-1,2,4-triazole-1-yl)-5-
{4-[2-/2-ethyl-2-(hydroxyethyl)amino/ethoxy]
phenyl}-1,3,4-thiadiazole A mixture of 3.60 g (0.008 moles) of 2-(5-amino-3-piperidino-1H-1,2,4-triazole-1-yl)-5-/2-(2-bromoethoxy)phenyl/-1,3,4-thiadiazole and 7.13 g (7.8 ml, 0.08 moles) of ethylaminoethanol is stirred at 120° C. for 1 hour. To the melt obtained, 40 ml of water are added, and the product is allowed to crystallize. After cooling, the separated crystals are filtered, washed with water, then with acetonitrile.

Thus, 3.45 g (94.2%) of the title compound are obtained. M.p. (after chromatography on a Kieselgel 60 H layer, then recrystallization from acetonitrile): 181–184° C.

EXAMPLE 95

2-(5-Amino-3-piperidino-1H-1,2,4-triazole-1-yl)-5-
{4-[2-/bis(2-hydroxyethyl)amino/ethoxy]phenyl}-1,
3,4-thiadiazole A mixture of 3.60 g (0.008 moles) of 2-(5-amino-3-piperidino-1H-1,2,4-triazole-1-yl)-5-/4-(2-bromoethoxy)phenyl/-1,3,4-thiadiazole and 8.41 g of diethanolamine is stirred at 120° C. for 3 hours. To the reaction mixture, 40 ml of water are added, and the product is allowed to crystallize. After cooling, the separated crystals are filtered, washed with water, then with acetonitrile.

Thus, 3.52 g (92.8%) of the title compound are obtained. M.p. (after chromatography on a Kieselgel 60 H layer, then recrystallization from acetonitrile): 179–182° C.

EXAMPLE 96

2-(5-Amino-3-piperidino-1H-1,2,4-triazole-1-yl)-5-
{4-[2-/2-(morpholinoethyl)amino/ethoxy]phenyl}-1,
3,4-thiadiazole A mixture of 3.60 g (0.008 moles) of 2-(5-amino-3-piperidino-1H-1,2,4-triazole-1-yl)-5-/4-(2-bromoethoxy)phenyl/-1,3,4-thiadiazole and 10.74 g (10.5 ml, 0.08 moles) of 2-aminoethylmorpholine is stirred at 120° C. for 1 hour. To the melt obtained, 30 ml of water are added, and the product is allowed to crystallize. After cooling, the separated crystals are filtered, washed with water, then with acetonitrile.

Thus, 3.74 g (93.7%) of the title compound are obtained. M.p. (after chromatography on a Kieselgel 60 H layer, then recrystallization from acetonitrile): 175–177° C.

EXAMPLE 97

2-(5-Amino-3-piperidino-1H-1,2,4-triazole-1-yl)-5-
{4-[2-methyl-2-/2-(3,4-dimethoxyphenyl)
ethylamino/ethoxy]phenyl}-1,3,4-thiadiazole A mixture of 3.60 g (0.008 moles) of 2-(5-amino-3-piperidino-1H- 1,2,4-triazole-1-yl)-5-/4-(2-bromoethoxy)phenyl/-1,3,4-thiadiazole and 9.21 g (0.047 moles) of N-methyl-N-/2-(3,4-dimethoxyphenyl)ethyl/-amine is stirred at 120° C. for 1 hour. After cooling, 30 ml of methanol are added, drop by drop, to the reaction mixture, the separated crystals are filtered, washed with water, then with diethyl ether.

Thus, 4.02 g (89.1%) of the title compound are obtained. M.p. (after chromatography on a Kieselgel 60 H layer, then recrystallization from acetonitrile): 133–136° C.

EXAMPLE 98

2-(5-Amino-3-methylthio-1H-1,2,4-triazole-1-yl)-5-{2-[3-methyl-3-/2-(3,4-dimethoxyphenylethyl)amino/propoxy]phenyl}-1,3,4-thiadiazole A mixture of 3.27 g (0.008 moles) of 2-(5-amino-3-methylthio-1H-1,2,4-triazole-1-yl)-5-/2-(3-bromopropoxy)phenyl/-1,3,4-thiadiazole and 9.21 g (0.047 moles) of N-methyl-N-/2-(3,4-dimethoxyphenyl)propyl/amine is stirred at 140° C. for 1 hour. After cooling, 40 ml of water are added, drop by drop, to the reaction mixture, the separated crystals are filtered, washed with water, then with diethyl ether.

Thus, 3.38 g (78%) of the title compound are obtained. M.p. (after chromatography on a Kieselgel 60 H layer, then recrystallization from acetonitrile): 138–140° C.

EXAMPLE 99

2-(5-Amino-3-piperidino-1H-1,2,4-triazole-1-yl)-5-{2-[3-methyl-3-/2-(3,4-dimethoxyphenylethyl)amino/-propoxy]phenyl}-1,3,4-thiadiazole A mixture of 3.60 g (0.008 moles) of 2-(5-amino-3-piperidino-1H-1,2,4-triazole-1-yl)-5-/2-(3-bromopropoxy)phenyl/-1,3,4-thiadiazole and 9.21 g (0.047 moles) of N-methyl-N-/3-(3,4-dimethoxyphenyl)propyl/amine is stirred at 140° C. for 1 hour. After cooling, 40 ml of water are added, drop by drop, to the reaction mixture, the separated crystals are filtered, washed with water, then with diethyl ether.

Thus, 4.68 g (81%) of the title compound are obtained. M.p. (after chromatography on a Kieselgel 60 H layer, then recrystallization from acetonitrile): 125–127° C.

EXAMPLE 100

2-(5-Amino-3-methylthio-1H-1,2,4-triazole-1-yl)-5-{2-[3-(2-morpholinoethyl)amino/-propoxy]phenyl}-1,3,4-thiadiazole A mixture of 3.79 g (0.01 moles) of 2-(5-amino-3-methylthio-1H-1,2,4-triazole-1-yl)-5-/2-(3-bromopropoxy)phenyl/- 1,3,4-thiadiazole and 3.90 g (0.03 moles) of 2-morpholinoethylamine is stirred at 160° C. for 0.3 hours. After cooling, 40 ml of water are added, drop by drop, to the reaction mixture, the separated crystals are filtered, washed with water, then with diethyl ether.

Thus, 3.91 g (82%) of the title compound are obtained. M.p. (after chromatography on a Kieselgel 60 H layer, then recrystallization from acetonitrile): 170–172° C.

EXAMPLE 101

2-/5-Amino-3-(1-methylethylthio)-1H-1,2,4-triazole-1-yl/-5-{2-[3-methyl-3-/2-(3,4-dimethoxyphenylethyl)amino/propoxy]-phenyl}-1,3,4-thiadiazole A mixture of 4.07 g (0.01 moles) of 2-/5-amino-3-(1-methylethylthio)-1H-1,2,4-triazole-1-yl/-5-/2-(3-bromopropoxy)phenyl/-1,3,4-thiadiazole and 5.88 g (0.03 moles) of N-methyl-N-/2-(3,4-dimethoxyphenyl)propyl/-amine is stirred at 140° C. for 1 hour. After cooling, 40 ml of water are added, drop by drop, to the reaction mixture, the separated crystals are filtered, washed with water, then with diethyl ether.

Thus, 4.44 g (78%) of the title compound are obtained. M.p. (after chromatography on a Kieselgel 60 H layer, then recrystallization from acetonitrile): 133–134° C.

EXAMPLE 102

2-(5-Amino-3-methylthio-1H-1,2,4-triazole-1-yl)-5-[2-/3-(2-hydroxyethylamino)propoxy/phenyl]-1,3,4-thiadiazole A mixture of 3.79 g (0.01 moles) of 2-(5-amino-3-methylthio-1H-1,2,4-triazole-1-yl)-5-/2-(3-bromopropoxy)phenyl/-1,3,4-thiadiazole and 1.83 g (0.03 moles) of 2-hydroxyethylamine is stirred at 140° C. for 1 hour. After cooling, 40 ml of water are added, drop by drop, to the reaction mixture, the separated crystals are filtered, washed with water, then with diethyl ether.

Thus, 2.90 g (71%) of the title compound are obtained. M.p. (after chromatography on a Kieselgel 60 H layer, then recrystallization from acetonitrile): 160–162° C.

EXAMPLE 103

2-(5-Amino-3-methylthio-1H-1,2,4-triazole-1-yl)-5-[2-/3-(1,2,2-trimethylpropylamino)-propoxy/phenyl]-1,3,4-thiadiazole A mixture of 3.79 g (0.01 moles) of 2-(5-amino-3-methylthio-1H-1,2,4-triazole-1-yl)-5-/2-(3-bromopropoxy)phenyl/-1,3,4-thiadiazole and 1.83 g (0.03 moles) of 1,2,2-trimethylpropylamine is stirred at 140° C. for 1 hour. After cooling, 40 ml of water are added, drop by drop, to the reaction mixture, the separated crystals are filtered, washed with water, then with diethyl ether.

Thus, 3.09 g (69%) of the title compound are obtained. M.p. (after chromatography on a Kieselgel 60 H layer, then recrystallization from acetonitrile): 174–176° C.

EXAMPLE 104

2-/5-Amino-3-(1-methylethylthio)-1H-1,2,4-triazole-1-yl/-5-[2-/3-(1,2,2-trimethylpropylamino)propoxy/phenyl]-1,3,4-thiadiazole A mixture of 4.07 g (0.01 moles) of 2-/5-amino-3-(1-methylethylthio)-1H-1,2,4-triazole-1-yl/-5-/2-(3-bromopropoxy)phenyl/-1,3,4-thiadiazole and 1.83 g (0.03 moles) of 1,2,2-trimethylpropylamine is stirred at 100° C. for 48 hours. After cooling, 40 ml of water are added, drop by drop, to the reaction mixture, the separated crystals are filtered, washed with water, then with diethyl ether.

Thus, 4.09 g (86%) of the title compound are obtained. M.p. (after chromatography on a Kieselgel 60 H layer, then recrystallization from acetonitrile): 184–185° C.

EXAMPLE 105

2-(5-Amino-3-methylthio-1H-1,2,4-triazole-1-yl)-5-{3-[3-methyl-3-/2-(3,4-dimethoxyphenylethyl)amino/propoxy]phenyl}-1,3,4-thiadiazole A mixture of 3.79 g (0.01 moles) of 2-(5-amino-3-methylthio-1H-1,2,4-triazole-1-yl)-5-/3-(3-bromopropoxy)phenyl/-1,3,4-thiadiazole and 5.88 g (0.03 moles) of N-methyl-N-/2-(3,4-dimethoxyphenyl)propyl/amine is stirred at 140° C. for 0.5 hours. After cooling, 40 ml of water are added, drop by drop, to the reaction mixture, the separated crystals are filtered, washed with water, then with diethyl ether.

Thus, 3.95 g (73%) of the title compound are obtained. M.p. (after chromatography on a Kieselgel 60 H layer, then recrystallization from acetonitrile): 112–114° C.

EXAMPLE 106

2-/5-Amino-3-(1-methylethylthio)-1H-1,2,4-triazole-1-yl/-5-{2-[3-methyl-3-/2-(3,4-dimethoxyphenylethyl)amino/propoxy]-phenyl}-1,3,4-thiadiazole A mixture of 4.07 g (0.01 moles) of 2-/5-amino-3-(1-methylethylthio)-1H-1,2,4-triazole-1-yl/-5-/2-(3- bromopropoxy)phenyl/-1,3,4-thiadiazole and 5.88 g (0.03 moles) of N-methyl-N-/2-(3,4-dimethoxyphenyl)propyl/-amine is stirred at 140° C. for 0.5 hours. After cooling, 40 ml of water are added, drop by drop, to the reaction mixture, the separated crystals are filtered, washed with water, then with diethyl ether.

Thus, 4.05 g (71%) of the title compound are obtained. M.p. (after chromatography on a Kieselgel 60 H layer, then recrystallization from acetonitrile): 98–100° C.

EXAMPLE 107

2-(5-Amino-3-methylthio-1H-1,2,4-triazole-1-yl)-5-{4-[3-methyl-3-/2-(3,4-dimethoxyphenylethyl)amino/propoxy]phenyl}-1,3,4-thiadiazole A mixture of 3.79 g (0.01 moles) of 2-(5-amino-3-methylthio-1H-1,2,4-triazole-1-yl)-5-/4-(3-bromopropoxy)phenyl/-1,3,4-thiadiazole and 5.88 g (0.03 moles) of N-methyl-N-/2-(3,4-dimethoxyphenyl)propyl/amine is stirred at 140° C. for 1 hour. After cooling, 40 ml of water are added, drop by drop, to the reaction mixture, the separated crystals are filtered, washed with water, then with diethyl other.

Thus, 3.17 g (68%) of the title compound are obtained. M.p. (after chromatography on a Kieselgel 60 H layer, then recrystallization from acetonitrile): 138–140° C.

EXAMPLE 108

2-(5-Amino-3-methylthio-1H-1,2,4-triazole-1-yl)-5-{4-[3-methyl-3-/2-(3,4-dimethoxyphenylethyl)amino/propoxy]phenyl}-1,3,4-thiadiazole A mixture of 3.79 g (0.01 moles) of 2-(5-amino-3methylthio-1H-1,2,4-triazole-1-yl)-5-/4-(3-bromopropoxy)phenyl/-1,3,4-thiadiazole and 5.88 g (0.03 moles) of N-methyl-N-/2-(3,4-dimethoxyphenyl)propyl/amine is stirred at 140° C. for 0.5 hours. After cooling, 40 ml of water are added, drop by drop, to the reaction mixture, the separated crystals are filtered, washed with water, then with diethyl ether.

Thus, 4.73 g (83%) of the title compound are obtained. M.p. (after chromatography on a Kieselgel 60 H layer, then recrystallization from acetonitrile): 127–129° C.

EXAMPLE 109

2-(5-Amino-3-methylthio-1H-1,2,4-triazole-1-yl)-5-[4-/3-(1,2,2-trimethylpropylamino)propoxy/phenyl]-1,3,4-thiadiazole A mixture of 3.79 g (0.01 moles) of 2-(5-amino-3-methylthio-1H-1,2,4-triazole-1-yl)-5-/4-(3-bromopropoxy)phenyl/-1,3,4-thiadiazole and 1.83 g (0.03 moles) of 1,2,2-trimethylpropylamine is stirred at 100° C. for 48 hours. After cooling, 40 ml of water are added, drop by drop, to the reaction mixture, the separated crystals are filtered, washed with water, then with diethyl ether.

Thus, 3.27 g (73%) of the title compound are obtained. M.p. (after chromatography on a Kieselgel 60 H layer, then recrystallization from acetonitrile): 154–155° C.

EXAMPLE 110

2-/5-Amino-3-(1-methylethylthio)-1H-1,2,4-triazole-1-yl/-5-[4-/3-(1,2,2-trimethylpropylamino)propoxy/phenyl]-1,3,4-thiadiazole A mixture of 4.07 g (0.01 moles) of 2-/5-amino-3-(1-methylethylthio)-1H-1,2,4-triazole-1-yl/-5-/4-(3-bromopropoxy)phenyl/-1,3,4-thiadiazole and 1.83 g (0.03 moles) of 1,2,2-trimethylpropylamine is stirred at 100° C. for 48 hours. After cooling, 40 ml of water are added, drop by drop, to the reaction mixture, the separated crystals are filtered, washed with water, then with diethyl ether.

Thus, 3.76 g (79%) of the title compound are obtained. M.p. (after chromatography on a Kieselgel 60 H layer, then recrystallization from acetonitrile): 154–156° C.

EXAMPLE 111

2-(5-Amino-3-piperidino-1H-1,2,4-triazole-1-yl)-5-{2-[2-/2-butyl-2-(2-hydroxyethyl)amino/ethoxy]phenyl}-1,3,4-thiadiazole A mixture of 4.65 g (0.013 moles) of 2-(5-amino-3-piperidino-1H-1,2,4-triazole-1-yl)-5-/2-(2-bromoethoxy)phenyl/-1,3,4-thiadiazole and 10 ml of butylaminoethanol is stirred at 110° C. for 2 hours. To the melt obtained, 30 ml of water are added, and the mixture is allowed to crystallize. After cooling, the separated crystals are filtered, washed with water, then with acetonitrile.

Thus, 4.6 g (91.8%) of the title compound are obtained. M.p. (after chromatography on a Kieselgel 60 H layer, then recrystallization from acetonitrile): 152–155° C.

EXAMPLE 112

2-(5-Amino-3-piperidino-1H-1,2,4-triazole-1-yl)-5-[3-/2-ethyl-2-(2-hydroxyethylamino)-ethoxy/phenyl]-1,3,4-thiadiazole A mixture of 4.50 g (0.01 moles) of 2-(5-amino-3-piperidino-1H-1,2,4-triazole-1-yl)-5-/3-(2-bromoethoxy)phenyl/-1,3,4-thiadiazole and 10 ml of ethylaminoethanol is stirred at 110° C. for 1.5 hours. To the reaction mixture, 40 ml of water are added, and the mixture is allowed to crystallize. After cooling, the separated crystals are filtered, washed with water, then with acetonitrile.

Thus, 3.9 g (85.0%) of the title compound are obtained. M.p. (after chromatography on a Kieselgel 60 H layer, then recrystallization from acetonitrile): 138–141° C.

EXAMPLE 113

2-(5-Amino-3-piperidino-1H-1,2,4-triazole-1-yl)-5-[2-/3-bis(2-hydroxyethyl)amino-ethoxy/phenyl]-1,3,4-thiadiazole A mixture of 4.50 g (0.01 moles) of 2-(5-amino-3-piperidino-1H-1,2,4-triazole-1-yl)-5-/3-(2-bromoethoxy)phenyl/-1,3,4-thiadiazole and 10 ml of diethanolamine is stirred at 120° C. for 2 hours. To the reaction mixture, 40 ml of water are added, and the mixture is allowed to crystallize. After cooling, the separated crystals are filtered, washed with water, then with acetonitrile.

Thus, 4.22 g (88.9%) of the title compound are obtained. M.p. (after chromatography on a Kieselgel 60 H layer, then recrystallization from acetonitrile): 152–155° C.

EXAMPLE 114

2-(5-Amino-3-piperidino-1H-1,2,4-triazole-1-yl)-5-[4-/3-(2-morpholinoethyl)aminoethoxy/phenyl]-1,3,4-thiadiazole A mixture of 4.50 g (0.01 moles) of 2-(5-amino-3-piperidino-1H-1,2,4-triazole-1-yl)-5-/3-(2-bromoethoxy)phenyl/-1,3,4-thiadiazole and 13.2 g (0.1 moles) of 2-aminoethylmorpholine is stirred at 120° C. for 1.5 hours. To the melt obtained, 40 ml of water are added, and the mixture is allowed to crystallize. After cooling, the separated crystals are filtered, washed with water, then with acetonitrile.

Thus, 4.27 g (85%) of the title compound are obtained. M.p. (after chromatography on a Kieselgel 60 H layer, then recrystallization from tetrachloromethane): 136–137° C.

EXAMPLE 115

2-(5-Amino-3-piperidino-1H-1,2,4-triazole-1-yl)-5-{3-[2-methyl-2-/2(3,4-dimethoxyphenyl)ethylamino/ethoxy]phenyl}-1,3,4-thiadiazole A mixture of 4.50 g (0.01 moles) of 2-(5-amino-3-piperidino-1H-1,2,4-triazole-1-yl)-5-/3-(2-bromoethoxy)phenyl/-1,3,4-thiadiazole and 9.4 g of N-methyl-N-/2-(3,4-dimethoxyphenyl)ethyl/amine is stirred at 120° C. for 1 hour. From the reaction mixture, the excess of amine is evaporated under reduced pressure, to the residue, a mixture of 30 ml of water and 30 ml of methanol is added, and the mixture is allowed to crystallize. The separated crystals are filtered, washed with water, then with diethyl ether.

Thus, 5.1 g (90.3%) of the title compound are obtained. M.p. (after chromatography on a Kieselgel 60 H layer, then recrystallization from tetrachloromethane): 147–149° C.

EXAMPLE 116

2-/5-Benzylamino-3-(1-methylethylthio)-1H-1,2,4-triazole-1-yl/-5-[2-/3-(2-morpholinoethylamino)propoxy/phenyl]-1,3,4-thiadiazole A mixture of 2.00 g (0.0036 moles) of 2-(5-benzylamino)-3-(1-methylethylthio)-1H-1,2,4-triazole-1-yl)-5-/2-(3-bromopropoxy)phenyl/-1,3,4-thiadiazole and 4.56 g (0.035 moles) of 2-morpholinoethylamine is stirred at 80° C. for 7 hours. After cooling, 98 ml of water and 2 ml of ethyl acetate are added, drop by drop, to the reaction mixture, then the mixture is stirred at room temperature for 1.5 hours. The separated crystals are filtered, washed with water, then with diethyl ether.

Thus, 2.11 g (96.9%) of the title compound are obtained. M.p.: 61–63° C.

EXAMPLE 117

2-/5-(4-Chlorobenzylamino)-3-(1-methylethylthio)-1H-1,2,4-triazole-1-yl/-5-[2-/3-(2-morpholinoethylamino)propoxy/phenyl]-1,3,4-thiadiazole A mixture of 1.90 g (0.0032 moles) of 2-(5-amino)-3-(1-methylethylthio)-1H-1,2,4-triazole-1-yl)-5-/2-(3-bromopropoxy)phenyl/-1,3,4-thiadiazole and 3.80 g (0.029 moles) of 2-morpholinoethylamine is stirred at 80° C. for 7 hours. After cooling, 98 ml of water and 2 ml of ethyl acetate are added, drop by drop, to the reaction mixture, then the mixture is stirred at room temperature for 1.5 hours. The separated crystals are filtered, washed with water, then with diethyl ether.

Thus, 1.96 g (95.2%) of the title compound are obtained. M.p.: 118–120° C.

EXAMPLE 118

2-/5-(4-Chlorobenzylamino)-3-methylthio-1H-1,2,4-triazole-1-yl/-5-[2-/3-(2-morpholinoethylamino)propoxy/phenyl]-1,3,4-thiadiazole A mixture of 5.00 g (0.009 moles) of 2-/5-(4-chlorobenzylamino)-3-methylthio-1H-1,2,4-triazole-1-yl/-5-/2-(3-bromopropoxy)phenyl/-1,3,4-thiadiazole and 5.90 g (0.045 moles) of 2-morpholinoethylamine is stirred at 80° C. for 7 hours. After cooling, 98 ml of water and 2 ml of ethyl acetate are added, drop by drop, to the reaction mixture, then the mixture is stirred at room temperature for 1.5 hours. The separated crystals are filtered, washed with water, then with diethyl ether.

Thus, 4.39 g (80.6%) of the title compound are obtained. M.p.: 124–126° C.

EXAMPLE 119

2-(5-Amino-3-methylthio-1H-1,2,4-triazole-1-yl)-5-{2-[3-methyl-3-/2-(3,4-dimethoxyphenylethyl)amino/propoxy]phenyl}-1,3,4-thiadiazole A mixture of 0.043 g (0.0001 moles) of 2-(5-amino-3-methylthio-1H-1,2,4-triazole-1-yl)-5-/2-(3-bromopropoxy)phenyl/-1,3,4-thiadiazole and 0.195 g (0.001 moles) of N-methyl-N-/2-(3,4-dimethoxyphenyl)propyl/amine is stirred at 100° C. for 15 minutes. The reaction mixture is allowed to stand at room temperature for 24 hours. To the reaction mixture, 3 ml of water are added, drop by drop, to the reaction mixture, the separated crystals are stirred for 1 hour, then filtered, washed with water, acetonitrile. then with diethyl ether.

Thus, 0.046 g (85.2%) of the title compound are obtained. M.p.: 138–141° C.

EXAMPLE 120

2-(5-Amino-3-methylthio-1H-1,2,4-triazole-1-yl)-5-{2-[3-methyl-3-/2-(3,4-dimethoxyphenyl-ethyl)amino/-propoxy]phenyl}-1,3,4-thiadiazole A solution of 1.8 g (0.0066 moles) of 2-(5-amino-3-methylthio-1H-1,2,4-triazole-1-yl)-5-(2-hydroxyphenyl)-1,3,4-thiadiazole tetrabutylammonium salt and 1.10 g (0.002 moles) of N-methyl-N-/2-(3,4-dimethoxyphenyl)ethyl/-N-(3-chloropropyl)amine in 10 ml of acetonitrile is stirred at room temperature for 67 hours. The product separated is filtered, washed with some acetonitrile.

Thus, 0.79 g (73.1%) of the title compound are obtained. M.p. (after chromatography over a column filled with alumina using hexane/chloroform mixtures of increasing polarity as the eluent): 147.5–148.5° C.

EXAMPLE 121

2-/5-Amino-3-(n-hexylthio)-1H-1,2,4-triazol-yl/-5-{2-[3-methyl-3-/2-(3,4-dimethoxyphenylethyl)amino/propoxy]phenyl}-1,3,4-thiadiazole A solution of 0.742 g (0.0012 moles) of 2-/5-amino-3-(n-hexylthio)-1H-1,2,4-triazole-1-yl/-5-(2-hydroxyphenyl)-1,3,4-thiadiazole tetrabutylammonium salt and 0.652 g (0.024 moles) of N-methyl-N-/2-(3,4-dimethoxyphenyl)ethyl/-N-(3-chloropropyl)amine in 5 ml of acetonitrile is stirred at room temperature for 8 days. The reaction mixture is evaporated to dryness under reduced pressure, the residue is dissolved in 50 ml of chloroform, the organic solution is extracted with water, dried over anhydrous sodium sulfate, then again evaporated to dryness under reduced pressure.

Thus, 1.11 g of black oil are obtained that is subjected to chromatography over a column filled with alumina using hexane/chloroform mixtures of increasing polarity as the eluent to obtain 0.44 g (44.4%) of the pure title product. M.p.: 106–107.5° C.

EXAMPLE 122

2-(5-Amino-3-methylthio-1H-1,2,4-triazole-1-yl)-5-
{2-[3-methyl-3-/2-(3,4-dimethoxyphenylethyl)
amino/propoxy]phenyl}-1,3,4-thiadiazole To a suspension of 0.435 g (0.0008 moles) of 1-(5-amino-3-methylthio-1H-1,2,4-triazole-1-yl)-N'-{3-[N-/2-(3,4-dimethoxyphenyl)ethyl/-N-methyl]propoxy}benzylidenecarbothiohydrazide in 10 ml of tetrahydrofuran, 0.204 g (0.0009 moles) of DDQ are added at 25° C. under stirring and cooling, then the suspension is stirred at room temperature for a further hour. From the reaction mixture, the tetrahydrofuran is removed under reduced pressure, to the residue 15 ml of 5% aqueous sodium hydroxide solution are added, and the mixture is stirred for 2 hours. The product separated is filtered, washed with 5% aqueous sodium hydroxide solution, then with several portions of water until neutrality.

Thus, 0.39 g (90.1%) of the title compound are obtained. M.p. (after chromatography on an alumina layer): 147–149° C.

EXAMPLE 123

2-(5-Amino-3-piperidino-1H-1,2,4-triazole-1-yl)-5-
[2-/2-methyl-2-(2-hydroxyethylamino)ethoxy/
phenyl]-1,3,4-thiadiazole To a suspension of 3.13 g (0.007 moles) of 1-(5-amino-3-piperidino-1H-1,2,4-triazole-1-yl)-N'-{2-[N-/2-(hydroxyethyl)-N-methyl/-ethoxy]benzylidene}carbothiohydrazide in 30 ml of tetrahydrofuran, 1.75 g (0.0077 moles) of DDQ are added at 25° C. under stirring and cooling, then the suspension is stirred at room temperature for a further hour. From the reaction mixture, the tetrahydrofuran is removed under reduced pressure, to the residue 45 ml of 5% aqueous sodium hydroxide solution are added, and the mixture is stirred for 1 hour. The product separated is filtered, washed with 5% aqueous sodium hydroxide solution, then with several portions of water until neutrality, finally with acetonitrile.

Thus, 2.92 g (93.8%) of the title compound are obtained. M.p. (after chromatography on a Kieselgel H layer): 170–173° C.

EXAMPLE 124

2-(5-Amino-3-methylthio-1H-1,2,4-triazole-1-yl)-5-
[4-/3-(2-morpholinoethylamino)propoxy/phenyl]-1,
3,4-thiadiazole A mixture of 4.1 g (0.009 moles) of 2-(5-amino-3-methylthio-1H-1,2,4-triazole-1-yl)-5-/4-(3-bromopropoxy)phenyl/-1,3,4-thiadiazole and 12.4 g (0.09 moles) of 2-morpholinoethylamine is stirred at 140° C. for 0.3 hours. After cooling, 100 ml of water are added, drop by drop, to the reaction mixture, the precipitated crystals are filtered washed with water, then with diethyl ether.

Thus, 3.41 g (76.8%) of the title compound are obtained. M.p. (after chromatography on a Kieselgel 60 H layer, then recrystallization from acetonitrile): 153–154° C.

EXAMPLE 125

2-(5-Amino-3-dimethylamino-1H-1,2,4-triazole-1-
yl)-5-[4-/3-(2-morpholinoethylamino)propoxy/
phenyl]-1,3,4-thiadiazole A mixture of 0.85 g (0.002 moles) of 2-(5-amino-3-dimethylamino-1H-1,2,4-triazole-1-yl)-5-/2-(3-bromopropoxy)phenyl/-1,3,4-thiadiazole and 2.6 g (0.02 moles) of 2-morpholinoetlhylamine is stirred at 140° C. for 0.3 hours. After cooling, 50 ml of water are added, drop by drop, to the reaction mixture, the precipitated crystals are filtered, washed with water, then with diethyl, ether.

Thus, 0.47 g (49.5%) of the title compound are obtained. M.p. (after chromatography on a Kieselgel 60 H layer, then recrystallization from acetonitrile): 160–162° C.

EXAMPLE 126

2-(5-Amino-3-methylthio-1H-1,2,4-triazole-1-yl)-5-/
2-(2-morpholinoethylaminoethoxy)-phenyl/-1,3,4-
thiadiazole A mixture of 1.45 g (0.0035 moles) of 2-(5-amino-3-methylthio-1H-1,2,4-triazole-1-yl)-5-/2-(2-bromoethoxy)phenyl/-1,3,4-thiadiazole and 4.56 g (0.035 moles) of 2-morpholinoethylamine is stirred at 80° C. for 2 hours. After cooling, 10 ml of water are added, drop by drop, to the reaction mixture, the precipitated crystals are filtered, washed with water, then with diethyl ether.

Thus, 1.48 g (91.9%) of the title compound are obtained. M.p.: 171–174° C.

EXAMPLE 127

2-(5-Amino-3-methylthio-1H-1,2,4-triazole-1-yl)-5-
[2-/2-(3-morpholinopropylamino)-ethoxy/phenyl]-1,
3,4-thiadiazole A mixture of 1.45 g (0.0035 moles) of 2-(5-amino-3-methylthio-1H-1,2,4-triazole-1-yl)-5-/2-(2-bromoethoxy)phenyl/-1,3,4-thiadiazole and 5.05 g (0.035 moles) of 2-morpholinopropylamine is stirred at 80° C. for 3 hours. After cooling, 10 ml of water are added, drop by drop, to the reaction mixture, the precipitated crystals are filtered, washed with water, then with diethyl ether.

Thus, 1.59 g (95.8%) of the title compound are obtained. M.p.: 188–191° C.

EXAMPLE 128

2-(5-Amino-3-methylthio-1H-1,2,4-triazole-1-yl)-5-
[2-/3-methyl-3-(2-morpholinoethylamino)propoxy/
phenyl]-1,3,4-thiadiazole A mixture of 1.50 g (0.0035 moles) of 2-(5-amino-3-methylthio-1H-1,2,4-triazole-1-yl)-5-/2-(3-bromopropoxy)phenyl/-1,3,4-thiadiazole and 3.30 g (0.03 moles) of 2-methyl-2-morpholinoethylamine is stirred at 80° C. for 3 hours. After cooling, 10 ml of ether are added, drop by drop, to the reaction mixture, the precipitated crystals are filtered, squashed with water, then with ether.

Thus, 1.47 g (86.0%) of the title compound are obtained. M.p.: 154–157° C.

EXAMPLE 129

2-(5-Amino-3-methylthio-1H-1,2,4-triazole-1-yl)-5-
[2-/3-(3-morpholinopropylamino)propoxy/phenyl]-1,
3,4-thiadiazole A mixture of 1.45 g (0.0035 moles) of 2-(5-amino-3-methylthio-1H-1,2,4-triazole-1-yl)-5-/2-(3-bromopropoxy)phenyl/-1,3,4-thiadiazole and 5.05 g (0.035 moles) of 3-morpholinopropylamine is stirred at 80° C. for 1 hour. After cooling, 20 ml of water are added, drop by drop, to the reaction mixture, the precipitated crystals are filtered, washed with water, then with acetonitrile.

Thus, 1.48 g (86.5%) of the title compound are obtained.
M.p.: 157–160° C.

EXAMPLE 130

2-(5-Amino-3-piperidino-1H-1,2,4-triazole-1-yl)-5-
{2-[4-methyl-4-/2-(3,4-dimethoxyphenyl)
ethylylamino/butoxy]phenyl}-1,3,4-thiadiazole A mixture of 0.48 g (0.001 moles) of 2-(5-amino-3-piperidino-1H-1,2,4-triazole-1-yl)-5-/2-(4-bromobutoxy) phenyl/-1,3,4-thiadiazole and 1.95 g (0.035 moles) of N-methyl-N-/2-(3,4-dimethoxyphenyl)ethyl/amine is stirred at 100° C. for 1 hour. After cooling, 10 ml of other are added, drop by drop, to the reaction mixture, the precipitated crystals are filtered, washed with water, then with diethyl ether.

Thus, 0.29 g (49.1%) of the title compound are obtained.
M.p.: 120–122° C.

EXAMPLE 131

2-(5-Amino-3-morpholino-1H-1,2,4-triazole-1-yl)-5-
[2-/3-(2-morpholinoethylamino)propoxy/phenyl]-1,
3,4-thiadiazole A mixture of 1.45 g (0.0035 moles) of 2-(5-amino-3-morpholino-1H-1,2,4-triazole-1-yl)-5-/2-(3-bromoprotoxy) phenyl/-1,3,4-thiadiazole and 5.05 g (0.035 moles) of 2-morpholinoethylamine is stirred at 5° C. for 2.5 hours. After cooling, 30 ml of water are added, drop by drop, to the reaction mixture, the precipitated crystals are filtered, washed with water, then with ether.

Thus, 1.51 g (83.9%) of the title compound are obtained.

EXAMPLE 132

2-(5-Amino-3-piperidino-1H-1,2,4-triazole-1-yl)-5-
[2-/2-methyl-2-(2-hydroxyethylamino)ethoxy/
phenyl]-1,3,4-thiadiazole A mixture of 0.36 g (0.0008 moles) of 2-(5-amino-3-piperidino-1H-1,2,4-triazole-1-yl)-5-/2-(2-bromoethoxy) phenyl/-1,3,4-thiadiazole and 1 ml of 2-methylaminoethanol is stirred at 100° C. for 1.5 hours. After cooling, 5 ml of water are added, drop by drop, to the reaction mixture, the precipitated crystals are filtered, washed with water, then with acetonitrile.

Thus, 0.21 g (73.5%) of the title compound are obtained.
What is claimed is:

1. A 2-(1,2,4-triazole-1-yl)-1,3,4-thiadiazole derivative of the formula

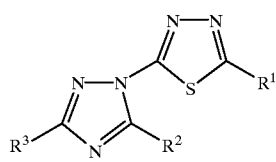

I wherein
$R^1$ represents a hydrogen atom, a $C_{1-4}$ alkyl group or a phenyl group optionally substituted by 1 to 3 substituents selected from the group consisting of a halo atom, a hydroxy group, a nitro group, a $C_{1-4}$ alkoxy group, a ($C_{1-4}$ alkyl)amino group and a di($C_{1-4}$ alkyl)amino group;

or a group of the formula

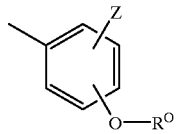

a wherein
Z stands for a hydrogen atom or a $C_{1-4}$ alkoxy group,
$R^0$ means a group of the formula Alk-$NR^4R^5$ wherein
Alk is a $C_{1-6}$ straight or branched chain alkylene group,
$R^4$ and $R^5$ represent, independently, a hydrogen atom, a $C_{2-6}$ alkenyl group, a $C_{1-8}$ alkyl group optionally substituted by a substituent selected from the group consisting of a hydroxy group, a ($C_{1-4}$ alkyl)amino group, a di($C_{1-4}$ alkyl)amino group, a phenyl group—wherein the latter can be substituted by 1 to 3 $C_{1-4}$ alkoxy group(s)—and a 5- or 6-membered saturated heterocyclic group containing one or more nitrogen atom(s) or a nitrogen and an oxygen atom and being linked through its nitrogen atom, said heterocyclic group being optionally substituted by a $C_{1-4}$ alkyl group, or
$R^4$ and $R^5$ form together with the adjacent nitrogen atom and optionally with one or more further nitrogen and/or oxygen and/or sulfur atom(s) a 5- to 10-membered saturated heterocyclic group optionally substituted by a $C_{1-4}$ alkyl group or a phenyl group which latter is optionally substituted by a $C_{1-4}$ alkoxy group,
one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group,
and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl-($C_{1-4}$ alkyl) group,
and pharmaceutically acceptable acid addition salts thereof.

2. A 2-(1,2,4-triazole-1-yl)-1,3,4-thiadiazole derivative as claimed in claim 1, in which
$R^1$ represents a hydrogen atom, a $C_{1-4}$ alkyl group or a phenyl group optionally substituted by 1 to 3 substituent(s) selected from the group consisting of a halo atom, a hydroxy group, a nitro group, a $C_{1-4}$ alkoxy group, a ($C_{1-4}$ alkyl)amino group and a di($C_{1-4}$ alkyl)amino group,
one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of R² and R³ means a group of the formula —SR, wherein R represents a $C_{1-8}$ alkyl group, a $C_{2-6}$ alkenyl group or a $C_{2-6}$ alkenyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl($C_{1-4}$ alkyl) group, and pharmaceutically acceptable acid addition salts thereof.

3. A 5-phenyl-2-(1,2,4-triazole-1-yl)-1,3,4-thiadiazole derivative of the formula

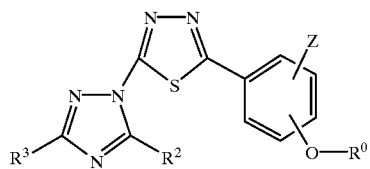

Ia as claimed in claim 1, wherein $R^0$ represents a group of the formula Alk-NR⁴R⁵, wherein Alk is a $C_{1-6}$ straight or branched chain alkylene group, R⁴ and R⁵ mean, independently, a $C_{1-6}$ alkyl group or a $C_{2-6}$ alkenyl group, or R⁴ and R⁵ form together with the adjacent nitrogen atom and optionally with one or more further nitrogen and/or oxygen and/or sulfur atom(s) a 5 to 10-membered saturated heterocyclic group optionally substituted by a $C_{1-4}$ alkyl group or a phenyl group which latter is optionally substituted by a $C_{1-4}$ alkoxy group, Z stands for a hydrogen atom or a $C_{1-4}$ alkoxy group, one of R² and R³ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of R² and R³ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl($C_{1-4}$ alkyl) group, and pharmaceutically acceptable acid addition salts thereof.

4. A 5-(aminoalkoxyphenyl)-2-(1,2,4-triazole-1-yl)-1,3,4-thiadiazole derivative of the formula

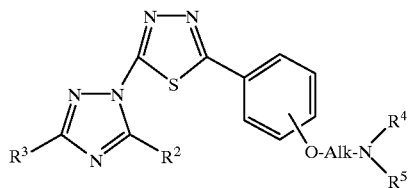

Ib as claimed in claim 1, wherein one of R² and R³ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of R² and R³ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group, and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group and a halophenyl($C_{1-4}$ alkyl) group, Alk means a $C_{1-6}$ alkylene group, R⁴ and R⁵ represent, independently, a hydrogen atom or a $C_{1-8}$ alkyl group optionally substituted by a substituent selected from the group consisting of a hydroxy group, a ($C_{1-4}$ alkyl)amino group, a di-($C_{1-4}$ alkyl) amino group, a phenyl group—wherein the latter can be substituted by 1 to 3 $C_{1-4}$ alkoxy group(s)—and a 5- or 6-membered saturated heterocyclic group containing one or more nitrogen atom(s) or a nitrogen and an oxygen atom and being linked through its nitrogen atom, said heterocyclic group being optionally substituted by a $C_{1-4}$ alkyl group, and pharmaceutically acceptable acid addition salts thereof.

5. A 2-(1,2,4-triazole-1-yl)-1,3,4-thiadiazole derivative as claimed in claim 1 or 2, in which R¹ represents a hydrogen atom, a methyl group, an ethyl group or a phenyl group optionally substituted by 1 to 3 substituent(s) selected from the group consisting of a halo atom, a hydroxy group, a nitro group, a methoxy group and a dimethylamino group, R² stands for an amino group optionally substituted by a halobenzyl group, R³ means a piperidine-1-yl, piperazine-1-yl, morpholine-1-yl or 4-methylpiperazine-1-yl group or a group of the formula —SR, wherein R is a methyl group, and pharmaceutically acceptable acid addition salts thereof.

6. A 5-phenyl-2-(1,2,4-triazole-1-yl)-1,3,4-thiadiazole derivative as claimed in claim 1 or 3, in which R⁰ represents a group of the formula Alk-NR⁴R⁵, wherein Alk stands for an ethylene group or a propylene group, R⁴ and R⁵ mean, independently, a $C_{1-3}$ alkyl group, or R⁴ and R⁵ form together with the adjacent nitrogen atom a pyrrolidinyl group, R² is an amino group, R³ stands for an amino group or a piperidinyl or 4-methylpiperazinyl group, said groups being linked through the nitrogen atom, or a group of the formula —SR, wherein R is a $C_{1-3}$ alkyl group, and optionally the amino group is substituted by two methyl groups or two allyl groups, Z represents a hydrogen atom, and pharmaceutically acceptable acid addition salts thereof.

7. A 5-(aminoalkoxyphenyl)-2-(1,2,4-triazole-1-yl)-1,3,4-thiadiazole derivative as claimed in claim 1 or 4, in which
$R^4$ represents a hydrogen atom or a $C_{1-2}$ alkyl group,
$R^5$ stands for an ethyl group substituted by a substituent selected from the group consisting of hydroxy group, dimethoxy phenyl group and morpholino group,
$R^2$ is an amino group,
$R^3$ means a piperidyl group or a group of the formula —SR, wherein
R stands for a $C_{1-3}$ alkyl group,
Alk represents a $C_{2-3}$ alkylene group, and pharmaceutically acceptable acid addition salts thereof.

8. Any of the following compounds as claimed in claim 1:
2-/5-amino-3-(4-methylpiperazino)-1H-1,2,4-triazole-1-yl/-5-(2,6-dichloro-phenyl)-1,3,4-thiadiazole,
2-(5-amino-3-methylthio-1H-1,2,4-triazole-1-yl)-5-/3-(3-dimethylaminopropoxy)phenyl/-1,3,4-thiadiazole,
2-(5-amino-3-dimethylamino-1H-1,2,4-triazole-1-yl)-5-/2-(3-dimethylaminopropoxy)phenyl/-1,3,4-thiadiazole,
2-/5-amino-3-(2-methylethylthio)-1H-1,2,4-triazole-1-yl/-5-/2-(3-dimethylaminopropoxy)phenyl/-1,3,4-thiadiazole,
2-(5-amino-3-piperidino-1H-1,2,4-triazole-1-yl)-5-/2-(3-dimethylaminopropoxy)phenyl/-1,3,4-thiadiazole,
2-(5-amino-3-methylthio-1H-1,2,4-triazole-1-yl)-5-/4-(2-dimethylaminoethoxy)phenyl/-1,3,4-thiadiazole,
2-(5-amino-3-methylthio-1H-1,2,4-triazole-1-yl)-5-/2-(3-pyrrolidinopropoxy)phenyl/-1,3,4-thiadiazole,
2-(5-amino-3-methylthio-1H-1,2,4-triazole-1-yl)-5-/2-/3-di(2-methylethyl)aminopropoxy/-phenyl/-1,3,4-thiadiazole,
2-/5-amino-3-(4-methylpiperazine-1-yl)-1H-1,2,4-triazole-1-yl/-5-/4-(3-dimethylaminopropoxy)phenyl/-1,3,4-thiadiazole,
2-(5-amino-3-diallylamino-1H-1,2,4-triazole-1-yl)-5-/2-(3-dimethylaminopropoxy)phenyl/-1,3,4-thiadiazole,
2-(5-amino-3-pyrrolidino-1H-1,2,4-triazole-1-yl)-5-/2-(3-dimethylaminopropoxy)phenyl/-1,3,4-thiadiazole,
2-(5-amino-3-piperidino-1H-1,2,4-triazole-1-yl)-5-{2-[2-/2-ethyl-2-(2-hydroxyethyl)amino/ethoxy]phenyl}1,3,4-thiadiazole,
2-(5-amino-3-piperidino-1H-1,2,4-triazole-1-yl)-5-[-2-/2-(2-morpholinoethyl)amino/ethoxy]phenyl-1,3,4-thiadiazole,
2-(5-amino-3-methylthio-1H-1,2,4-triazole-1-yl)-5-{2-[3-methyl-3-/2-(3,4-dimethoxyphenylethyl)amino/propoxy]phenyl}-1,3,4-thiadiazole,
2-(5-amino-3-piperidino-1H-1,2,4-triazole-1-yl)-5-{2-[3-methyl-3-/2-(3,4-dimethoxyphenylethyl)amino/propoxy]phenyl}-1,3,4-thiadiazole,
2-/5-amino-3-(1-methylethylthio)-1H-1,2,4-triazole-1-yl/-5-{2-[3-methyl-3-/2-(3,4-dimethoxyphenylethyl)amino/propoxy]phenyl}-1,3,4-thiadiazole,
2-(5-amino-3-methylthio-1H-1,2,4-triazole-1-yl)-5-{3-[3-methyl-3-/2-(3,4-dimethoxyphenylethyl)amino/propoxy]phenyl}-1,3,4-thiadiazole,
2-(5-amino-3-methylthio-1H-1,2,4-triazole-1-yl)-5-{4-[3-methyl-3-/2-(3,4-dimethoxyphenylethyl)amino/propoxy]phenyl}-1,3,4-thiadiazole, and pharmaceutically acceptable acid addition salts thereof.

9. A process for the preparation of a 2-(1,2,4-triazole-1-yl)-1,3,4-thiadiazole derivative of the formula I, wherein $R^1$, $R^2$ and $R^3$ are as defined in claim 1, or a pharmaceutically acceptable acid addition salt thereof, characterized by a) cyclizing a thiocarboxylic acid hydrazone of the formula

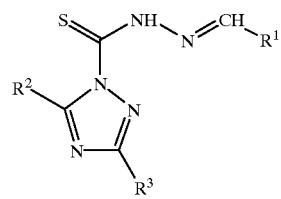

II wherein $R^1$, $R^2$ and $R^3$ are as defined above, with an oxidizing agent; or b) reacting a thiocarboxylic acid hydrazide of the formula

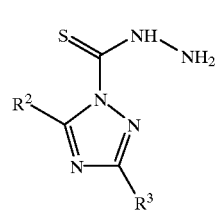

III wherein $R^2$ and $R^3$ are as stated above, with an orthoester of the formula

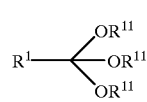

IV wherein $R^1$ is as defined above, $R^{11}$ represents a leaving group; or c) for the preparation of a compound of the formula I, wherein $R^1$ stands for a group of the formula a, $R^2$, $R^3$, $R^0$ and z are as defined in claim 1, reacting a phenol of the formula

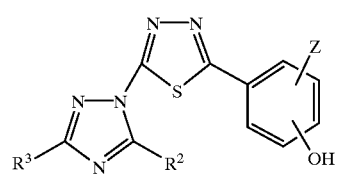

V wherein $R^2$ $R^3$ and Z are as stated above, with an aminoalkylhalide of the formula

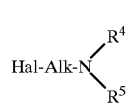

VI wherein Alk, $R^4$ and $R^5$ are as defined in connection with the definition of $R^1$, Hal represents a halo atom; or d) for the preparation of a compound of the formula I, wherein $R^1$ stands for a group of the formula a, $R^2$, $R^3$, $R^0$ and Z are as defined in claim 1, reacting a halide of the formula

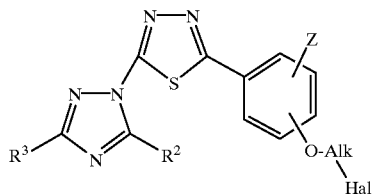

VII wherein $R^2$, $R^3$ and Z are as stated above, Alk is as defined in connection with the definition of $R^1$, Hal represents a halo atom, with an amine of the formula

VIII wherein $R^4$ and $R^5$ are as defined in connection with the definition of $R^1$;
and optionally converting a thus-obtained compound of the formula I to a pharmaceutically acceptable acid addition salt thereof, or liberating a compound of the formula I from its salt.

10. A pharmaceutical composition comprising a 2-(1,2,4-triazole-1-yl)-1,3,4-thiadiazole derivative of the formula I, wherein $R^1$, $R^2$ and $R^3$ are as defined in claim 1, or a pharmaceutically acceptable acid addition salt thereof as the active ingredient and one or more conventional carrier(s).

11. A pharmaceutical composition as claimed in claim 10, comprising a 2-(1,2,4-triazole-1-yl)-1,3,4-thiadiazole derivative of the formula I, wherein $R^1$, $R^2$ and $R^3$ are as defined in claim 2, or a pharmaceutically acceptable acid addition salt thereof as the active ingredient.

12. A pharmaceutical composition as claimed in claim 10, comprising a 5-phenyl-2-(1,2,4-triazole-1-yl)1,3,4-thiadiazole derivative of the formula Ia, wherein $R^0$, $R^2$, $R^3$ and Z are as defined in claim 3, or a pharmaceutically acceptable acid addition salt thereof as the active ingredient.

13. A pharmaceutical composition as claimed in claim 10, comprising a 5-(aminoalkoxyphenyl)-2-(1,2,4-triazole-1-yl)-1,3,4-thiadiazole derivative of the formula Ib, wherein $R^2$, $R^3$, $R^4$, $R^5$ and Alk are as defined in claim 4, or a pharmaceutically acceptable acid addition salt thereof as the active ingredient.

14. A pharmaceutical composition as claimed in claim 10 or 11, comprising a 2-(1,2,4-triazole-1-yl)-1,3,4-thiadiazole derivative of the formula I, wherein $R^1$, $R^2$ and $R^3$ are as defined in claim 5, or a pharmaceutically acceptable acid addition salt thereof as the active ingredient.

15. A pharmaceutical composition as claimed in claim 10 or 12, comprising a 5-phenyl-2-(1,2,4-triazole-1-yl)-1,3,4-thiadiazole derivative of the formula Ia, wherein $R^0$, $R^2$, $R^3$ and Z are as defined in claim 6, or a pharmaceutically acceptable acid addition salt thereof as the active ingredient.

16. A pharmaceutical composition as claimed in claim 10 or 13, comprising a 5-(aminoalkoxyphenyl)-2-(1,2,4-triazole-1-yl)-1,3,4-thiadiazole derivative of the formula Ib, wherein $R^2$, $R^3$, $R^4$, $R^5$ and Alk are as defined in claim 7, or a pharmaceutically acceptable acid addition salt thereof as the active ingredient.

17. A pharmaceutical composition as claimed in claim 10, comprising any of the compounds claimed in claim 8 or a pharmaceutically acceptable acid addition salt thereof as the active ingredient.

18. A method of treatment in which a patient suffering from heart insufficiency or a disease of the central nervous system is treated with a non-toxic dose of a 2-(1,2,4-triazole-1-yl)-1,3,4-thiadiazole derivative of the formula I, wherein $R^1$, $R^2$ and $R^3$ are as defined in claim 1, or a pharmaceutically acceptable acid addition salt thereof.

19. An intermediate of the formula

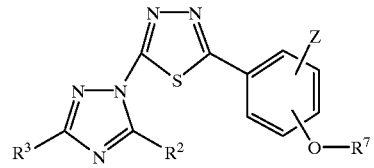

IX wherein
$R^7$ means a group of the formula —Alk—L, wherein
Alk represents a $C_{1-6}$ straight or branched chain alkylene group,
L stands for a halo atom or a hydroxy group,
Z is a hydrogen atom or a $C_{1-4}$ alkoxy group,
one of $R^2$ and $R^3$ is an amino group, while the other stands for an amino group or a 5- to 10-membered saturated heterocyclic group containing one or more nitrogen and/or oxygen and/or sulfur atom(s) and being linked through its nitrogen atom, said heterocyclic group being optionally substituted by a $C_{1-4}$ alkyl group, a phenyl group or a halophenyl group, or the latter one of $R^2$ and $R^3$ means a group of the formula —SR, wherein R represents a $C_{1-8}$ alkyl group, a $C_{2-6}$ alkenyl group or a $C_{2-6}$ alkynyl group, wherein the alkyl group is optionally substituted by a phenyl group or a halophenyl group,
and optionally one or both amino group(s) is/are substituted by 1 or 2 substituent(s) selected from the group consisting of a $C_{1-6}$ alkyl group, a $C_{2-6}$ alkenyl group, a phenyl($C_{1-4}$ alkyl) group or a halophenyl-($C_{1-4}$ alkyl) group,
and acid addition salts thereof.

\* \* \* \* \*